US009611347B2

(12) United States Patent
Schrock et al.

(10) Patent No.: US 9,611,347 B2
(45) Date of Patent: Apr. 4, 2017

(54) CATALYSTS AND METHODS FOR RING OPENING METATHESIS POLYMERIZATION

(71) Applicant: Massachusetts Institute of Technology, Cambridge, MA (US)

(72) Inventors: Richard Royce Schrock, Winchester, MA (US); Benjamin Autenrieth, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 38 days.

(21) Appl. No.: 14/627,802

(22) Filed: Feb. 20, 2015

(65) Prior Publication Data

US 2015/0240008 A1    Aug. 27, 2015

Related U.S. Application Data

(60) Provisional application No. 61/942,722, filed on Feb. 21, 2014.

(51) Int. Cl.
```
C08F 132/08      (2006.01)
C07F 11/00       (2006.01)
B01J 31/14       (2006.01)
B01J 31/18       (2006.01)
B01J 31/22       (2006.01)
C08G 61/08       (2006.01)
```

(52) U.S. Cl.
CPC .......... *C08F 132/08* (2013.01); *B01J 31/146* (2013.01); *B01J 31/181* (2013.01); *B01J 31/1805* (2013.01); *B01J 31/2226* (2013.01); *B01J 31/2265* (2013.01); *C07F 11/00* (2013.01); *C08G 61/08* (2013.01); *B01J 2231/543* (2013.01); *B01J 2531/66* (2013.01); *C08G 2261/3325* (2013.01); *C08G 2261/418* (2013.01)

(58) Field of Classification Search
CPC .... B01J 31/146; B01J 31/1805; B01J 31/181; B01J 31/2226; B01J 31/2265; B01J 2231/543; B01J 2531/66; C07F 11/00; C08F 132/08; C08G 61/08; C08G 2261/3325; C08G 2261/418
USPC ............. 526/308, 134, 170, 283; 525/332.1; 548/408; 556/57
See application file for complete search history.

(56) References Cited

U.S. PATENT DOCUMENTS

| 4,657,981 A | 4/1987 | Klosiewicz | |
| 9,085,595 B2* | 7/2015 | Schrock | C07F 11/00 |
| 2013/0116434 A1* | 5/2013 | Schrock | C07F 11/00 546/2 |

FOREIGN PATENT DOCUMENTS

JP    2007023202 A    2/2007

OTHER PUBLICATIONS

Tsunogae et al. (Syndioselective Ring-Opening Metathesis Polymerization of endo-Dicyclopentadiene with Tungsten Complexes Having Imido Ligands: Development of Crystalline Syndiotactic Hydrogenated Poly(endo-dicyclopentadiene), Macromolecules 2006, 39, 30-38).*
Jeong et al. (Syntheses of Tungsten tert-Butylimido and Adamantylimido Alkylidene Complexes Employing Pyridinium Chloride as the Acid, Organometallics 2012, 31, 6522-6525).*
Peryshkov et al. (Z-Selective Olefin Metathesis Reactions Promoted by Tungsten Oxo Alkylidene Complexes, J. Am. Chem. Soc. 2011, 133, 20754-20757).*
Schrock et al. (Synthesis of Tungsten Oxo Alkylidene Complexes, Organometallics 2012, 31, 7278-7286).*
Müller et al. (B(C6F5)3 Activation of Oxo Tungsten Complexes That Are Relevant to Olefin Metathesis, Organometallics, Sep. 2013, 32, 5256-5259).*
Davidson, et al., "Polymerization of Dicyclopentadiene: A Tale of Two Mechanisms", Macromolecules, 29, 1996, 786-788.
Davidson, et al., "The Polymerization of Dicyclopentadiene: An Investigation of Mechanism", Journal of Molecular Catalysis A: Chemical, 133, 1998, 67-74.
Flook, et al., "Five-Coordinate Rearrangements of Metallacyclobutane Intermediates During Ring-Opening Metathesis Polymerization of 2,3-Discarboalkoxynorbornes by Molybdenum and Tungsten Monoalkoxide Pyrrolide Initiators", Organometallics, 31(17), 2012, 6231-6243.
Flook, et al., "Synthesis of cis, syndiotactic ROMP Polymers Containing Alternating Enantiomers", J Am Chem Soc., 133, 2011, 1784-1786.
Flook, et al., "Z-Selective and Syndioselective Ring-Opening Metathesis Polymerization (ROMP) Initiated by Monoaryloxidepryrrolide (MAP) Catalysts", Macromolecules vol. 43 No. 18, 2010, pp. 7515-7522.
Flook, et al., "Z-Selective Olefin Metathesis Processes Catalyzed by a Molybdenum Hexaisopropyltenphenoxide Momopyrrolide Complex", J Am Chem Soc., 131(23), 2009, 7962-7963.
Hamilton, et al., "C N.m.r. Spectra of Ring-Opened Polymers of 1-Methylbicyclo[22.1]Hepta-2-Ene and Their Hydrogenated Products", British Polymer Journal, 16, 1984.
Hamilton, et al., "Ring-Opening Polymerization of Endo and Exo-Dycyclopentadiene and Their 7,8-Dihydro Derivatives", Journal of Molecular Catalysis, 36, 1986, 115-125.
Hayano, et al., "A New Method for Catalytic Synthesis of Block Copolymers via ROMP: Development of Stereoblock Copolymer(Endo-Dicyclopentadiene)", Chem. Lett., 37(5), 2008, 518-519.

(Continued)

*Primary Examiner* — Ling Choi
*Assistant Examiner* — Chun-Cheng Wang
(74) *Attorney, Agent, or Firm* — Stoel Rives LLP

(57) ABSTRACT

The present invention, among other things, provides highly syndiotactic poly(dicyclopentadiene) and/or hydrogenated poly(dicyclopentadiene), compositions thereof, and compounds and methods for preparing the same. In some embodiments, a provided compound is a compound of formula I, II or III. In some embodiments, a provided method comprises providing a compound of formula I, II or III.

16 Claims, 21 Drawing Sheets

(56) References Cited

OTHER PUBLICATIONS

Hayano, et al., "Hydrogenated Ring-Opened Poly(Endo-Dicyclopentadiene)s Made Via Stereoselective ROMP Catalyzed by Tungsten Complexes: Crystalline Tactic Polymers and Amorphous Atactic Polymer", Macromolecules, 39, 2006, 4663-4670.

Hayano, et al., "Iso—an Syndio-Selective ROMP of Norbornene and Tetracyclododecene; Effects of Tacticity Control on the Hydrogenated Ring-Opened Poly(cycloolefins)s", Macromolecules, vol. 47, 2014, pp. 7797-781.

Hayano, et al., "Stereospecific Ring-Opening Metathesis Polymerization of Cycloolefins Using Novel Molybdenum and Tungsten Complexes Having Biphenolate Ligands. Development of Crystalline Hydrogenated Poly(Endo-Dicyclopentadiene) and Poly(Norbornene)", Macromolecules, 36, 2003, 7422-7431.

Hayano, et al., "Stereospecific Ring-Opening Metathesis Polymerization of Endo-Dicyclopentadiene by Schrock-Hoveyda Catalyst and Novel Mo- and W- Based Complexes. Development of Crystalline Hydrogenated Poly(Endo-Dicyclopentadiene)", Chem. Lett., 32(8), 2003, 670-671.

Hayano, et al., "Syndioselective Ring-Opening Metathesis Polymerization of Endo-Dicyclopentadiene with Tungsten Complexes Having Imido Ligands: Development of Crystalline Syndiotactic Hydrogenated Poly(Endo-Dicyclopentadiene)", Macromolecules, 39, 2006, 30-38.

Hayano, et al., "Syndiospecific Ring-Opening Metathesis Polymerization of Engo-Dicyclopentadiene by Tungsten(VI)-Phenylimido Catalyst", Chem. Lett., 34(11), 2005, 1520-1521.

Hayano, et al., "Thermoplastic Polymers, their manufacture and their molding materials", Chemistry of Synthetic High Polymers, 35-8, Feb. 1, 2007, 2 pages.

Jeong, et al., "Z-Selective Ring-Opening Metahtesis Polymerization of 3-Substituted Cyclootenes by Monoaryloxide Pyrrolide Imido Alkylidene (MAP) Catalysts of Molybdenum and Tungsten", Organometallics, 32, 2013, 4843-4850.

Keitz, et al., "Cis-Selective Ring-Opening Metathesis Polymerization with Ruthenium Catalysts", Journal of American Chemical Society, 134(4), 2012, 2040-2043.

Kobayashi, et al., "Regio- and Stereoselective Ring-Opening Metathesis Polymerization of 3-Substituted Cyclooctenes", JACS, 133, 2011, 5794-5797.

Lindmark-Hamberg, et al., "Acyclic Metathesis Polymerization. The Olefin Metathesis Reaction of 1,5-Hexadiene and 1,9-Dacadiene", Macromolecules, 20, 1987, 2949-2951.

O'Dell, et al., "Polymerization of Enantiomerically Pure 2,3-Dicarboalkoxymorbarnadienes and 5,6-Distributed Norbornenes by Well-Characterized Molybdenum Ring-Opening Metathesis Polymerization Initiators. Direct Determination of Tacticity in Cis, Highly Tactic and Trans,", Highly Tactic Polymers, J. Am. Chem. Soc., 116, 1994, 3414-3423.

Oshika, et al., "Ring-Opening Polymerization of Norbornene and Its Derivitaves by MoCl59 Wc16 and ReC15 Catalysts", Bulletin of the Chemical Society of Japan, 41, 1968, 211-217.

Pacreau, et al., "Linear Polymerization of Engo-Dicyclopentadiene Initiated by Metathesis Catalysts", Makromol. Chem., 188, 1987, 2585-2595.

PCT/US2015/016801, International Search Report and Written Opinion, Jul. 27, 2015, 18 pages.

Rosebrugh, et al., "Synthesis of Highly Cis, Syndiotactic Polymers via Ring-Opening Metathesis Polymerization Using Ruthenium Metathesis Catalysts", Journal of American Chemical Society, 135(27), 2013, 10032-10035.

Schrock, et al., "Exploring Factors that Determine Cis/Trans Structure and Tacticity in Polymers Prepared by Ring-Opening Metathesis Polymerization with Initiators of the Type Syn-and Anti-Mo(NAr)(CHCMe2Ph)(OE)2. Observation of a Temperature-Dependent Cis-Trans Ratio", Macromolecules, vol. 28, No. 17, 1998, 5933-5940.

Schrock, et al., "Molybdenum and Tungsten Imido Alkylidene Complexes as Efficient Olefin-Metathesis Catalysts", Agnew. Chem. Int. Ed., 42, 2003, 4592-4633.

Schrock, et al., "Synsthesis of Stereoregular ROMP Polymers using Molybdenum and Tungsten Imido Alklidene Initiators", Dalton Trans, 40(29), 2011, 7484-7495.

Wintein, et al., "Polymerization of bicyclo[2.2.1]hept-2-ene or one of its derivatives by ring opening", Chem. Abstr., 86, 122050n, 1997, 1 page.

Yuan, et al., "Synthesis and ROMP Chemistry and Dedafluoroterphenoxide Molybdenum Imido Akylidene and Ethylene Complexes", Organometallics, 32, 2013, 2983-2992.

* cited by examiner (a)

(b)

CATALYSTS AND METHODS FOR RING OPENING METATHESIS POLYMERIZATION

CROSS-REFERENCE TO RELATED APPLICATIONS

The present invention claims priority to U.S. Provisional Application No. 61/942,722, filed Feb. 21, 2014, the entirety of which is incorporated herein by reference.

STATEMENT REGARDING FEDERALLY SPONSORED RESEARCH OR DEVELOPMENT

This invention was made with government support under Grant No. DE-FG02-86ER13564 awarded by the Department of Energy. The government has certain rights in the invention.

FIELD OF THE INVENTION

The present invention generally relates to polymer and/or metathesis reactions.

BACKGROUND

Catalytic metathesis has transformed chemical synthesis and offers exceptionally efficient pathways for the synthesis of many commercially important chemicals including biologically active molecules, oleochemicals, renewables, fine chemicals, and polymeric materials. There remains an unmet need for improved methods and catalysts for metathesis reactions, for example, in terms of better catalyst stability, activity, efficiency and/or stereoselectivity.

SUMMARY

Prior to the present application, some polymers cannot be prepared in certain desired configurations and stereoregularities with high stereochemical control; for example, highly syndiotactic poly(dicyclopentadiene) ("poly(DCPD)") and hydrogenated poly(DCPD) could not be obtained. In some embodiments, the present invention provides poly(DCPD) with high stereoregularity. In some embodiments, the present invention provides highly syndiotactic poly(DCPD). In some embodiments, a provided poly(DCPD) is greater than 80% syndiotactic. In some embodiments, a provided poly(DCPD) is greater than 80% syndiotactic, and the double bonds in the polymer backbone are greater than 95% cis. In some embodiments, the present invention provides highly syndiotactic hydrogenated poly(DCPD). In some embodiments, a provided hydrogenated poly(DCPD) is greater than 80% syndiotactic.

In some embodiments, the present invention provides a composition comprising highly syndiotactic poly(DCPD). In some embodiments, the present invention provides a composition comprising highly syndiotactic hydrogenated poly(DCPD).

In some embodiments, the present invention provides methods for preparing highly syndiotactic poly(DCPD) and/or hydrogenated poly(DCPD). In some embodiments, a provided method comprising ring-opening metathesis polymerization ("ROMP"). In some embodiments, the present invention provides a method for preparing highly syndiotactic poly(DCPD), comprising ring-opening metathesis polymerization of dicyclopentadiene. In some embodiments, a provided method comprises providing a compound of formula I:

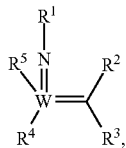

wherein each variable is independently as defined and described, infra. In some embodiments, a provided method comprises providing a compound of formula II:

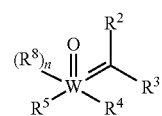

wherein each variable is independently as defined and described, infra. In some embodiments, a provided method comprises providing a compound of formula III:

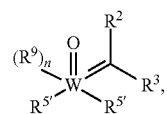

wherein each variable is independently as defined and described, infra. In some embodiments, a provided method comprises providing a compound of formula III and a Lewis acid.

In some embodiments, the present invention provides a method for improving the stereoselectivity of ring opening metathesis polymerization, comprising providing a Lewis acid.

In some embodiments, the present invention provides compounds that, among other things, are useful for preparing a provided polymer and/or performing stereoselective ring opening metathesis polymerization. In some embodiments, the present invention provides a compound of formula I. In some embodiments, the present invention provides a compound of formula II. In some embodiments, the present invention provides a compound of formula II-a:

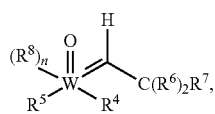

wherein each variable is independently as defined and described, infra. In some embodiments, the present invention provides a compound of formula III.

DETAILED DESCRIPTION OF CERTAIN EMBODIMENTS

Figure 1:
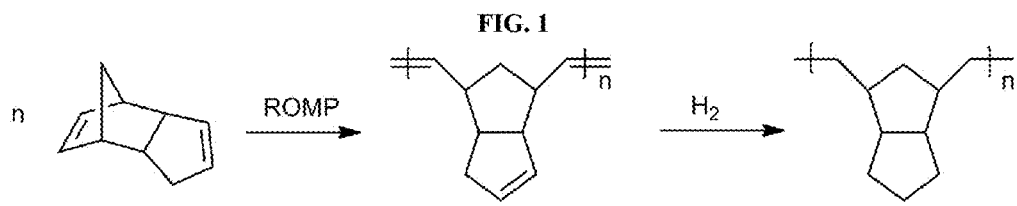
FIG. 1. Production of poly(DCPD) and hydrogenated poly(DCPD).

1. General Description of Certain Embodiments of the Invention

Polymers with high stereoregularity are important materials and are highly desirable. Prior to the present application, some polymers cannot be prepared in certain configurations and/or stereoregularity with high stereochemical control; for example, highly syndiotactic poly(dicyclopentadiene) ("poly(DCPD)") and hydrogenated poly(DCPD) have not been successfully prepared until the present invention.

In some embodiments, the present invention provides highly syndiotactic poly(DCPD). In some embodiments, the present invention provides highly cis, syndiotactic poly (DCPD). In some embodiments, the present invention provides highly syndiotactic hydrogenated poly(DCPD).

In some embodiments, the present invention provides methods for preparing highly syndiotactic poly(DCPD). In some embodiments, the present invention provides methods for preparing highly syndiotactic, hydrogenated poly(DCPD).

In some embodiments, the present invention provides compounds useful for preparing highly syndiotactic poly (DCPD) and/or hydrogenated poly(DCPD).

In some embodiments, the present invention provides a composition, comprising highly syndiotactic poly(DCPD). In some embodiments, the present invention provides a composition, comprising highly syndiotactic hydrogenated poly(DCPD).

In some embodiments, the present invention provides a compound of formula I:

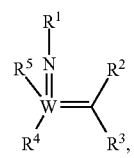

wherein:
R$^1$ is —C(R$^{1a}$)$_3$;
each R$^{1a}$ is independently an optionally substituted group selected from C$_{1-10}$ aliphatic, C$_{1-10}$ heteroalkyl having 1-3 heteroatoms independently selected from nitrogen, oxygen or sulfur, phenyl, a 3-7 membered saturated or partially unsaturated carbocyclic ring, an 8-10 membered bicyclic or polycyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; or:
two R$^{1a}$ groups are optionally taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur; or:

three $R^{1a}$ groups are optionally taken together with the carbon atom to which they are attached to form an optionally substituted 4-10 membered, bicyclic or polycyclic, saturated or partially unsaturated ring having 0-4 heteroatoms independently selected from nitrogen, oxygen or sulfur;

each of $R^2$ and $R^3$ is independently —R, —OR, —SR, —N(R)$_2$, —OC(O)R, —S(O)R, —SO$_2$R, —SO$_2$N(R)$_2$, —C(O)N(R)$_2$, —NRC(O)R, or —NRSO$_2$R; or:

$R^2$ and $R^3$ are optionally taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur;

each R is independently hydrogen or an optionally substituted group selected from $C_{1-10}$ aliphatic, $C_{1-10}$ heteroalkyl having 1-3 heteroatoms independently selected from nitrogen, oxygen or sulfur, phenyl, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; or:

two R groups are optionally taken together with the intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen or sulfur;

$R^4$ is optionally substituted 5-14 membered heteroaryl having 1-4 heteroatoms independently selected from nitrogen, oxygen or sulfur, wherein at least one heteroatom is nitrogen;

$R^5$ is —OAr$^a$; and

Ar$^a$ is optionally substituted

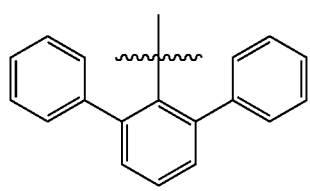

In some embodiments, the present invention provides a compound of formula II:

wherein:

each of $R^2$ and $R^3$ is independently —R, —OR, —SR, —N(R)$_2$, —OC(O)R, —S(O)R, —SO$_2$R, —SO$_2$N(R)$_2$, —C(O)N(R)$_2$, —NRC(O)R, or —NRSO$_2$R; or:

$R^2$ and $R^3$ are optionally taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur;

each R is independently hydrogen or an optionally substituted group selected from $C_{1-10}$ aliphatic, $C_{1-10}$ heteroalkyl having 1-3 heteroatoms independently selected from nitrogen, oxygen or sulfur, phenyl, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; or:

two R groups are optionally taken together with the intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen or sulfur;

$R^4$ is optionally substituted 5-14 membered heteroaryl having 1-4 heteroatoms independently selected from nitrogen, oxygen or sulfur, wherein at least one heteroatom is nitrogen;

$R^5$ is —OAr$^a$;

Ar$^a$ is optionally substituted

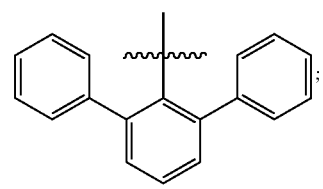 [SMILES: *c1c(-c2ccccc2)cccc1-c1ccccc1]

n is 0-2; and each $R^8$ is independently a phosphorus-containing ligand, wherein the phosphorus-containing ligand is bonded to W through a phosphorus atom.

In some embodiments, the present invention provides a compound of formula II-a:

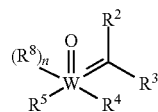

II

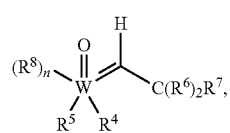

II-a wherein:
R⁴ is optionally substituted 5-14 membered heteroaryl having 1-4 heteroatoms independently selected from nitrogen, oxygen or sulfur, wherein at least one heteroatom is nitrogen;
R⁵ is —OAr^a;
Ar^a is optionally substituted

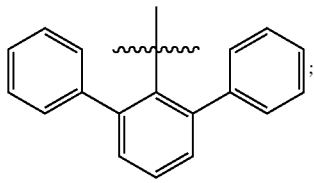 [SMILES: *c1c(-c2ccccc2)cccc1-c1ccccc1]

each R⁶ is independently —R, —OR, —SR, —N(R)₂, —OC(O)R, —S(O)R, —SO₂R, —SO₂N(R)₂, —C(O)N(R)₂, —NRC(O)R, or —NRSO₂R;
each R is independently hydrogen or an optionally substituted group selected from $C_{1-10}$ aliphatic, $C_{1-10}$ heteroalkyl having 1-3 heteroatoms independently selected from nitrogen, oxygen or sulfur, phenyl, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; or:
  two R groups are optionally taken together with the intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen or sulfur;
R⁷ is optionally substituted phenyl;
n is 0-2; and
each R⁸ is independently a phosphorus-containing ligand, wherein the phosphorus-containing ligand is bonded to W through a phosphorus atom.

In some embodiments, the present invention provides a compound of formula III:

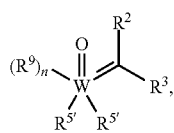

wherein:
each of R² and R³ is independently —R, —OR, —SR, —N(R)₂, —OC(O)R, —S(O)R, —SO₂R, —SO₂N(R)₂, —C(O)N(R)₂, —NRC(O)R, or —NRSO₂R; or:
R² and R³ are optionally taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur;
each R is independently hydrogen or an optionally substituted group selected from $C_{1-10}$ aliphatic, $C_{1-10}$ heteroalkyl having 1-3 heteroatoms independently selected from nitrogen, oxygen or sulfur, phenyl, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; or:
  two R groups are optionally taken together with the intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen or sulfur;
each R⁵' is independently —OAr^b;
Ar^b is

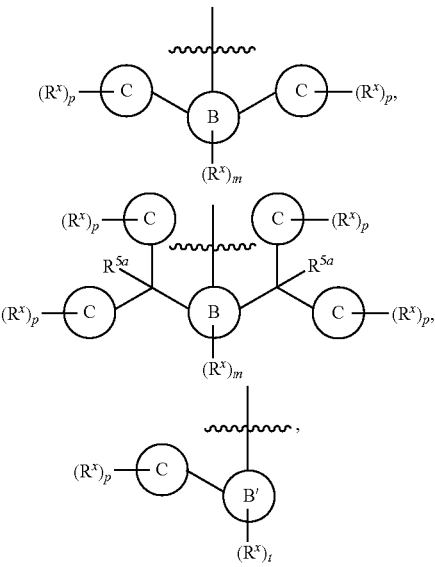

or an optionally substituted group selected from phenyl, a 10-14 membered bicyclic or polycyclic aryl ring, a 5-6 membered monocyclic heteroaryl ring having 1-4 heteroatoms independently selected from nitrogen, oxygen or sulfur, or an 8-14 membered bicyclic or polycyclic heteroaryl ring having 1-5 heteroatoms independently selected from nitrogen, oxygen or sulfur;
Ring B is an optionally substituted group selected from phenyl or a 5-6 membered monocyclic heteroaryl ring having 1-4 heteroatoms independently selected from nitrogen, oxygen or sulfur;
Ring B' is an optionally substituted group selected from phenyl, a 10-14 membered bicyclic or tricyclic aryl ring, a 5-6 membered monocyclic heteroaryl ring having 1-4 heteroatoms independently selected from nitrogen, oxygen or sulfur, or an 8-14 membered bicyclic or tricyclic heteroaryl ring having 1-5 heteroatoms independently selected from nitrogen, oxygen or sulfur;

each Ring C is independently an optionally substituted group selected from phenyl, a 3-7 membered saturated or partially unsaturated carbocyclic ring, an 6-14 membered bicyclic or tricyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-14 membered bicyclic or tricyclic heteroaryl ring having 1-5 heteroatoms independently selected from nitrogen, oxygen or sulfur;

each $R^x$ is independently R, halogen, —CN, —C(O)R, —C(O)OR, —C(O)N(R)$_2$, —C(O)N(R)(OR), —OR, —OC(O)R, —OC(O)N(R)$_2$, —OSi(R)$_3$, —SR, —S(O)R, —S(O)$_2$R, —S(O)$_2$OR, —S(O)$_2$N(R)$_2$, —NO$_2$, —N(R)$_2$, —NROR, —NRC(O)R, —N(R)C(O)OR, —N(R)C(O)N(R)$_2$, —N(R)S(O)$_2$R, —N(R)S(O)$_2$N(R)$_2$, —P(R)$_2$, —P(OR)$_2$, —P(O)(R)$_2$, —P(O)(OR)$_2$, —P(O)[N(R)$_2$]$_2$, or —Si(R)$_3$;

each $R^{5a}$ is independently R;
each of p and t is independently 0-7;
m is 0-3;
n is 0-2; and
each $R^g$ is independently a neutral ligand.

In some embodiments, the present invention provides a method for improving syndioselectivity of ROMP.

In some embodiments, the present invention provides a method for accelerating ROMP, wherein syndioselectivity of a polymer formed from the ROMP is not decreased.

2. Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "cycloaliphatic," as used herein, refers to saturated or partially unsaturated cyclic aliphatic monocyclic, bicyclic, or polycyclic ring systems, as described herein, having from 3 to 14 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic," may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, a cycloalkyl ring has from about 3-10 carbon atoms in their ring structure where such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which one or more carbon atoms is replaced with a heteroatom (e.g., oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more nonaromatic rings, such as indanyl, phthalimidyl, naphthimidyl, phenanthridinyl, or tetrahydronaphthyl, and the like.

The terms "heteroaryl" and "heteroar," used alone or as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 π electrons shared in a cyclic array; and having, in addition to carbon atoms, from one to five heteroatoms. The term "heteroatom" refers to nitrogen, oxygen or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H quinolizinyl, carbazolyl, acridinyl, phenazinyl, phenothiazinyl, phenoxazinyl, tetrahydroquinolinyl, tetrahydroisoquinolinyl, and pyrido[2,3b]-1,4-oxazin-3(4H)-one. A heteroaryl group may be mono or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5 to 7 membered monocyclic or 7-10 membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

The term "halogen" means F, Cl, Br, or I.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$Ph, which may be substituted with R°; (CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —OSiR°$_3$;

—($C_{1-4}$ straight or branched)alkylene)O—N(R°)$_2$; or —($C_{1-4}$ straight or branched)alkylene)C(O)O—N(R°)$_2$, wherein each R° may be substituted as defined below and is independently hydrogen, $C_{1-6}$ aliphatic, —CH$_2$Ph, —O(CH$_2$)$_{0-1}$Ph, —CH$_2$-(5-6 membered heteroaryl ring), or a 5-6 membered saturated, partially unsaturated, or aryl ring having 0-4 heteroatoms independently selected from nitrogen, oxygen or sulfur, or, notwithstanding the definition above, two independent occurrences of R°, taken together with their intervening atom(s), form a 3-12 membered saturated, partially unsaturated, or aryl mono- or bicyclic ring having 0-4 heteroatoms independently selected from nitrogen, oxygen or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from $C_{1-4}$ aliphatic, —CH$_2$Ph, —O(CH$_2$)$_{0-1}$Ph, or a 5-6 membered saturated, partially unsaturated, or aryl ring having 0-4 heteroatoms independently selected from nitrogen, oxygen or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6 membered saturated, partially unsaturated, or aryl ring having 0-4 heteroatoms independently selected from nitrogen, oxygen or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6 membered saturated, partially unsaturated, or aryl ring having 0-4 heteroatoms independently selected from nitrogen, oxygen or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, $C_{1-6}$ aliphatic which may be substituted as defined below, unsubstituted —OPh, or an unsubstituted 5-6 membered saturated, partially unsaturated, or aryl ring having 0-4 heteroatoms independently selected from nitrogen, oxygen or sulfur, or, notwithstanding the definition above, two independent occurrences of R$^\dagger$, taken together with their intervening atom(s) form an unsubstituted 3-12 membered saturated, partially unsaturated, or aryl mono- or bicyclic ring having 0-4 heteroatoms independently selected from nitrogen, oxygen or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6 membered saturated, partially unsaturated, or aryl ring having 0-4 heteroatoms independently selected from nitrogen, oxygen or sulfur.

As used herein, the term "stereogenic metal atom" is given its ordinary meaning, and refers to a metal atom coordinated by at least two ligands (e.g., at least four ligands), wherein the ligands are arranged about the metal atom such that the overall structure (e.g., metal complex) lacks a plane of symmetry with respect to the metal atom. In some cases, the stereogenic metal atom may be coordinated by at least three ligands, at least four ligands, at least five ligands, at least six ligands, or more. In certain embodiments, the stereogenic metal atom may be coordinated by four ligands. Metal complexes comprising a stereogenic metal center may provide sufficient space specificity at a reaction site of the metal complex, such that a molecular substrate having a plane of symmetry may be reacted at the reaction site to form a product that is free of a plane of symmetry. That is, the stereogenic metal center of the metal complex may impart sufficient shape specificity to induce stereogenicity effectively, producing a chiral product. Such metal complexes may exhibit improved catalytic activity and stereoselectivity, relative to previous systems, and may reduce undesired side reactions (e.g., dimerization or oligomerization of the metal complex).

The term "chiral" is given its ordinary meaning in the art and refers to a molecule that is not superimposable with its mirror image, wherein the resulting nonsuperimposable mirror images are known as "enantiomers" and are labeled as either an (R) enantiomer or an (S) enantiomer. Typically, chiral molecules lack a plane of symmetry.

The term "achiral" is given its ordinary meaning in the art and refers to a molecule that is superimposable with its mirror image. Typically, achiral molecules possess a plane of symmetry.

As used herein, a ligand may be either monodentate or polydentate. In some embodiments, a ligand is monodentate. In some embodiments, a ligand is bidentate. In some embodiments, a ligand is tridentate. In some embodiments, two or more monodentate ligands are taken together to form a polydentate ligand. A ligand may have hapticity of more than one. In some cases, a ligand has a hapticity of 1 to 10. In some embodiments, a ligand has a hapticity of 1. In some embodiments, a ligand has a hapticity of 2. In some embodiments, a ligand has a hapticity of 3. In some embodiments, a ligand has a hapticity of 4. In some embodiments, a ligand has a hapticity of 5. In some embodiments, a ligand has a hapticity of 6. For a ligand having hapticity greater than one, as sometimes done in the art, a single bond may be drawn between the ligand and the metal. In some cases, a ligand is alkylidene. In some cases, a ligand is a nitrogen-containing ligand. In some cases, a ligand is an oxygen-containing ligand. In some cases, a ligand is a phosphorus-containing ligand. In some embodiments, a ligand comprises an unsaturated bond, and the unsaturated bond is coordinated to a metal. In some embodiments, a ligand comprises a carbon-carbon double bond, and the double bond is coordinated to a metal. In some embodiments, a ligand is an olefin. When an olefin double bond is coordinated to a metal, the chemical bonding between the olefin and the metal can either be depicted as a 3-membered ring wherein the ring members comprises the metal and both carbon atoms of the double bond, or as a single bond between the metal and the double bond.

As used herein, a "nitrogen-containing ligand" may be any species comprising a nitrogen atom. In some cases, the nitrogen atom may bind to the metal atom. In some cases, the nitrogen-containing ligand may bind the metal center via a different atom. In some cases, the nitrogen atom may be a ring atom of a heteroaryl or heteroalkyl group. In some cases, the nitrogen atom may be a substituted amine group. It should be understood that, in catalyst precursors described herein, the nitrogen-containing ligand may have sufficiently ionic character to coordinate a metal center, such as a Mo or W metal center. Examples of nitrogen-containing ligands include, but are not limited to, pyrrolyl, pyrazolyl, pyridinyl, pyrazinyl, pyrimidinyl, imidazolyl, triazolyl, tetrazolyl, oxazolyl, isoxazolyl, thiazolyl, isothiazolyl, indolyl, indazolyl, carbazolyl, morpholinyl, piperidinyl, oxazinyl, substituted derivatives thereof, and the like. For example, the nitrogen-containing ligand may be pyrrolide or 2,5-dimethylpyrrolide. The nitrogen-containing ligand may be selected to interact with an oxygen-containing ligand such that the oxygen-containing ligand can readily replace the nitrogen-containing ligand in a precatalyst to generate a catalyst. In cases where the catalyst composition may be generated in situ in order to carry out a chemical reaction, the first, nitrogen-containing ligand may be selected such that, upon replacement by an oxygen-containing ligand, the nitrogen-containing ligands or protonated versions thereof do not interfere with the chemical reaction. In some embodiments, the nitrogen-containing ligand may be chiral and the precatalyst may be provided as a racemic mixture or a purified stereoisomer.

In some embodiments, a nitrogen-containing ligand may also describe a ligand precursor comprising at least one hydrogen atom directly bonded to a nitrogen atom, wherein deprotonation of the at least one hydrogen atom results in a negatively charged nitrogen atom, which may coordinate to a metal atom. Exemplary such precursors include but are not limited to amines, amides, and pyrrole and its derivatives thereof. A nitrogen-containing ligand may be a heteroaryl or heteroalkyl group comprising at least one nitrogen ring atom. In some cases, the nitrogen atom may be positioned on a substituent of an alkyl, heteroalkyl, aryl, or heteroaryl group. For example, a nitrogen-containing ligand may be an amine- or amide-substituted aryl group, wherein the amine or amide group is deprotonated upon coordination to the metal center.

As used herein, the term "oxygen-containing ligand" may be used to refer to ligands comprising at least one oxygen atom. In some cases, the oxygen atom binds to the metal atom thereby forming an ether-linkage. In other cases, the oxygen-containing ligand may bind the metal center via a different atom. The term "oxygen-containing ligand" may also describe ligand precursors comprising at least one hydroxyl group (e.g., a hydroxyl-containing ligand), wherein deprotonation of the hydroxyl group results in a negatively charged oxygen atom, which may coordinate to a metal atom. The oxygen-containing ligand may be a heteroaryl or heteroalkyl group comprising at least one oxygen ring atom. In some cases, the oxygen atom may be positioned on a substituent of an alkyl, heteroalkyl, aryl, or heteroaryl group. For example, the oxygen-containing ligand may be a hydroxy-substituted aryl group, wherein the hydroxyl group is deprotonated upon coordination to the metal center.

In some embodiments, an oxygen-containing ligand may also describe a ligand precursor comprising at least one hydroxyl group (e.g., a hydroxyl-containing ligand), wherein deprotonation of the hydroxyl group results in a negatively charged oxygen atom, which may coordinate to a metal atom. An oxygen-containing ligand may be a heteroaryl or heteroalkyl group comprising at least one oxygen ring atom. In some cases, the oxygen atom may be positioned on a substituent of an alkyl, heteroalkyl, aryl, or heteroaryl group. For example, an oxygen-containing ligand may be a hydroxy-substituted aryl group, wherein the hydroxyl group is deprotonated upon coordination to the metal center.

As used herein, the term "phosphorus-containing ligand" may be used to refer to ligands comprising at least one phosphorus atom. In some cases, the phosphorus atom binds to the metal. In other cases, the phosphorus-containing ligand may bind to the metal center via a different atom (i.e., an atom other than the phosphorous). The phosphorus-containing ligand may have phosphorus atom of various oxidation states. In some cases the phosphorus-containing ligand is phosphine. In some cases the phosphorus-containing ligand is phosphite. In some cases the phosphorus-containing ligand is phosphate. The phosphorus-containing ligand may be either monodentate or polydentate. In some cases, two or more phosphorus atoms bind to the metal. In some cases, one or more phosphorus atoms together with one or more non-phosphorus atoms bind to the metal.

The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Protected hydroxyl groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Examples of suitably protected hydroxyl groups further include, but are not limited to, esters, carbonates, sulfonates, allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, 0-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxycarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5] azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention unless specified otherwise.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}C$- or $^{13}C$- or $^{14}C$-enriched carbon are within the scope of this invention. Such compounds are useful, for example, as analytical tools or probes in biological assays.

As used herein and in the claims, the singular forms "a", "an", and "the" include the plural reference unless the context clearly indicates otherwise. Thus, for example, a reference to "a compound" includes a plurality of such compounds.

3. Description of Certain Embodiments of the Invention

In some embodiments, the present invention provides polymers with unprecedented stereoregularity. In some embodiments, the present invention provides poly(DCPD) with high stereoregularity.

In some embodiments, the present invention provides highly syndiotactic poly(DCPD). In some embodiments, a highly syndiotactic poly(DCPD) is greater than 80%, 81%, 82%, 83%, 84%, 85%, 86%, 87%, 88%, 89%, 90%, 91%, 92%, 93%, 94%, 95%, 96%, 97%, 98%, 99% or 99.5% syndiotactic.

In some embodiments, a highly syndiotactic poly(DCPD) is greater than 80% syndiotactic. In some embodiments, a highly syndiotactic poly(DCPD) is greater than 81% syndiotactic. In some embodiments, a highly syndiotactic poly(DCPD) is greater than 82% syndiotactic. In some embodiments, a highly syndiotactic poly(DCPD) is greater than 83% syndiotactic. In some embodiments, a highly syndiotactic poly(DCPD) is greater than 84% syndiotactic. In some embodiments, a highly syndiotactic poly(DCPD) is greater than 85% syndiotactic. In some embodiments, a highly syndiotactic poly(DCPD) is greater than 86% syndiotactic. In some embodiments, a highly syndiotactic poly(DCPD) is greater than 87% syndiotactic. In some embodiments, a highly syndiotactic poly(DCPD) is greater than 88% syndiotactic. In some embodiments, a highly syndiotactic poly(DCPD) is greater than 89% syndiotactic. In some embodiments, a highly syndiotactic poly(DCPD) is greater than 90% syndiotactic. In some embodiments, a highly syndiotactic poly(DCPD) is greater than 91% syndiotactic. In some embodiments, a highly syndiotactic poly(DCPD) is greater than 92% syndiotactic. In some embodiments, a highly syndiotactic poly(DCPD) is greater than 93% syndiotactic. In some embodiments, a highly syndiotactic poly(DCPD) is greater than 94% syndiotactic. In some embodiments, a highly syndiotactic poly(DCPD) is greater than 95% syndiotactic. In some embodiments, a highly syndiotactic poly(DCPD) is greater than 96% syndiotactic. In some embodiments, a highly syndiotactic poly(DCPD) is greater than 97% syndiotactic. In some embodiments, a highly syndiotactic poly(DCPD) is greater than 98% syndiotactic. In some embodiments, a highly syndiotactic poly(DCPD) is greater than 99% syndiotactic. In some embodiments, a highly syndiotactic poly(DCPD) is greater than 99.5% syndiotactic.

In some embodiments, a highly syndiotactic poly(DCPD) is 100% syndiotactic. In some embodiments, syndiotacticity of a provided poly(DCPD) is determined by nuclear magnetic resonance spectroscopy ("NMR"). In some embodiments, syndiotacticity of a provided poly(DCPD) is determined by $^{13}$C NMR.

In some embodiments, double bonds in the backbone of a poly(DCPD) is greater than 50%, 60%, 70%, 80%, 90%, 91%, 92%, 93%, 94%, 95%, 96%, 97%, 98%, 99% or 99.5% cis. In some embodiments, double bonds in the backbone of a poly(DCPD) is greater than 50% cis. In some embodiments, double bonds in the backbone of a provided poly (DCPD) is greater than 60% cis. In some embodiments, double bonds in the backbone of a provided poly(DCPD) is greater than 70% cis. In some embodiments, double bonds in the backbone of a provided poly(DCPD) is greater than 80% cis. In some embodiments, double bonds in the backbone of a provided poly(DCPD) is greater than 90% cis. In some embodiments, double bonds in the backbone of a provided poly(DCPD) is greater than 91% cis. In some embodiments, double bonds in the backbone of a provided poly(DCPD) is greater than 92% cis. In some embodiments, double bonds in the backbone of a provided poly(DCPD) is greater than 93% cis. In some embodiments, double bonds in the backbone of a provided poly(DCPD) is greater than 94% cis. In some embodiments, double bonds in the backbone of a provided poly(DCPD) is greater than 95% cis. In some embodiments, double bonds in the backbone of a provided poly(DCPD) is greater than 96% cis. In some embodiments, double bonds in the backbone of a provided poly(DCPD) is greater than 97% cis. In some embodiments, double bonds in the backbone of a provided poly(DCPD) is greater than 98% cis. In some embodiments, double bonds in the backbone of a provided poly(DCPD) is greater than 99% cis. In some embodiments, double bonds in the backbone of a provided poly(DCPD) is greater than 99.5% cis. In some embodiments, double bonds in the backbone of a provided poly(DCPD) is 100% cis.

In some embodiments, a provided poly(DCPD) is cis, syndiotactic. In some embodiments, a provided poly(DCPD) is greater than 80% syndiotactic, and the double bonds in the polymer backbone are greater than 50%, 60%, 70%, 80%, 90%, 91%, 92%, 93%, 94%, 95%, 96%, 97%, 98% or 99% cis. In some embodiments, a provided poly(DCPD) is greater than 80% syndiotactic, and the double bonds in the polymer backbone are greater than 80% cis. In some embodiments, a provided poly(DCPD) is greater than 80% syndiotactic, and the double bonds in the polymer backbone are greater than 90% cis. In some embodiments, a provided poly(DCPD) is greater than 80% syndiotactic, and the double bonds in the polymer backbone are greater than 95% cis.

In some embodiments, a provided poly(DCPD) is greater than 85% syndiotactic, and the double bonds in the polymer backbone are greater than 50%, 60%, 70%, 80%, 90%, 91%, 92%, 93%, 94%, 95%, 96%, 97%, 98% or 99% cis. In some embodiments, a provided poly(DCPD) is greater than 85% syndiotactic, and the double bonds in the polymer backbone are greater than 80% cis. In some embodiments, a provided poly(DCPD) is greater than 85% syndiotactic, and the double bonds in the polymer backbone are greater than 90% cis. In some embodiments, a provided poly(DCPD) is greater than 85% syndiotactic, and the double bonds in the polymer backbone are greater than 95% cis.

In some embodiments, a provided poly(DCPD) is greater than 90% syndiotactic, and the double bonds in the polymer backbone are greater than 50%, 60%, 70%, 80%, 90%, 91%, 92%, 93%, 94%, 95%, 96%, 97%, 98% or 99% cis. In some embodiments, a provided poly(DCPD) is greater than 90% syndiotactic, and the double bonds in the polymer backbone are greater than 80% cis. In some embodiments, a provided poly(DCPD) is greater than 90% syndiotactic, and the double bonds in the polymer backbone are greater than 90% cis. In some embodiments, a provided poly(DCPD) is greater than 90% syndiotactic, and the double bonds in the polymer backbone are greater than 95% cis.

In some embodiments, a provided poly(DCPD) is greater than 91% syndiotactic, and the double bonds in the polymer backbone are greater than 50%, 60%, 70%, 80%, 90%, 91%, 92%, 93%, 94%, 95%, 96%, 97%, 98% or 99% cis. In some embodiments, a provided poly(DCPD) is greater than 91% syndiotactic, and the double bonds in the polymer backbone are greater than 80% cis. In some embodiments, a provided poly(DCPD) is greater than 91% syndiotactic, and the double bonds in the polymer backbone are greater than 90% cis. In some embodiments, a provided poly(DCPD) is greater than 91% syndiotactic, and the double bonds in the polymer backbone are greater than 95% cis.

In some embodiments, a provided poly(DCPD) is greater than 92% syndiotactic, and the double bonds in the polymer backbone are greater than 50%, 60%, 70%, 80%, 90%, 91%, 92%, 93%, 94%, 95%, 96%, 97%, 98% or 99% cis. In some embodiments, a provided poly(DCPD) is greater than 92% syndiotactic, and the double bonds in the polymer backbone are greater than 80% cis. In some embodiments, a provided poly(DCPD) is greater than 92% syndiotactic, and the double bonds in the polymer backbone are greater than 90% cis. In some embodiments, a provided poly(DCPD) is greater than 92% syndiotactic, and the double bonds in the polymer backbone are greater than 95% cis.

In some embodiments, a provided poly(DCPD) is greater than 93% syndiotactic, and the double bonds in the polymer backbone are greater than 50%, 60%, 70%, 80%, 90%, 91%, 92%, 93%, 94%, 95%, 96%, 97%, 98% or 99% cis. In some embodiments, a provided poly(DCPD) is greater than 93% syndiotactic, and the double bonds in the polymer backbone are greater than 80% cis. In some embodiments, a provided poly(DCPD) is greater than 93% syndiotactic, and the double bonds in the polymer backbone are greater than 90% cis. In some embodiments, a provided poly(DCPD) is greater than 93% syndiotactic, and the double bonds in the polymer backbone are greater than 95% cis.

In some embodiments, a provided poly(DCPD) is greater than 94% syndiotactic, and the double bonds in the polymer backbone are greater than 50%, 60%, 70%, 80%, 90%, 91%, 92%, 93%, 94%, 95%, 96%, 97%, 98% or 99% cis. In some embodiments, a provided poly(DCPD) is greater than 94% syndiotactic, and the double bonds in the polymer backbone are greater than 80% cis. In some embodiments, a provided poly(DCPD) is greater than 94% syndiotactic, and the double bonds in the polymer backbone are greater than 90% cis. In some embodiments, a provided poly(DCPD) is greater than 94% syndiotactic, and the double bonds in the polymer backbone are greater than 95% cis.

In some embodiments, a provided poly(DCPD) is greater than 95% syndiotactic, and the double bonds in the polymer backbone are greater than 50%, 60%, 70%, 80%, 90%, 91%, 92%, 93%, 94%, 95%, 96%, 97%, 98% or 99% cis. In some embodiments, a provided poly(DCPD) is greater than 95% syndiotactic, and the double bonds in the polymer backbone are greater than 80% cis. In some embodiments, a provided poly(DCPD) is greater than 95% syndiotactic, and the double bonds in the polymer backbone are greater than 90% cis. In some embodiments, a provided poly(DCPD) is greater than 95% syndiotactic, and the double bonds in the polymer backbone are greater than 95% cis.

In some embodiments, a provided poly(DCPD) is greater than 96% syndiotactic, and the double bonds in the polymer backbone are greater than 50%, 60%, 70%, 80%, 90%, 91%, 92%, 93%, 94%, 95%, 96%, 97%, 98% or 99% cis. In some embodiments, a provided poly(DCPD) is greater than 96% syndiotactic, and the double bonds in the polymer backbone are greater than 80% cis. In some embodiments, a provided poly(DCPD) is greater than 96% syndiotactic, and the double bonds in the polymer backbone are greater than 90% cis. In some embodiments, a provided poly(DCPD) is greater than 96% syndiotactic, and the double bonds in the polymer backbone are greater than 95% cis.

In some embodiments, a provided poly(DCPD) is greater than 97% syndiotactic, and the double bonds in the polymer backbone are greater than 50%, 60%, 70%, 80%, 90%, 91%, 92%, 93%, 94%, 95%, 96%, 97%, 98% or 99% cis. In some embodiments, a provided poly(DCPD) is greater than 97% syndiotactic, and the double bonds in the polymer backbone are greater than 80% cis. In some embodiments, a provided poly(DCPD) is greater than 97% syndiotactic, and the double bonds in the polymer backbone are greater than 90% cis. In some embodiments, a provided poly(DCPD) is greater than 97% syndiotactic, and the double bonds in the polymer backbone are greater than 95% cis.

In some embodiments, a provided poly(DCPD) is greater than 98% syndiotactic, and the double bonds in the polymer backbone are greater than 50%, 60%, 70%, 80%, 90%, 91%, 92%, 93%, 94%, 95%, 96%, 97%, 98% or 99% cis. In some embodiments, a provided poly(DCPD) is greater than 98% syndiotactic, and the double bonds in the polymer backbone are greater than 80% cis. In some embodiments, a provided poly(DCPD) is greater than 98% syndiotactic, and the double bonds in the polymer backbone are greater than 90% cis. In some embodiments, a provided poly(DCPD) is greater than 98% syndiotactic, and the double bonds in the polymer backbone are greater than 95% cis.

In some embodiments, a provided poly(DCPD) is greater than 99% syndiotactic, and the double bonds in the polymer backbone are greater than 50%, 60%, 70%, 80%, 90%, 91%, 92%, 93%, 94%, 95%, 96%, 97%, 98% or 99% cis. In some embodiments, a provided poly(DCPD) is greater than 99% syndiotactic, and the double bonds in the polymer backbone are greater than 80% cis. In some embodiments, a provided poly(DCPD) is greater than 99% syndiotactic, and the double bonds in the polymer backbone are greater than 90% cis. In some embodiments, a provided poly(DCPD) is greater than 99% syndiotactic, and the double bonds in the polymer backbone are greater than 95% cis.

In some embodiments, a provided poly(DCPD) is 100% syndiotactic, and the double bonds in the polymer backbone are 100% cis.

In some embodiments, the present invention provides highly syndiotactic hydrogenated poly(DCPD). In some embodiments, a highly syndiotactic hydrogenated poly(DCPD) is greater than 80%, 81%, 82%, 83%, 84%, 85%, 86%, 87%, 88%, 89%, 90%, 91%, 92%, 93%, 94%, 95%, 96%, 97%, 98%, 99% or 99.5% syndiotactic. In some embodiments, a highly syndiotactic hydrogenated poly(DCPD) is greater than 80% syndiotactic. In some embodiments, a highly syndiotactic hydrogenated poly(DCPD) is greater than 81% syndiotactic. In some embodiments, a highly syndiotactic hydrogenated poly(DCPD) is greater than 82% syndiotactic. In some embodiments, a highly syndiotactic hydrogenated poly(DCPD) is greater than 83% syndiotactic. In some embodiments, a highly syndiotactic hydrogenated poly(DCPD) is greater than 84% syndiotactic. In some embodiments, a highly syndiotactic hydrogenated poly(DCPD) is greater than 85% syndiotactic. In some embodiments, a highly syndiotactic hydrogenated poly(DCPD) is greater than 86% syndiotactic. In some embodiments, a highly syndiotactic hydrogenated poly(DCPD) is greater than 87% syndiotactic. In some embodiments, a highly syndiotactic hydrogenated poly(DCPD) is greater than 88% syndiotactic. In some embodiments, a highly syndiotactic hydrogenated poly(DCPD) is greater than 89% syndiotactic. In some embodiments, a highly syndiotactic hydrogenated poly(DCPD) is greater than 90% syndiotactic. In some embodiments, a highly syndiotactic hydrogenated poly(DCPD) is greater than 91% syndiotactic. In some embodiments, a highly syndiotactic hydrogenated poly(DCPD) is greater than 92% syndiotactic. In some embodiments, a highly syndiotactic hydrogenated poly(DCPD) is greater than 93% syndiotactic. In some embodiments, a highly syndiotactic hydrogenated poly(DCPD) is greater than 94% syndiotactic. In some embodiments, a highly syndiotactic hydrogenated poly(DCPD) is greater than 95% syndiotactic. In some embodiments, a highly syndiotactic hydrogenated poly(DCPD) is greater than 96% syndiotactic. In some embodiments, a highly syndiotactic hydrogenated poly(DCPD) is greater than 97% syndiotactic. In some embodiments, a highly syndiotactic hydrogenated poly(DCPD) is greater than 98% syndiotactic. In some embodiments, a highly syndiotactic hydrogenated poly(DCPD) is greater than 99% syndiotactic. In some embodiments, a highly syndiotactic hydrogenated poly(DCPD) is greater than 99.5% syndiotactic. In some embodiments, a highly syndiotactic hydrogenated poly(DCPD) is 100% syndiotactic. In some embodiments, syndiotacticity of a provided hydrogenated poly(DCPD) is determined by nuclear magnetic resonance spectroscopy ("NMR"). In some embodiments, syndiotacticity of a provided hydrogenated poly(DCPD) is determined by $^{13}$C NMR.

In some embodiments, a hydrogenated poly(DCPD) is fully hydrogenated. In some embodiments, a hydrogenated poly(DCPD) is partially hydrogenated. In some embodiments, a hydrogenated poly(DCPD) is about 10%, about 20%, about 30%, about 40%, about 50%, about 60%, about 70%, about 80%, about 90%, about 91%, about 92%, about 93%, about 94%, about 95%, about 96%, about 97%, about 98%, about 99% or about 99.5% hydrogenated. In some embodiments, a hydrogenated poly(DCPD) is about 10% hydrogenated (about 10% of the double bonds are hydrogenated). In some embodiments, a hydrogenated poly(DCPD) is about 20% hydrogenated. In some embodiments, a hydrogenated poly(DCPD) is about 30% hydrogenated. In some embodiments, a hydrogenated poly(DCPD) is about 40% hydrogenated. In some embodiments, a hydrogenated poly(DCPD) is about 50% hydrogenated. In some embodiments, a hydrogenated poly(DCPD) is about 60% hydrogenated. In some embodiments, a hydrogenated poly(DCPD) is about 70% hydrogenated. In some embodiments, a hydrogenated poly(DCPD) is 80% hydrogenated. In some embodiments, a hydrogenated poly(DCPD) is about 90% hydrogenated. In some embodiments, a hydrogenated poly(DCPD) is about 95% hydrogenated. In some embodiments, a hydrogenated poly(DCPD) is about 99% hydrogenated. In some embodiments, a hydrogenated poly(DCPD) is greater than about 10%, about 20%, about 30%, about 40%, about 50%, about 60%, about 70%, about 80%, about 90%, about 91%, about 92%, about 93%, about 94%, about 95%, about 96%, about 97%, about 98%, about 99% or about 99.5% hydrogenated. In some embodiments, a hydrogenated poly (DCPD) is greater than about 10% hydrogenated. In some embodiments, a hydrogenated poly(DCPD) is greater than about 20% hydrogenated. In some embodiments, a hydrogenated poly(DCPD) is greater than about 30% hydrogenated. In some embodiments, a hydrogenated poly(DCPD) is greater than about 40% hydrogenated. In some embodiments, a hydrogenated poly(DCPD) is greater than about 50% hydrogenated. In some embodiments, a hydrogenated poly(DCPD) is greater than about 60% hydrogenated. In some embodiments, a hydrogenated poly(DCPD) is greater than about 70% hydrogenated. In some embodiments, a hydrogenated poly(DCPD) is greater than about 80% hydrogenated. In some embodiments, a hydrogenated poly(DCPD) is greater than about 90% hydrogenated. In some embodiments, a hydrogenated poly(DCPD) is greater than about 95% hydrogenated. In some embodiments, a hydrogenated poly(DCPD) is greater than about 99% hydrogenated.

In some embodiments, a provided polymer, for example, poly(DCPD) or hydrogenated poly(DCPD), has a molecular weight, $M_n$, greater than about 1,000. In some embodiments, a provided polymer has an $M_n$ greater than about 2,000. In some embodiments, a provided polymer has an $M_n$ greater than about 3,000. In some embodiments, a provided polymer has an $M_n$ greater than about 4,000. In some embodiments, a provided polymer has an $M_n$ greater than about 5,000. In some embodiments, a provided polymer has an $M_n$ greater than about 6,000. In some embodiments, a provided polymer has an $M_n$ greater than about 7,000. In some embodiments, a provided polymer has an $M_n$ greater than about 8,000. In some embodiments, a provided polymer has an $M_n$ greater than about 9,000. In some embodiments, a provided polymer has an $M_n$ greater than about 10,000. In some embodiments, a provided polymer has an $M_n$ greater than about 11,000. In some embodiments, a provided polymer has an $M_n$ greater than about 12,000. In some embodiments, a provided polymer has an $M_n$ greater than about 13,000. In some embodiments, a provided polymer has an $M_n$ greater than about 14,000. In some embodiments, a provided polymer has an $M_n$ greater than about 15,000. In some embodiments, a provided polymer has an $M_n$ greater than about 16,000. In some embodiments, a provided polymer has an $M_n$ greater than about 17,000. In some embodiments, a provided polymer has an $M_n$ greater than about 18,000. In some embodiments, a provided polymer has an $M_n$ greater than about 19,000. In some embodiments, a provided polymer has an $M_n$ greater than about 20,000. In some embodiments, a provided polymer has an $M_n$ greater than about 21,000. In some embodiments, a provided polymer has an $M_n$ greater than about 22,000. In some embodiments, a provided polymer has an $M_n$ greater than about 23,000. In some embodiments, a provided polymer has an $M_n$ greater than about 24,000. In some embodiments, a provided polymer has an $M_n$ greater than about 25,000. In some embodiments, a provided polymer has an $M_n$ greater than about 26,000. In some embodiments, a provided polymer has an $M_n$ greater than about 27,000. In some embodiments, a provided polymer has an $M_n$ greater than about 28,000. In some embodiments, a provided polymer has an $M_n$ greater than about 29,000. In some embodiments, a provided polymer has an $M_n$ greater than about 30,000. In some embodiments, a provided polymer has an $M_n$ greater than about 35,000. In some embodiments, a provided polymer has an $M_n$ greater than about 40,000. In some embodiments, a provided polymer has an $M_n$ greater than about 45,000. In some embodiments, a provided polymer has an $M_n$ greater than about 50,000. In some embodiments, a provided polymer has an $M_n$ greater than about 55,000. In some embodiments, a provided polymer has an $M_n$ greater than about 60,000. In some embodiments, a provided polymer has an $M_n$ greater than about 65,000. In some embodiments, a provided polymer has an $M_n$ greater than about 70,000. In some embodiments, a provided polymer has an $M_n$ greater than about 80,000. In some embodiments, a provided polymer has an $M_n$ greater than about 90,000. In some embodiments, a provided polymer has an $M_n$ greater than about 100,000.

In some embodiments, a provided poly(DCPD) is linear. In some embodiments, a provided poly(DCPD) is not crosslinked. In some embodiments, a provided poly(DCPD) is crosslinked. In some embodiments, a provided hydrogenated poly(DCPD) is linear. In some embodiments, a provided hydrogenated poly(DCPD) is not crosslinked. In some embodiments, a provided hydrogenated poly(DCPD) is crosslinked.

In some embodiments, dicyclopentadiene is endo-dicyclopentadiene.

In some embodiments, the present invention provides a composition, comprising highly syndiotactic poly(DCPD). In some embodiments, the present invention provides a composition, comprising highly syndiotactic hydrogenated poly(DCPD). In some embodiments, a provided composition further comprises a tungsten salt, a compound having the structure of $R^4$—H, a compound having the structure of $R^5$—H, a compound having the structure of $R^{5'}$—H, or one of more neutral ligands independently selected from $R^8$ or $R^9$. In some embodiments, a provided composition further comprises a tungsten salt, a compound having the structure of $R^4$—H, a compound having the structure of $R^5$—H, or one of more neutral ligands independently selected from $R^8$ or $R^9$. In some embodiments, a provided composition further comprises a tungsten salt, a compound having the structure of $R^4$—H, or a compound having the structure of $R^5$—H. In some embodiments, a provided composition further comprises a tungsten salt, a compound having the structure of $R^{5'}$—H, or one of more neutral ligands independently selected from $R^8$ or $R^9$. In some embodiments, a provided composition further comprise a tungsten salt. In some embodiments, a tungsten salt has the structure of formula I. In some embodiments, a tungsten salt has the structure of formula II. In some embodiments, a tungsten salt has the structure of formula III. In some embodiments, ROMP is quenched after a certain reaction time. In some embodiments, a tungsten salt is a quenched product of a compound of formula I, II or III. In some embodiments, a tungsten salt is a quenched product of a compound of formula I. In some embodiments, a tungsten salt is a quenched product of a compound of formula II. In some embodiments, a tungsten salt is a quenched product of a compound of formula III. In some embodiments, a provided compound further comprises a compound having the structure of $R^{5'}$—H. In some embodiments, a provided compound further comprises a compound having the structure of $R^5$—H. In some embodiments, a provided composition further comprises one of more neutral ligands independently selected from $R^8$ or $R^9$. In some embodiments, a provided composition further comprises a compound having the structure of $R^4$—H. In some embodiments, a provided composition further comprises a compound having the structure of $R^5$—H. In some embodiments, a provided composition further comprises a tungsten salt, a compound having the structure of $R^4$—H, and a compound having the structure of $R^5$—H.

In some embodiments, the present invention provides a method for preparing a highly syndiotactic poly(DCPD), comprising providing a compound of formula I:

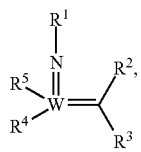

I wherein each variable is independently as defined above and described herein.

In some embodiments, the present invention provides a method for preparing a highly syndiotactic poly(DCPD), comprising providing a compound of formula II:

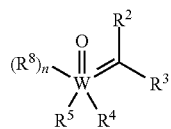

II wherein each variable is independently as defined above and described herein. In some embodiments, the present invention provides a method for preparing highly syndiotactic hydrogenated poly(DCPD), comprising providing a compound of formula III:

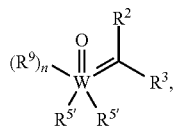

III wherein each variable is independently as defined above and described herein. In some embodiments, the present invention provides a method for preparing highly syndiotactic hydrogenated poly(DCPD), comprising providing a compound of formula III and a Lewis acid. In some embodiments, a provided Lewis acid comprises boron. In some embodiments, a provided Lewis acid has the structure of $B(R)_3$. In some embodiments, a provided Lewis acid is $B(C_6F_5)_3$.

In some embodiments, a provided method further comprises polymerizing dicyclopentadiene in the presence a provided compound of formula I. In some embodiments, a provided method further comprises polymerizing dicyclopentadiene in the presence a provided compound of formula II. In some embodiments, a provided method further comprises polymerizing dicyclopentadiene in the presence a provided compound of formula III. In some embodiments, a provided method further comprises polymerizing dicyclopentadiene in the presence a provided compound of formula III and a Lewis acid. In some embodiments, a provided Lewis acid comprises boron. In some embodiments, a provided Lewis acid has the structure of $B(R)_3$. In some embodiments, a provided method further comprises polymerizing dicyclopentadiene in the presence a provided compound of formula III and a compound having the structure of $B(R)_3$, wherein each R is independently as defined above and described herein. In some embodiments, a provided method further comprises polymerizing dicyclopentadiene in the presence a provided compound of formula III and a compound having the structure of $B(C_6F_5)_3$.

In some embodiments, the present invention provides a method of preparing a highly syndiotactic poly(DCPD), comprising steps of:

a) providing a compound of formula I:

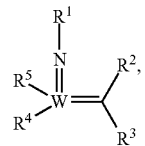

I wherein each variable is independently as defined above and described herein;

b) providing dicyclopentadiene; and c) polymerizing the provided dicyclopentadiene in the presence of a provided compound of formula I to provide highly syndiotactic poly(DCPD).

In some embodiments, the present invention provides a method of preparing a highly syndiotactic poly(DCPD), comprising steps of:

a) providing a compound of formula II:

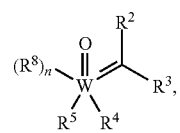

II wherein each variable is independently as defined above and described herein;

b) providing dicyclopentadiene; and c) polymerizing the provided dicyclopentadiene in the presence of a provided compound of formula II to provide highly syndiotactic poly(DCPD).

In some embodiments, the present invention provides a method of preparing a highly syndiotactic poly(DCPD), comprising steps of:

a) providing a compound of formula III:

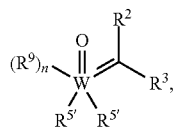

III wherein each variable is independently as defined above and described herein;

b) providing dicyclopentadiene; and c) polymerizing the provided dicyclopentadiene in the presence of a provided compound of formula III to provide highly syndiotactic poly(DCPD).

In some embodiments, the present invention provides a method of preparing a highly syndiotactic poly(DCPD), comprising steps of:

a) providing a compound of formula III:

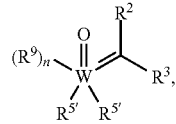

wherein each variable is independently as defined above and described herein;

b) providing a Lewis acid;

c) providing dicyclopentadiene; and d) polymerizing the provided dicyclopentadiene in the presence of the provided compound of formula III and the Lewis acid to provide highly syndiotactic poly(DCPD).

In some embodiments, the present invention provides a method of preparing a highly syndiotactic poly(DCPD), comprising steps of:

a) providing a compound of formula III:

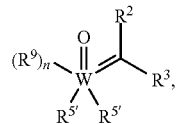

wherein each variable is independently as defined above and described herein;

b) providing a compound having the structure of $B(R)_3$;

c) providing dicyclopentadiene; and d) polymerizing the provided dicyclopentadiene in the presence of a provided compound of formula III and the compound having the structure of $B(R)_3$ to provide highly syndiotactic poly(DCPD).

In some embodiments, the present invention provides a method for preparing highly syndiotactic hydrogenated poly(DCPD), comprising providing a highly syndiotactic poly(DCPD). In some embodiments, the present invention provides a method for preparing highly syndiotactic hydrogenated poly(DCPD), comprising providing a compound of formula I:

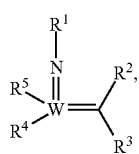

wherein each variable is independently as defined above and described herein. In some embodiments, the present invention provides a method for preparing highly syndiotactic hydrogenated poly(DCPD), comprising providing a compound of formula II:

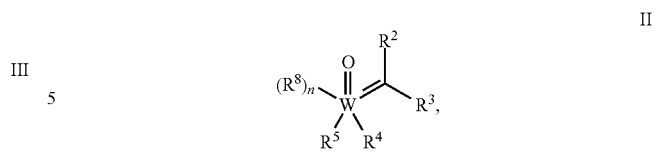

wherein each variable is independently as defined above and described herein. In some embodiments, the present invention provides a method for preparing highly syndiotactic hydrogenated poly(DCPD), comprising providing a compound of formula III:

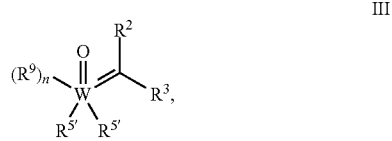

wherein each variable is independently as defined above and described herein. In some embodiments, the present invention provides a method for preparing highly syndiotactic hydrogenated poly(DCPD), comprising providing a compound of formula III and a Lewis acid. In some embodiments, a Lewis acid comprises boron. In some embodiments, a provided Lewis acid has the structure of $B(R)_3$. In some embodiments, a provided Lewis acid is $B(C_6F_5)_3$.

In some embodiments, the present invention provides a method of preparing highly syndiotactic hydrogenated poly (DCPD), comprising steps of:

a) providing a compound of formula I:

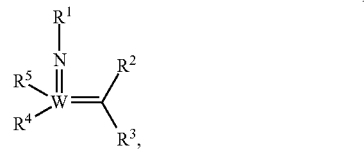

wherein each variable is independently as defined above and described herein;

b) providing dicyclopentadiene; and c) polymerizing the provided dicyclopentadiene in the presence of a provided compound of formula I to provide highly syndiotactic poly(DCPD).

In some embodiments, the present invention provides a method of preparing highly syndiotactic hydrogenated poly (DCPD), comprising steps of:

a) providing a compound of formula I:

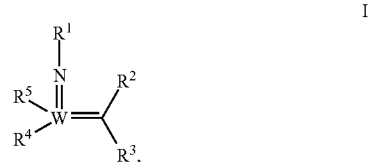

wherein each variable is independently as defined above and described herein;

b) providing dicyclopentadiene;
c) polymerizing the provided dicyclopentadiene in the presence of a provided compound of formula I to provide highly syndiotactic poly(DCPD); and
d) hydrogenate the provided highly syndiotactic poly (DCPD) to provide highly syndiotactic hydrogenated poly (DCPD).

In some embodiments, the present invention provides a method of preparing highly syndiotactic hydrogenated poly (DCPD), comprising steps of:
a) providing a compound of formula II:

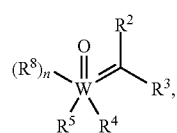

II wherein each variable is independently as defined above and described herein;
b) providing dicyclopentadiene; and
c) polymerizing the provided dicyclopentadiene in the presence of a provided compound of formula II to provide highly syndiotactic poly(DCPD).

In some embodiments, the present invention provides a method of preparing highly syndiotactic poly (DCPD), comprising steps of:
a) providing a compound of formula II:

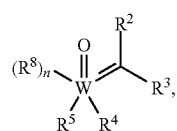

II wherein each variable is independently as defined above and described herein;
b) providing dicyclopentadiene;
c) polymerizing the provided dicyclopentadiene in the presence of a provided compound of formula II to provide highly syndiotactic poly(DCPD); and
d) hydrogenate the provided highly syndiotactic poly (DCPD) to provide highly syndiotactic hydrogenated poly (DCPD).

In some embodiments, the present invention provides a method of preparing a highly syndiotactic poly(DCPD), comprising steps of:
a) providing a compound of formula III:

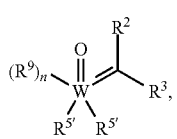

III wherein each variable is independently as defined above and described herein;
b) providing dicyclopentadiene;
c) polymerizing the provided dicyclopentadiene in the presence of a provided compound of formula III to provide highly syndiotactic poly(DCPD); and d) hydrogenate the provided highly syndiotactic poly (DCPD) to provide highly syndiotactic hydrogenated poly (DCPD).

In some embodiments, the present invention provides a method of preparing a highly syndiotactic poly(DCPD), comprising steps of:
a) providing a compound of formula III:

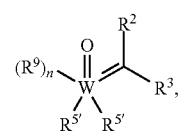

III wherein each variable is independently as defined above and described herein;
b) providing a Lewis acid;
c) providing dicyclopentadiene;
d) polymerizing the provided dicyclopentadiene in the presence of a provided compound of formula III and the provided Lewis acid to provide highly syndiotactic poly (DCPD); and
e) hydrogenate the provided highly syndiotactic poly (DCPD) to provide highly syndiotactic hydrogenated poly (DCPD).

In some embodiments, the present invention provides a method of preparing a highly syndiotactic poly(DCPD), comprising steps of:
a) providing a compound of formula III:

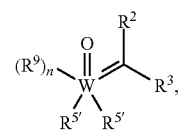

III wherein each variable is independently as defined above and described herein;
b) providing a compound having the structure of $B(R)_3$;
c) providing dicyclopentadiene;
d) polymerizing the provided dicyclopentadiene in the presence of a provided compound of formula III and the compound having the structure of $B(R)_3$ to provide highly syndiotactic poly(DCPD); and
e) hydrogenate the provided highly syndiotactic poly (DCPD) to provide highly syndiotactic hydrogenated poly (DCPD).

In some embodiments, doubles bonds in the backbone of a provided highly syndiotactic poly(DCPD) is largely cis. In some embodiments, the double bonds are greater than 50%, 60%, 70%, 80%, 90%, 91%, 92%, 93%, 94%, 95%, 96%, 97%, 98%, 99% or 99.5% cis. In some embodiments, the double bonds are greater than about 95% cis.

Exemplary hydrogenation methods are widely known in the art. In some embodiments, an exemplary method is catalytic hydrogenation. In some embodiments, an exemplary method is hydrogenation by diimine. In some embodiments, a diimine is generated in situ, for example, from p-toluenesulfonyl hydrazide (p-Tos-$NHNH_2$). Suitable solvents include, for example, chloroform and cyclohexane. In some embodiments, hydrogenation is performed at a temperature higher than room temperature. In some embodiments, hydrogenation is performed at about 100, 110, 120, 130, 140, 150, 160, 170, 180, 190 or 200° C. In some embodiments, hydrogenation is performed at greater than about 100, 110, 120, 130, 140, 150, 160, 170, 180, 190 or 200° C. In some embodiments, hydrogenation is conducted under high pressure. In some embodiments, hydrogenation is conducted at about 1.0 M Pa.

In some embodiments, polymerization of dicyclopentadiene is conducted through ring-opening metathesis polymerization (ROMP). In some embodiments, polymerization is promoted by a provided compound or a derivative thereof.

In some embodiments, the present invention provides a compound of formula I:

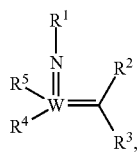

I wherein each variable is independently as defined above and described herein. In some embodiments, the present invention provides a compound of formula II:

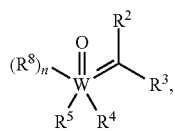

II wherein each variable is independently as defined above and described herein. In some embodiments, a compound of formula II has the structure of formula II-a:

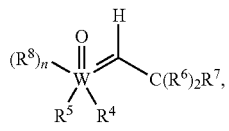

II-a wherein each variable is independently as defined above and described herein. In some embodiments, the present invention provides a compound of formula III:

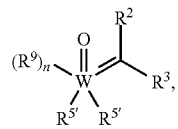

III wherein each variable is independently as defined above and described herein.

As generally defined above, $R^1$ is a tertiary group having the structure of —$C(R^{1a})_3$ wherein each $R^{1a}$ is independently as defined above and described herein. In some embodiments, $R^1$ is optionally substituted tertiary $C_{1-30}$ aliphatic. In some embodiments, $R^1$ is optionally substituted tertiary $C_{1-20}$ aliphatic. In some embodiments, $R^1$ is optionally substituted tertiary $C_{1-10}$ aliphatic. In some embodiments, $R^1$ is optionally substituted tertiary $C_{1-30}$ alkyl. In some embodiments, $R^1$ is optionally substituted tertiary $C_{1-20}$ alkyl. In some embodiments, $R^1$ is optionally substituted tertiary $C_{1-10}$ alkyl. In some embodiments, $R^1$ is optionally substituted tertiary $C_{1-6}$ alkyl. In some embodiments, $R^1$ is optionally substituted tertiary $C_{1-4}$ alkyl. In some embodiments, $R^1$ is t-butyl. In some embodiments, $R^1$ is other than t-butyl. In some embodiments, $R^1$ is adamantyl. In some embodiments, $R^1$ is other than adamantyl. In some embodiments, $R^1$ is other than t-butyl and adamantyl.

As generally defined above, each $R^{1a}$ is independently an optionally substituted group selected from $C_{1-10}$ aliphatic, $C_{1-10}$ heteroalkyl having 1-3 heteroatoms independently selected from nitrogen, oxygen or sulfur, phenyl, a 3-7 membered saturated or partially unsaturated carbocyclic ring, an 8-10 membered bicyclic or polycyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; or:

two $R^{1a}$ groups are optionally taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur; or:

three $R^{1a}$ groups are optionally taken together with the carbon atom to which they are attached to form an optionally substituted 4-10 membered, bicyclic or polycyclic, saturated or partially unsaturated ring having 0-4 heteroatoms independently selected from nitrogen, oxygen or sulfur.

In some embodiments, $R^{1a}$ is an optionally substituted group selected from $C_{1-10}$ aliphatic, $C_{1-10}$ heteroalkyl having 1-3 heteroatoms independently selected from nitrogen, oxygen or sulfur, phenyl, a 3-7 membered saturated or partially unsaturated carbocyclic ring, an 8-10 membered bicyclic or polycyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur.

In some embodiments, $R^{1a}$ is optionally substituted $C_{1-10}$ aliphatic. In some embodiments, $R^{1a}$ is optionally substituted $C_{3-10}$ cycloaliphatic. In some embodiments, $R^{1a}$ is optionally substituted $C_{1-6}$ aliphatic. In some embodiments, $R^{1a}$ is optionally substituted $C_{1-6}$ alkyl. In some embodiments, $R^{1a}$ is optionally substituted hexyl, pentyl, butyl, propyl, ethyl or methyl. In some embodiments, $R^{1a}$ is optionally substituted hexyl. In some embodiments, $R^{1a}$ is optionally substituted pentyl. In some embodiments, $R^{1a}$ is optionally substituted butyl. In some embodiments, $R^{1a}$ is optionally substituted propyl. In some embodiments, $R^{1a}$ is optionally substituted ethyl. In some embodiments, $R^{1a}$ is optionally substituted methyl. In some embodiments, $R^{1a}$ is hexyl. In some embodiments, $R^{1a}$ is pentyl. In some embodiments, $R^{1a}$ is butyl. In some embodiments, $R^{1a}$ is propyl. In some embodiments, $R^{1a}$ is ethyl. In some embodiments, $R^{1a}$ is methyl. In some embodiments, $R^{1a}$ is isopropyl.

In some embodiments, $R^{1a}$ is optionally substituted $C_{1-10}$ heteroalkyl having 1-3 heteroatoms independently selected from nitrogen, oxygen or sulfur. In some embodiments, $R^{1a}$ is optionally substituted $C_{1-6}$ heteroalkyl having 1-3 heteroatoms independently selected from nitrogen, oxygen or sulfur. In some embodiments, $R^{1a}$ is optionally substituted $C_{1-4}$ heteroalkyl having 1-3 heteroatoms independently selected from nitrogen, oxygen or sulfur.

In some embodiments, $R^{1a}$ is optionally substituted phenyl. In some embodiments, $R^{1a}$ is substituted phenyl. In some embodiments, $R^{1a}$ is unsubstituted phenyl.

In some embodiments, $R^{1a}$ is an optionally substituted 3-7 membered saturated or partially unsaturated carbocyclic ring. In some embodiments, $R^{1a}$ is an optionally substituted 3-7 membered saturated carbocyclic ring. In some embodiments, $R^{1a}$ is optionally substituted cycloheptyl. In some embodiments, $R^{1a}$ is cycloheptyl. In some embodiments, $R^{1a}$ is optionally substituted cyclohexyl. In some embodiments, $R^{1a}$ is cyclohexyl. In some embodiments, $R^{1a}$ is optionally substituted cyclopentyl. In some embodiments, $R^{1a}$ is cyclopentyl. In some embodiments, $R^{1a}$ is optionally substituted cyclobutyl. In some embodiments, $R^{1a}$ is cyclobutyl. In some embodiments, $R^{1a}$ is optionally substituted cyclopropyl. In some embodiments, $R^{1a}$ is cyclopropyl.

In some embodiments, $R^{1a}$ is an optionally substituted 8-10 membered bicyclic or polycyclic saturated, partially unsaturated or aryl ring. In some embodiments, $R^{1a}$ is an optionally substituted 8-10 membered bicyclic saturated, partially unsaturated or aryl ring. In some embodiments, $R^{1a}$ is an optionally substituted bicyclic or polycyclic 8-10 membered saturated carbocyclic ring.

In some embodiments, $R^{1a}$ is an optionally substituted 5-6 membered monocyclic heteroaryl ring having 1-4 heteroatoms independently selected from nitrogen, oxygen or sulfur. In some embodiments, $R^{1a}$ is an optionally substituted 5-membered monocyclic heteroaryl ring having 1-4 heteroatoms independently selected from nitrogen, oxygen or sulfur. In some embodiments, $R^{1a}$ is an optionally substituted 6-membered monocyclic heteroaryl ring having 1-4 heteroatoms independently selected from nitrogen, oxygen or sulfur.

In some embodiments, $R^{1a}$ is an optionally substituted 3-7 membered saturated or partially unsaturated heterocyclic ring having 1-3 heteroatoms independently selected from nitrogen, oxygen or sulfur. In some embodiments, $R^{1a}$ is an optionally substituted 7-10 membered bicyclic saturated or partially unsaturated heterocyclic ring having 1-5 heteroatoms independently selected from nitrogen, oxygen or sulfur. In some embodiments, $R^{1a}$ is an optionally substituted 8-10 membered bicyclic heteroaryl ring having 1-5 heteroatoms independently selected from nitrogen, oxygen or sulfur.

In some embodiments, two $R^{1a}$ groups are optionally taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur. It is understood by a person having ordinary skill in the art that when two $R^{1a}$ groups are taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur, $R^1$ has the structure of

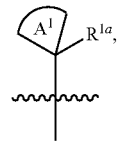

wherein Ring $A^1$ is an optionally substituted 3-10 membered, monocyclic, bicyclic or polycyclic, saturated or partially unsaturated ring having 0-4 heteroatoms independently selected from nitrogen, oxygen or sulfur, $R^{1a}$ is an optionally substituted group selected from $C_{1-10}$ aliphatic, $C_{1-10}$ heteroalkyl having 1-3 heteroatoms independently selected from nitrogen, oxygen or sulfur, phenyl, a 3-7 membered saturated or partially unsaturated carbocyclic ring, an 8-10 membered bicyclic or polycyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur.

In some embodiments, two $R^{1a}$ groups are taken together with the carbon atom to which they are attached to form an optionally substituted 3-10 membered monocyclic, bicyclic or polycyclic, saturated or partially unsaturated bivalent cycloaliphatic ring. In some embodiments, two $R^{1a}$ groups are taken together with the carbon atom to which they are attached to form an optionally substituted 3-10 membered monocyclic saturated or partially unsaturated bivalent cycloaliphatic ring. In some embodiments, two $R^{1a}$ groups are taken together with the carbon atom to which they are attached to form an optionally substituted 3-10 membered monocyclic saturated bivalent cycloaliphatic ring. In some embodiments, two $R^{1a}$ groups are taken together with the carbon atom to which they are attached to form an optionally substituted bivalent cyclopropyl ring (optionally substituted

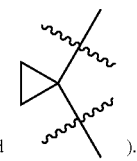

(optionally substituted ).

In some embodiments, two $R^{1a}$ groups are taken together with the carbon atom to which they are attached to form an optionally substituted bivalent cyclobutyl ring (optionally substituted

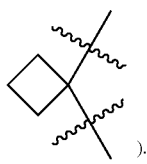

(optionally substituted ).

In some embodiments, two $R^{1a}$ groups are taken together with the carbon atom to which they are attached to form an optionally substituted bivalent cyclopentyl ring (optionally substituted

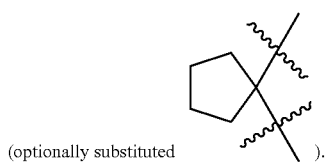 [SMILES: *C1(*)CCCC1]

(optionally substituted ).

In some embodiments, two $R^{1a}$ groups are taken together with the carbon atom to which they are attached to form an optionally substituted bivalent cyclohexyl ring (optionally substituted

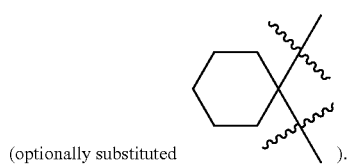 [SMILES: *C1(*)CCCCC1]

(optionally substituted ).

In some embodiments, two $R^{1a}$ groups are taken together with the carbon atom to which they are attached to form an optionally substituted bivalent cycloheptyl ring (optionally substituted

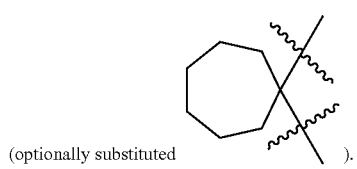 [SMILES: *C1(*)CCCCCC1]

(optionally substituted ).

In some embodiments, two $R^{1a}$ groups are taken together with the carbon atom to which they are attached to form an optionally substituted bivalent cyclooctyl ring (optionally substituted

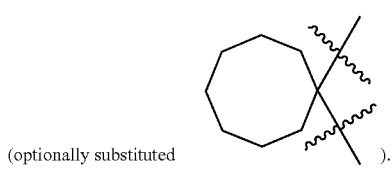 [SMILES: *C1(*)CCCCCCC1]

(optionally substituted ).

In some embodiments, two $R^{1a}$ groups are taken together with the carbon atom to which they are attached to form an optionally substituted 3-10 membered monocyclic partially unsaturated bivalent cycloaliphatic ring.

In some embodiments, two $R^{1a}$ groups are taken together with the carbon atom to which they are attached to form an optionally substituted 4-10 membered bicyclic saturated or partially unsaturated cycloaliphatic ring. In some embodiments, two $R^{1a}$ groups are taken together with the carbon atom to which they are attached to form an optionally substituted 4-10 membered bicyclic saturated cycloaliphatic ring. In some embodiments, two $R^{1a}$ groups are taken together with the carbon atom to which they are attached to form an optionally substituted 4-10 membered bicyclic partially unsaturated cycloaliphatic ring.

In some embodiments, two $R^{1a}$ groups are taken together with the carbon atom to which they are attached to form an optionally substituted 6-10 membered polycyclic saturated or partially unsaturated cycloaliphatic ring. In some embodiments, two $R^{1a}$ groups are taken together with the carbon atom to which they are attached to form an optionally substituted 6-10 membered polycyclic saturated cycloaliphatic ring. In some embodiments, two $R^{1a}$ groups are taken together with the carbon atom to which they are attached to form an optionally substituted 10-membered polycyclic saturated cycloaliphatic ring. In some embodiments, two $R^{1a}$ groups are taken together with the carbon atom to which they are attached to form an optionally substituted 10-membered tricyclic saturated cycloaliphatic ring. In some embodiments, two $R^{1a}$ groups are taken together with the carbon atom to which they are attached to form an optionally substituted

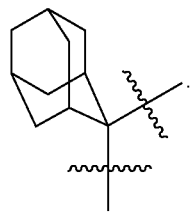 [SMILES: *C1(*)C2CC3CC(C2)CC1C3]

In some embodiments, two $R^{1a}$ groups are taken together with the carbon atom to which they are attached to form

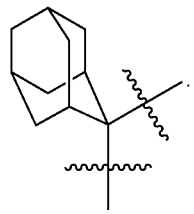 [SMILES: *C1(*)C2CC3CC(C2)CC1C3]

In some embodiments, two $R^{1a}$ groups are taken together with the carbon atom to which they are attached to form an optionally substituted 6-10 membered polycyclic partially unsaturated cycloaliphatic ring.

In some embodiments, two $R^{1a}$ groups are optionally taken together with the carbon atom to which they are attached to form an optionally substituted 3-10 membered, monocyclic, bicyclic or polycyclic, saturated or partially unsaturated ring having 1-4 heteroatoms independently selected from nitrogen, oxygen or sulfur.

In some embodiments, $R^1$ is —$C(R^{1a})_3$, wherein each $R^{1a}$ is independently optionally substituted $C_{1-10}$ aliphatic. In some embodiments, $R^1$ is —$C(R^{1a})_3$, wherein each $R^{1a}$ is independently optionally substituted $C_{1-10}$ alkyl. In some embodiments, $R^1$ is t-butyl. In some embodiments, $R^1$ is —$C(R^{1a})_3$, wherein two $R^{1a}$ is independently optionally substituted $C_{1-10}$ aliphatic, and the third $R^{1a}$ is optionally substituted phenyl. In some embodiments, $R^1$ is —C(CH$_3$)$_2$Ph. In some embodiments, $R^1$ is —C($R^{1a}$)$_3$, wherein each $R^{1a}$ is independently optionally substituted phenyl. In some embodiments, $R^1$ is —CPh$_3$. In some embodiments, $R^1$ is —C($R^{1a}$)$_3$, wherein two of the three $R^{1a}$ groups are taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur. In some embodiments, two of the $R^{1a}$ groups are taken together with the carbon atom to which they are attached to form optionally substituted cyclohexyl, and the third $R^{1a}$ is optionally substituted phenyl. In some embodiments, $R^1$ is

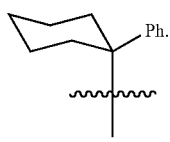 [SMILES: *C1(c2ccccc2)CCCCC1]

In some other embodiments, two of the $R^{1a}$ groups are taken together with the carbon atom to which they are attached to form optionally substituted secondary adamantyl, and the third $R^{1a}$ is optionally substituted phenyl. In some embodiments, $R^1$ is

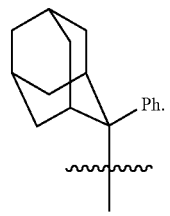 [SMILES: *C1(c2ccccc2)C2CC3CC(C2)CC1C3]

In some embodiments, $R^1$ is —C($R^{1a}$)$_3$, wherein three $R^{1a}$ groups are optionally taken together with the carbon atom to which they are attached to form an optionally substituted 4-10 membered, bicyclic or polycyclic, saturated or partially unsaturated ring having 0-4 heteroatoms independently selected from nitrogen, oxygen or sulfur. In some embodiments, three $R^{1a}$ groups are optionally taken together with the carbon atom to which they are attached to form an optionally substituted 4-9 membered, bicyclic or polycyclic, saturated or partially unsaturated ring having 0-4 heteroatoms independently selected from nitrogen, oxygen or sulfur. In some embodiments, $R^1$ is —C($R^{1a}$)$_3$, wherein three $R^{1a}$ groups are optionally taken together with the carbon atom to which they are attached to form an optionally substituted 4-10 membered, bicyclic or polycyclic, saturated or partially unsaturated carbocyclic ring. In some embodiments, $R^1$ is —C($R^{1a}$)$_3$, wherein three $R^{1a}$ groups are optionally taken together with the carbon atom to which they are attached to form an optionally substituted 4-10 membered, bicyclic or polycyclic, saturated carbocyclic ring. In some embodiments, $R^1$ is —C($R^{1a}$)$_3$, wherein three $R^{1a}$ groups are optionally taken together with the carbon atom to which they are attached to form an optionally substituted 6-10 membered, bicyclic or polycyclic, saturated carbocyclic ring. In some embodiments, $R^1$ is —C($R^{1a}$)$_3$, wherein three $R^{1a}$ groups are optionally taken together with the carbon atom to which they are attached to form an optionally substituted 8-10 membered, bicyclic or polycyclic, saturated carbocyclic ring. In some embodiments, $R^1$ is —C($R^{1a}$)$_3$, wherein three $R^{1a}$ groups are optionally taken together with the carbon atom to which they are attached to form an optionally substituted 8-membered, bicyclic or polycyclic, saturated carbocyclic ring. In some embodiments, $R^1$ is optionally substituted

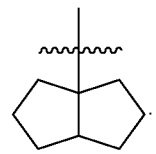 [SMILES: *C12CCCC1CCC2]

In some embodiments, $R^1$ is

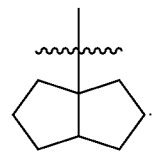

In some embodiments, $R^1$ is optionally substituted

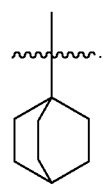 [SMILES: *C12CCC(CC1)CC2]

In some embodiments, $R^1$ is

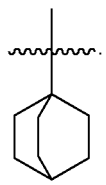

In some embodiments, $R^1$ is —C($R^{1a}$)$_3$, wherein three $R^{1a}$ groups are optionally taken together with the carbon atom to which they are attached to form an optionally substituted 10-membered, bicyclic or polycyclic, saturated carbocyclic ring. In some embodiments, $R^1$ is optionally substituted 1-adamantyl. In some embodiments, $R^1$ is

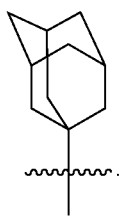

Exemplary R¹ groups are depicted below:

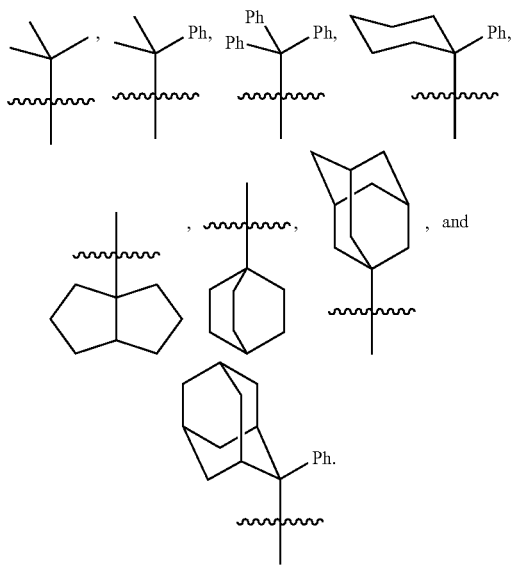

As defined generally above, each of R² and R³ is independently —R, —OR, —SR, —N(R)₂, —OC(O)R, —S(O)R, —SO₂R, —SO₂N(R)₂, —C(O)N(R)₂, —NRC(O)R, or —NRSO₂R, wherein each R is independently as defined above and described herein; or:

R² and R³ are optionally taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur.

In some embodiments, one of R² and R³ is hydrogen, and the other R² and R³ is R. In some embodiments, both R² and R³ are hydrogen. In some embodiments, one of R² and R³ is hydrogen and the other is an optionally substituted group selected from $C_{1-10}$ aliphatic, $C_{1-10}$ heteroalkyl, phenyl, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur, —OR, —SR, —N(R)₂, —OC(O)R, —SOR, —SO₂R, —SO₂N(R)₂, —C(O)N(R)₂, —NRC(O)R, or —NRSO₂R. In some embodiments, one of R² and R³ is hydrogen and the other is an optionally substituted group selected from $C_{1-10}$ aliphatic, $C_{1-10}$ heteroaliphatic, phenyl, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur. In some embodiments, one of R² and R³ is hydrogen and the other is an optionally substituted group selected from $C_{1-6}$ aliphatic, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur. In some embodiments, one of R² and R³ is hydrogen, and the other R² and R³ is optionally substituted $C_{1-6}$ alkyl. In some embodiments, one of R² and R³ is hydrogen, and the other R² and R³ is optionally methyl.

In certain embodiments, R² or R³ is optionally substituted $C_{1-6}$ aliphatic. In some embodiments, R² or R³ is optionally substituted $C_{1-6}$ alkyl. In certain embodiments, R² or R³ is $C_{1-6}$ alkyl substituted with phenyl and one or two additional substituents. In certain embodiments, R² or R³ is a lower alkyl group optionally substituted with one or two methyl groups and phenyl. In certain embodiments, R² or R³ is —C(Me)₂Ph. In certain embodiments, R² or R³ is —C(Me)₃.

In some embodiments, each of R² and R³ is independently R, wherein R is as defined above and described herein. In some embodiments, each of R² and R³ is independently R, wherein at least one of R² and R³ is not hydrogen.

In certain embodiments, R² is hydrogen and R³ is R, —OR, —SR, —N(R)₂, —OC(O)R, —SOR, —SO₂R, —SO₂N(R)₂, —C(O)N(R)₂, —NRC(O)R, or —NRSO₂R, wherein each R is independently as defined above and described herein. In certain embodiments, R² is hydrogen and R³ is R, wherein R is as defined above and described herein. In certain embodiments, R² is hydrogen and R³ is optionally substituted $C_{1-20}$ aliphatic. In some embodiments, R² is hydrogen and R³ is optionally substituted $C_{1-20}$ alkyl. In certain embodiments, R² is hydrogen and R³ is $C_{1-6}$ alkyl substituted with phenyl and one or two additional substituents. In certain embodiments, R² is hydrogen and R³ is a lower alkyl group optionally substituted with one or two methyl groups and phenyl. In certain embodiments, R² is hydrogen and R³ is —C(Me)₂Ph. In certain embodiments, R² is hydrogen and R³ is —C(Me)₃.

In some embodiments, R² and R³ are optionally taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur. In some embodiments, R² and R³ are optionally taken together with the carbon atom to which they are attached to form optionally substituted $C_{3-10}$ cycloalkylidene. In some embodiments, R² and R³ are optionally taken together with the carbon atom to which they are attached to form optionally substituted cyclopentylidene.

As generally defined above, R⁴ is optionally substituted 5-14 membered heteroaryl having 1-4 heteroatoms independently selected from nitrogen, oxygen or sulfur, wherein at least one heteroatom is nitrogen. In some embodiments, R⁴ is bonded to W through the at least one nitrogen atom. In some embodiments, R⁴ is optionally substituted 5-membered heteroaryl having 1-4 heteroatoms independently selected from nitrogen, oxygen or sulfur, wherein at least one heteroatom is nitrogen. In some embodiments, $R^4$ is optionally substituted

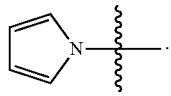

In some embodiments, $R^4$ is optionally substituted

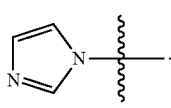

In some embodiments, $R^4$ is optionally substituted

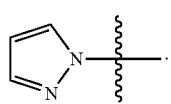 [SMILES: *n1cccn1]

In some embodiments, $R^4$ is optionally substituted

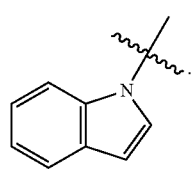 [SMILES: *n1ccc2ccccc21]

In some embodiments, $R^4$ is optionally substituted

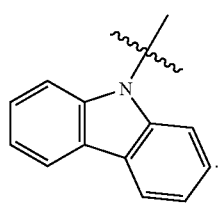 [SMILES: *n1c2ccccc2c2ccccc21]

In some embodiments, $R^4$ is

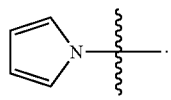

In some embodiments, $R^4$ is

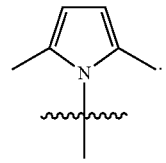

As generally defined above, $R^5$ is —OAr$^a$, wherein Ar$^a$ is optionally substituted

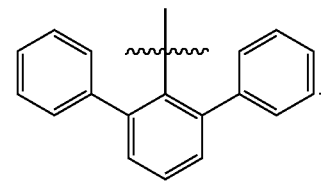 [SMILES: *c1c(-c2ccccc2)cccc1-c1ccccc1]

In some embodiments, $R^5$ is —OAr$^a$, wherein Ar$^a$ is substituted

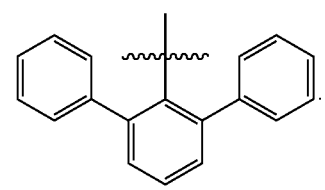 [SMILES: *c1c(-c2ccccc2)cccc1-c1ccccc1]

As generally defined above, Ar$^a$ is optionally substituted

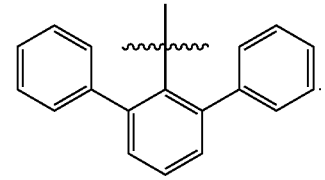 [SMILES: *c1c(-c2ccccc2)cccc1-c1ccccc1]

In some embodiments, Ar$^a$ is

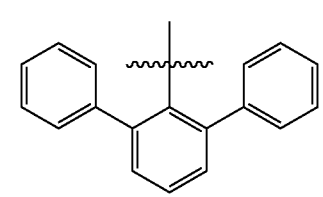 [SMILES: *c1c(-c2ccccc2)cccc1-c1ccccc1]

optionally substituted with one or more halogen or $C_{1-6}$ aliphatic, haloalkyl or heteroalkyl. In some embodiments, Ar$^a$ is

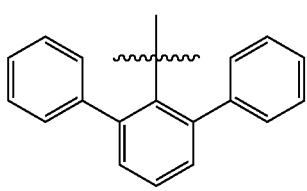 [SMILES: *c1c(-c2ccccc2)cccc1-c1ccccc1]

substituted with one or more halogen or C$_{1-6}$ aliphatic, haloalkyl or heteroalkyl. In some embodiments, Ar$^a$ is

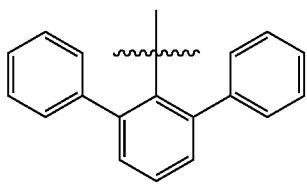 [SMILES: *c1c(-c2ccccc2)cccc1-c1ccccc1]

substituted with one or more halogen. In some embodiments, Ar$^a$ is

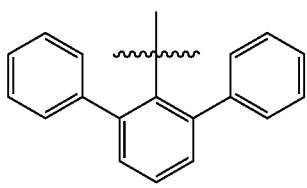 [SMILES: *c1c(-c2ccccc2)cccc1-c1ccccc1]

substituted with one or more C$_{1-6}$ aliphatic. In some embodiments, Ar$^a$ is

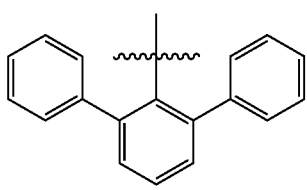 [SMILES: *c1c(-c2ccccc2)cccc1-c1ccccc1]

substituted with one or more C$_{1-6}$ alkyl. In some embodiments, each of the 2', 2", 6' and 6" positions is independently substituted

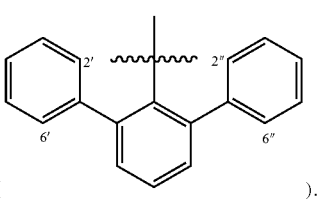

In some embodiments, Ar$^a$ is

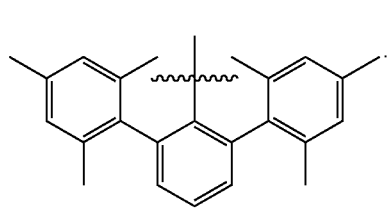

In some embodiments, Ar$^a$ is

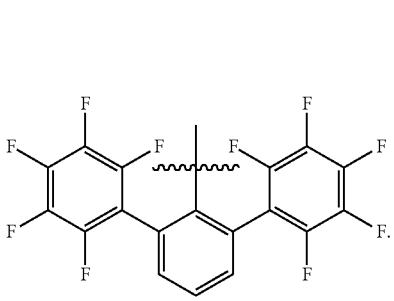

In some embodiments, R$^5$ is optionally substituted

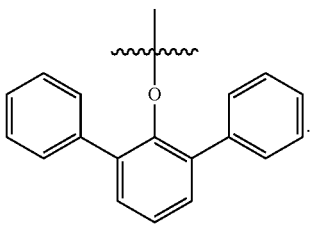 [SMILES: *Oc1c(-c2ccccc2)cccc1-c1ccccc1]

In some embodiments, R$^5$ is substituted

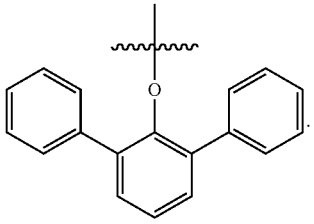 [SMILES: *Oc1c(-c2ccccc2)cccc1-c1ccccc1]

In some embodiments, each of the 2', 2", 6' and 6" positions is independently substituted

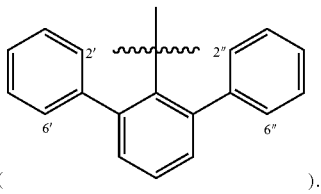

In some embodiments, $R^5$ is

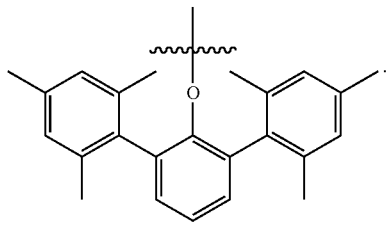

In some embodiments, $R^5$ is

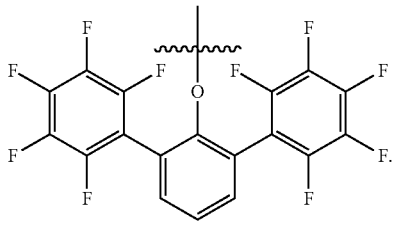 [SMILES: *Oc1c(-c2c(F)c(F)c(F)c(F)c2F)cccc1-c1c(F)c(F)c(F)c(F)c1F]

As generally defined above, each $R^{5'}$ is independently —$OAr^b$, wherein $Ar^b$ is as defined above and described herein. In some embodiments, each $R^{5'}$ is independently an aryloxy group, wherein the oxygen atom is bonded to an aromatic carbon atom of $Ar^b$.

As generally defined above, $Ar^b$ is

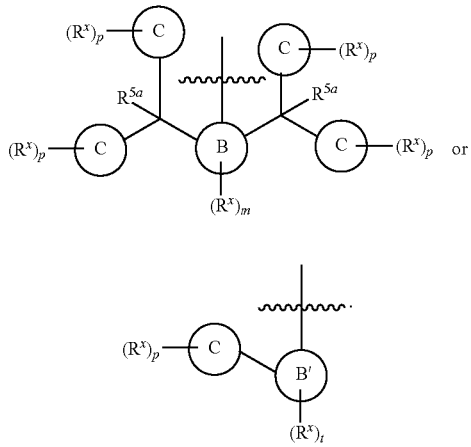

or an optionally substituted group selected from phenyl, a 10-14 membered bicyclic or polycyclic aryl ring, a 5-6 membered monocyclic heteroaryl ring having 1-4 heteroatoms independently selected from nitrogen, oxygen or sulfur, or an 8-14 membered bicyclic or polycyclic heteroaryl ring having 1-5 heteroatoms independently selected from nitrogen, oxygen or sulfur.

In some embodiments, $Ar^b$ is

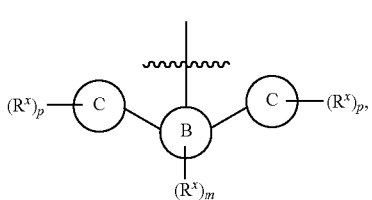

In some embodiments, $Ar^b$ is

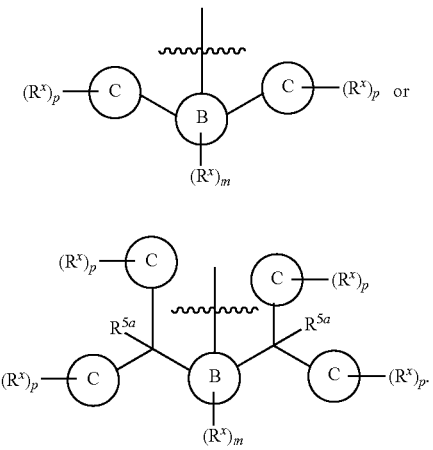

In some embodiments, $Ar^b$ is

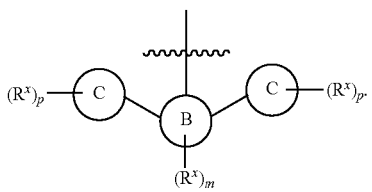

In some embodiments, $Ar^b$ is

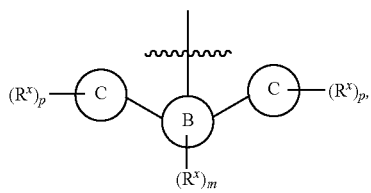

wherein each of Ring B and Ring C is independently optionally substituted phenyl. In some embodiments, $Ar^b$ is

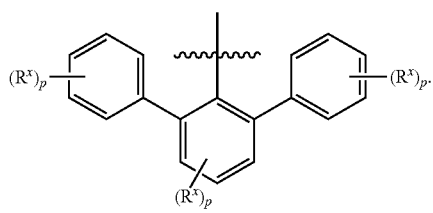

In some embodiments, $Ar^b$ is optionally substituted

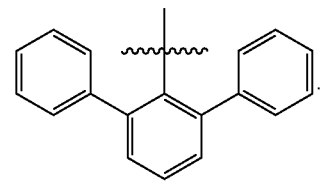 [SMILES: *c1c(-c2ccccc2)cccc1-c1ccccc1]

In some embodiments, $Ar^b$ is substituted

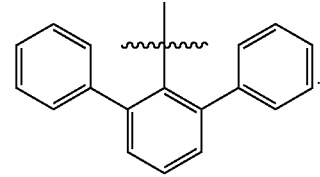 [SMILES: *c1c(-c2ccccc2)cccc1-c1ccccc1]

In some embodiments, each of the 2', 2", 6' and 6" positions is independently substituted

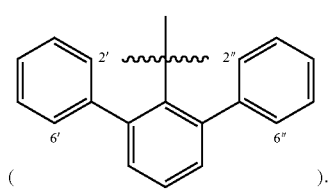 [SMILES: *c1c(-c2ccccc2)cccc1-c1ccccc1]

In some embodiments, $Ar^b$ is

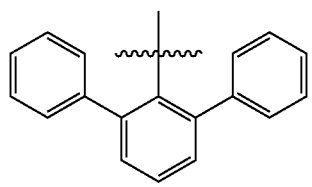 [SMILES: *c1c(-c2ccccc2)cccc1-c1ccccc1]

optionally substituted with one or more halogen or $C_{1-6}$ aliphatic, haloalkyl or heteroalkyl. In some embodiments, $Ar^b$ is

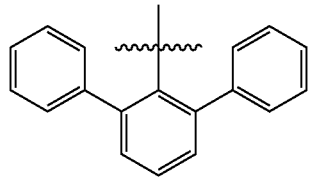 [SMILES: *c1c(-c2ccccc2)cccc1-c1ccccc1]

substituted with one or more halogen or $C_{1-6}$ alkyl. In some embodiments, $Ar^b$ is

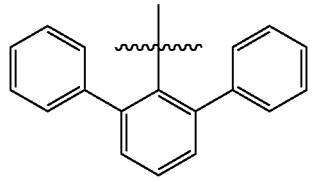 [SMILES: *c1c(-c2ccccc2)cccc1-c1ccccc1]

substituted with one or more halogen. In some embodiments, $Ar^b$ is substituted with one or more $C_{1-6}$ alkyl. In some embodiments, $Ar^b$ is

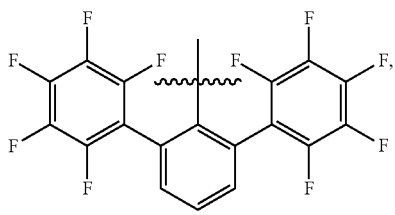

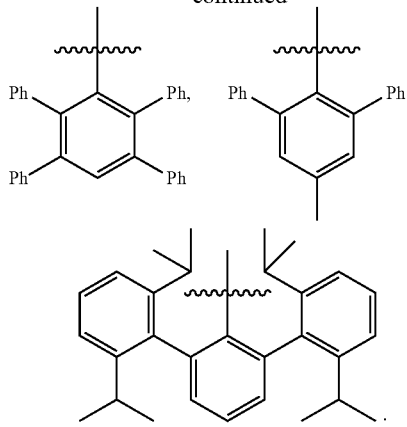

In some embodiments, Ar$^b$ is

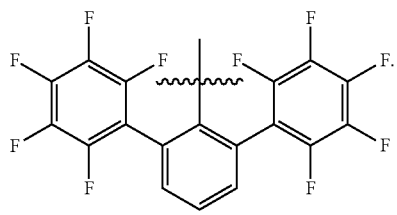 [SMILES: *c1c(-c2c(F)c(F)c(F)c(F)c2F)cccc1-c1c(F)c(F)c(F)c(F)c1F]

In some embodiments, Ar$^b$ is

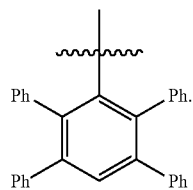

In some embodiments, Ar$^b$ is

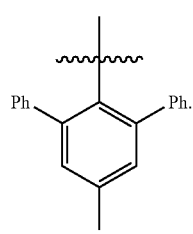

In some embodiments, Ar$^b$ is

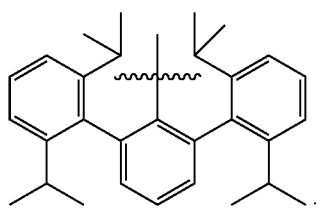 [SMILES: *c1c(-c2c(C(C)C)cccc2C(C)C)cccc1-c1c(C(C)C)cccc1C(C)C]

In some embodiments, Ar$^b$ is

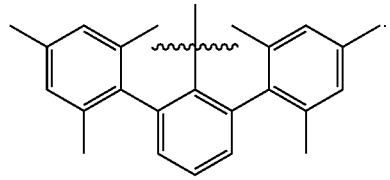

In some embodiments, Ar$^b$ is

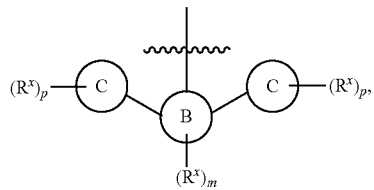

wherein Ring B is optionally substituted phenyl, and each Ring C is independently optionally substituted pyrrolyl. In some embodiments, Ar$^b$ is

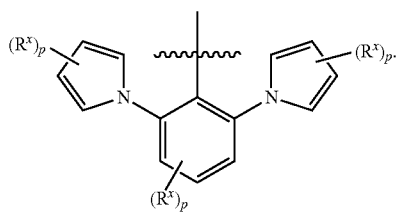

In some embodiments, Ar$^b$ is

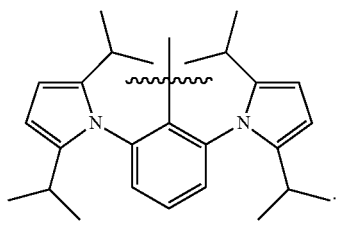 [SMILES: *c1c(-n2c(C(C)C)ccc2C(C)C)cccc1-n1c(C(C)C)ccc1C(C)C]

In some embodiments, Ar$^b$ is

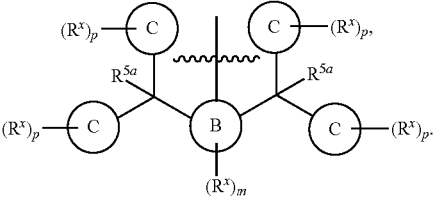

In some embodiments, $Ar^b$ is

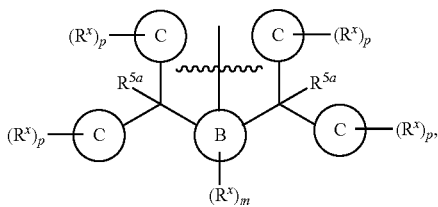

wherein each of Ring B and Ring C is independently optionally substituted phenyl. In some embodiments, $Ar^b$ is

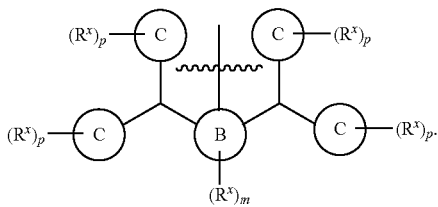

In some embodiments, $Ar^b$ is

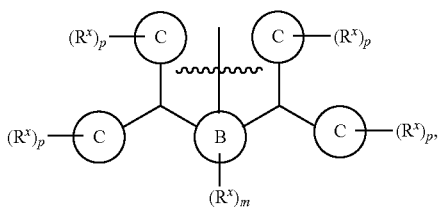

wherein each of Ring B and Ring C is independently optionally substituted phenyl. In some embodiments, $Ar^b$ is

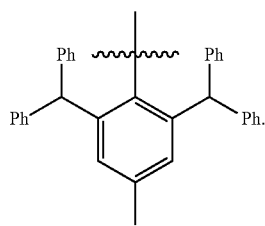 [SMILES: *c1c(C(c2ccccc2)c2ccccc2)cc(C)cc1C(c1ccccc1)c1ccccc1]

In some embodiments, $Ar^b$ is

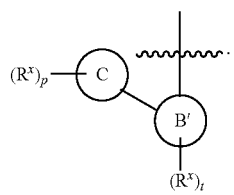

In some embodiments, $Ar^b$ is an optionally substituted group selected from phenyl, a 10-14 membered bicyclic or polycyclic aryl ring, a 5-6 membered monocyclic heteroaryl ring having 1-4 heteroatoms independently selected from nitrogen, oxygen or sulfur, or an 8-14 membered bicyclic or polycyclic heteroaryl ring having 1-5 heteroatoms independently selected from nitrogen, oxygen or sulfur.

In some embodiments, $Ar^b$ is optionally substituted phenyl. In some embodiments, $Ar^b$ is phenyl. In some embodiments, $Ar^b$ is substituted phenyl.

In some embodiments, $Ar^b$ is an optionally substituted 10-14 membered bicyclic or polycyclic aryl ring. In some embodiments, $Ar^b$ is R, wherein R is an optionally substituted 10-membered bicyclic aryl ring. In some embodiments, $Ar^b$ is an optionally substituted 14-membered tricyclic aryl ring. In some embodiments, $Ar^b$ is R, wherein R is an optionally substituted 5-6 membered monocyclic heteroaryl ring having 1-4 heteroatoms independently selected from nitrogen, oxygen or sulfur. In some embodiments, $Ar^b$ is an optionally substituted 8-14 membered bicyclic or polycyclic heteroaryl ring having 1-5 heteroatoms independently selected from nitrogen, oxygen or sulfur. In some embodiments, $Ar^b$ is R, wherein R is an optionally substituted 8-10 membered bicyclic heteroaryl ring having 1-5 heteroatoms independently selected from nitrogen, oxygen or sulfur. In some embodiments, $Ar^b$ is an optionally substituted tricyclic heteroaryl ring having 1-5 heteroatoms independently selected from nitrogen, oxygen or sulfur.

As generally defined above, Ring B is an optionally substituted group selected from phenyl or a 5-6 membered monocyclic heteroaryl ring having 1-4 heteroatoms independently selected from nitrogen, oxygen or sulfur. In some embodiments, Ring B is optionally substituted phenyl. In some embodiments, Ring B is an optionally substituted 5-6 membered monocyclic heteroaryl ring having 1-4 heteroatoms independently selected from nitrogen, oxygen or sulfur. In some embodiments, Ring B is an optionally substituted 5-membered heteroaryl ring having 1-4 heteroatoms independently selected from nitrogen, oxygen or sulfur. In some embodiments, Ring B is an optionally substituted 6-membered heteroaryl ring having 1-4 heteroatoms independently selected from nitrogen, oxygen or sulfur.

In some embodiments, Ring B has the structure of

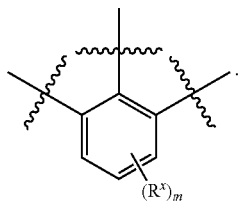

wherein each of $R^x$ and m is independently as defined above and described herein. In some embodiments, m=0. In some embodiments, Ring B is

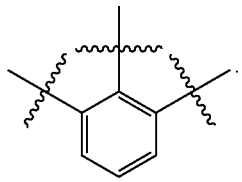 [SMILES: *c1cccc(*)c1*]

As generally defined above, Ring B' is an optionally substituted group selected from phenyl, a 10-14 membered bicyclic or tricyclic aryl ring, a 5-6 membered monocyclic heteroaryl ring having 1-4 heteroatoms independently selected from nitrogen, oxygen or sulfur, or an 8-14 membered bicyclic or tricyclic heteroaryl ring having 1-5 heteroatoms independently selected from nitrogen, oxygen or sulfur.

In some embodiments, Ring B' is substituted phenyl. In some embodiments, Ring B' is phenyl substituted with one or more optionally substituted $C_{1-4}$ aliphatic. In some embodiments, Ring B' is a 10-14 membered bicyclic or tricyclic aryl ring. In some embodiments, Ring B' is a 10-membered bicyclic aryl ring. In some embodiments, Ring B' is an optionally substituted group selected from:

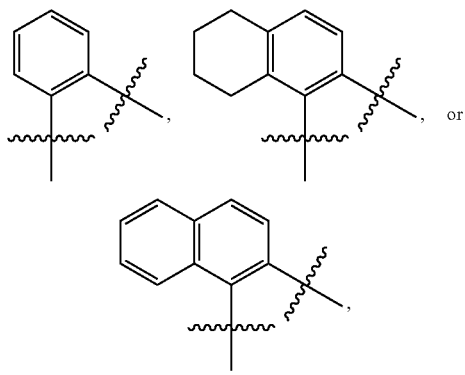

wherein each ⸹ independently represents the point of attachment to Ring C or oxygen, and Ring B' is optionally substituted with 0-7 $R^x$. In some embodiments, Ring B' has the structure of

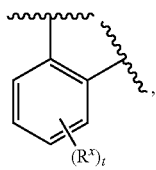

wherein each of $R^x$ and t is independently as defined above and described herein. In some embodiments, Ring B is optionally substituted

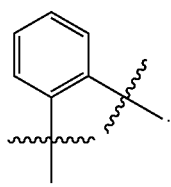 [SMILES: *c1ccccc1*]

In some embodiments, Ring B' is optionally substituted

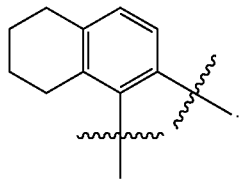 [SMILES: *c1ccc2c(c1*)CCCC2]

In some embodiments, Ring B' is optionally substituted

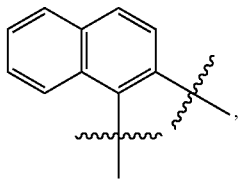 [SMILES: *c1ccc2ccccc2c1*]

In some embodiments, Ring B' is 14-membered tricyclic aryl ring. In some embodiments, Ring B' is an optionally substituted 8-14 membered bicyclic or tricyclic heteroaryl ring having 1-5 heteroatoms independently selected from nitrogen, oxygen or sulfur. In some embodiments, Ring B' is an optionally substituted 8-14 membered bicyclic heteroaryl ring having 1-5 heteroatoms independently selected from nitrogen, oxygen or sulfur. In some embodiments, Ring B' is an optionally substituted 8-14 membered tricyclic heteroaryl ring having 1-5 heteroatoms independently selected from nitrogen, oxygen or sulfur.

As generally defined above, each Ring C is independently an optionally substituted group selected from phenyl, a 3-7 membered saturated or partially unsaturated carbocyclic ring, an 6-14 membered bicyclic or tricyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-14 membered bicyclic or tricyclic heteroaryl ring having 1-5 heteroatoms independently selected from nitrogen, oxygen or sulfur.

In some embodiments, Ring C is optionally substituted phenyl. In some embodiments, Ring C is

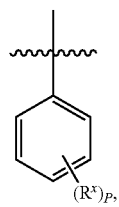

wherein each of $R^x$ and p is independently as defined above and described herein. In some embodiments, Ring C has the structure of

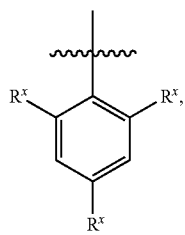

wherein each $R^x$ is independently as defined above and described herein. In some embodiments, Ring C has the structure of

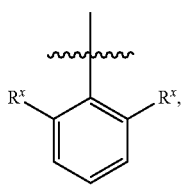

wherein each $R^x$ is independently as defined above and described herein. In some embodiments, Ring C is —$C_6F_5$, 2,6-diisopropylphenyl, 2,4,6-trimethylphenyl or 2,4,6-triisopropylphenyl.

In some embodiments, Ring C is an optionally substituted 3-7 membered saturated carbocyclic ring. In some embodiments, Ring C is an optionally substituted 5-6 membered saturated carbocyclic ring. In some embodiments, Ring C is an optionally substituted 3-7 membered partially unsaturated carbocyclic ring. In some embodiments, Ring C is an optionally substituted 5-6 membered partially unsaturated carbocyclic ring.

In some embodiments, Ring C is an optionally substituted 6-14 membered bicyclic or tricyclic saturated, partially unsaturated or aryl ring. In some embodiments, Ring C is R, wherein R is an optionally substituted 6-10 membered bicyclic saturated, partially unsaturated or aryl ring. In some embodiments, Ring C is an optionally substituted 8-14 membered bicyclic or tricyclic saturated carbocyclic ring. In some embodiments, Ring C is an optionally substituted 8-14 membered bicyclic or tricyclic partially unsaturated carbocyclic ring. In some embodiments, Ring C is an optionally substituted 10-membered bicyclic aryl ring. In some embodiments, Ring C is an optionally substituted 14-membered tricyclic aryl ring. In some embodiments, Ring C is optionally substituted

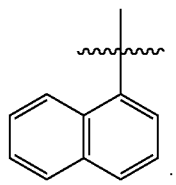 [SMILES: *c1cccc2ccccc12]

In some embodiments, Ring C is optionally substituted

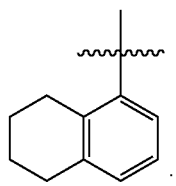 [SMILES: *c1cccc2c1CCCC2]

In some embodiments, Ring C is an optionally substituted 5-6 membered monocyclic heteroaryl ring having 1-4 heteroatoms independently selected from nitrogen, oxygen, or sulfur. In some embodiments, Ring C is an optionally substituted 5-6 membered monocyclic heteroaryl ring having 1-2 heteroatoms independently selected from nitrogen, oxygen, or sulfur. In some embodiments, Ring C is an optionally substituted 5-membered monocyclic heteroaryl ring having 1-4 heteroatoms independently selected from nitrogen, oxygen, or sulfur. In some embodiments, Ring C is optionally substituted 5-membered monocyclic heteroaryl ring having 1-4 nitrogen atoms. In some embodiments, Ring C is optionally substituted 5-membered monocyclic heteroaryl ring having 1-2 nitrogen atoms. In some embodiments, Ring C is

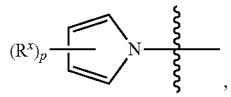

wherein $R^x$ is as defined above and described herein, and p is 0-4. In some embodiments, Ring C

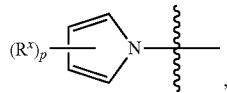

is wherein $R^x$ is optionally substituted phenyl or $C_{1-6}$ aliphatic, and p is 0-4. In some embodiments, Ring C is optionally substituted

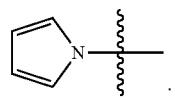

In some embodiments, Ring C is optionally substituted

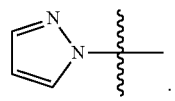

In some embodiments, Ring C is optionally substituted

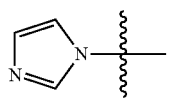

In some embodiments, Ring C is an optionally substituted 5 membered monocyclic heteroaryl ring having 1-2 heteroatoms independently selected from nitrogen, oxygen, or sulfur. In some embodiments, Ring C is an optionally substituted 6 membered monocyclic heteroaryl ring having 1-4 heteroatoms independently selected from nitrogen, oxygen, or sulfur. In some embodiments, Ring C is an optionally substituted 6 membered monocyclic heteroaryl ring having 1-2 heteroatoms independently selected from nitrogen, oxygen, or sulfur.

In some embodiments, Ring C is an optionally substituted 3-7 membered saturated or partially unsaturated heterocyclic ring having 1-3 heteroatoms independently selected from nitrogen, oxygen or sulfur. In some embodiments, Ring C is an optionally substituted 3-7 membered saturated heterocyclic ring having 1-3 heteroatoms independently selected from nitrogen, oxygen, or sulfur. In some embodiments, Ring C is an optionally substituted 5-6 membered saturated heterocyclic ring having 1-2 heteroatoms independently selected from nitrogen, oxygen, or sulfur. In some embodiments, Ring C is an optionally substituted 3-7 membered partially unsaturated heterocyclic ring having 1-3 heteroatoms independently selected from nitrogen, oxygen, or sulfur. In some embodiments, Ring C is an optionally substituted 5-6 membered partially unsaturated heterocyclic ring having 1-2 heteroatoms independently selected from nitrogen, oxygen, or sulfur.

In some embodiments, Ring C is an optionally substituted 7-10 membered bicyclic saturated or partially unsaturated heterocyclic ring having 1-5 heteroatoms independently selected from nitrogen, oxygen or sulfur. In some embodiments, Ring C is an optionally substituted 7-10 membered bicyclic saturated heterocyclic ring having 1-5 heteroatoms independently selected from nitrogen, oxygen, or sulfur. In some embodiments, Ring C is an optionally substituted 8-10 membered bicyclic saturated heterocyclic ring having 1-2 heteroatoms independently selected from nitrogen, oxygen, or sulfur. In some embodiments, Ring C is an optionally substituted 7-10 membered bicyclic partially unsaturated heterocyclic ring having 1-5 heteroatoms independently selected from nitrogen, oxygen, or sulfur. In some embodiments, Ring C is an optionally substituted 8-10 membered bicyclic partially unsaturated heterocyclic ring having 1-2 heteroatoms independently selected from nitrogen, oxygen, or sulfur.

In some embodiments, Ring C is an optionally substituted 8-14 membered bicyclic or tricyclic heteroaryl ring having 1-5 heteroatoms independently selected from nitrogen, oxygen, or sulfur. In some embodiments, Ring C is an optionally substituted 8-10 membered bicyclic heteroaryl ring having 1-5 heteroatoms independently selected from nitrogen, oxygen, or sulfur. In some embodiments, Ring C is an optionally substituted 8 membered bicyclic heteroaryl ring having 1-3 heteroatoms independently selected from nitrogen, oxygen, or sulfur. In some embodiments, Ring C is an optionally substituted 9 membered bicyclic heteroaryl ring having 1-3 heteroatoms independently selected from nitrogen, oxygen, or sulfur. In some embodiments, Ring C is an optionally substituted 10 membered bicyclic heteroaryl ring having 1-3 heteroatoms independently selected from nitrogen, oxygen, or sulfur. In some embodiments, Ring C is an optionally substituted 10-14 membered tricyclic heteroaryl ring having 1-5 heteroatoms independently selected from nitrogen, oxygen, or sulfur.

Exemplary embodiments for Ring C include but are not limited to those described for R wherein R is an optionally substituted group selected from phenyl, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

As generally defined above, each $R^x$ is independently R, halogen, —CN, —C(O)R, —C(O)OR, —C(O)N(R)$_2$, —C(O)N(R)(OR), —OR, —OC(O)R, —OC(O)N(R)$_2$, —OSi(R)$_3$, —SR, —S(O)R, —S(O)$_2$R, —S(O)$_2$OR, —S(O)$_2$N(R)$_2$, —NO$_2$, —N(R)$_2$, —NROR, —NRC(O)R, —N(R)C(O)OR, —N(R)C(O)N(R)$_2$, —N(R)S(O)$_2$R, —N(R)S(O)$_2$N(R)$_2$, —P(R)$_2$, —P(OR)$_2$, —P(O)(R)$_2$, —P(O)(OR)$_2$, —P(O)[N(R)$_2$]$_2$, or —Si(R)$_3$.

In some embodiments, $R^x$ is halogen. In some embodiments, $R^x$ is —F. In some embodiments, $R^x$ is —Cl. In some embodiments, $R^x$ is —Br. In some embodiments, $R^x$ is —I.

In some embodiments, $R^x$ is hydrogen. In some embodiments, $R^x$ is an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In certain embodiments, $R^x$ is R, wherein R is as defined above and described herein. In some embodiments, $R^x$ is optionally substituted $C_{1-6}$ aliphatic. In some embodiments, $R^x$ is optionally substituted $C_{1-6}$ alkyl. In some embodiments, $R^x$ is optionally substituted $C_{1-6}$ haloalkyl. In some embodiments, $R^x$ is optionally substituted $C_{1-6}$ haloalkyl, wherein one substituent is —F. In some embodiments, $R^x$ is optionally substituted $C_{1-6}$ haloalkyl, wherein two or more substituents are —F. In certain embodiments, $R^x$ is selected from methyl, ethyl, propyl, or butyl. In certain embodiments, $R^x$ is isopropyl. In certain embodiments, $R^x$ is —CF$_3$.

In some embodiments, $R^x$ is optionally substituted phenyl. In some embodiments, $R^x$ is substituted phenyl. In some embodiments, $R^x$ is phenyl.

In some embodiments, $R^x$ is —CN. In some embodiments, $R^x$ is —C(O)R, wherein R is as defined above and described herein. In some embodiments, $R^x$ is —C(O)OR, wherein R is as defined above and described herein. In some embodiments, $R^x$ is —C(O)N(R)$_2$, wherein each R is independently as defined above and described herein. In some embodiments, $R^x$ is —C(O)N(R)(OR), wherein each R is independently as defined above and described herein. In some embodiments, $R^x$ is —OR, wherein R is as defined above and described herein. In some embodiments, $R^x$ is —OC(O)R, wherein R is as defined above and described herein. In some embodiments, $R^x$ is —OC(O)N(R)$_2$, wherein each R is independently as defined above and described herein. In some embodiments, $R^x$ is —OSi(R)$_3$, wherein each R is independently as defined above and described herein. In some embodiments, $R^x$ is —SR, wherein R is as defined above and described herein. In some embodiments, $R^x$ is —S(O)R, wherein R is independently as defined above and described herein. In some embodiments, $R^x$ is —S(O)$_2$R, wherein R is as defined above and described herein. In some embodiments, $R^x$ is —S(O)$_2$OR, wherein R is as defined above and described herein. In some embodiments, $R^x$ is —S(O)$_2$N(R)$_2$, wherein each R is independently as defined above and described herein. In some embodiments, $R^x$ is —NO$_2$. In some embodiments, $R^x$ is —N(R)$_2$, wherein each R is independently as defined above and described herein. In some embodiments, $R^x$ is —NROR, wherein each R is independently as defined above and described herein. In some embodiments, $R^x$ is —NRC(O)R, wherein each R is independently as defined above and described herein. In some embodiments, $R^x$ is —N(R)C(O)OR, wherein each R is independently as defined above and described herein. In some embodiments, $R^x$ is —N(R)C(O)N(R)$_2$, wherein each R is independently as defined above and described herein. In some embodiments, $R^x$ is —N(R)S(O)$_2$R, wherein each R is independently as defined above and described herein. In some embodiments, $R^x$ is —N(R)S(O)$_2$N(R)$_2$, wherein each R is independently as defined above and described herein. In some embodiments, $R^x$ is —P(R)$_2$, wherein each R is independently as defined above and described herein. In some embodiments, $R^x$ is —P(OR)$_2$, wherein each R is independently as defined above and described herein. In some embodiments, $R^x$ is —P(O)(R)$_2$, wherein each R is independently as defined above and described herein. In some embodiments, $R^x$ is —P(O)(OR)$_2$, wherein each R is independently as defined above and described herein. In some embodiments, $R^x$ is —P(O)[N(R)$_2$]$_2$, wherein each R is independently as defined above and described herein. In some embodiments, $R^x$ is —Si(R)$_3$, wherein each R is independently as defined above and described herein.

As generally defined above, each $R^{5a}$ is independently R, wherein R is as defined above and described herein. In some embodiments, $R^{5a}$ is hydrogen.

As generally defined above, each of p and t is independently 0-7.

In some embodiments, p is 0-7. In some embodiments, p is 0-5. In some embodiments, p is 0-4. In some embodiments, p is 0. In some embodiments, p is 1-6. In some embodiments, p is 1-5. In some embodiments, p is 1-4. In some embodiments, p is 1. In some embodiments, p is 2. In some embodiments, p is 3. In some embodiments, p is 4. In some embodiments, p is 5. In some embodiments, p is 6. In some embodiments, p is 7.

In some embodiments, t is 0-7. In some embodiments, t is 0-5. In some embodiments, t is 0-4. In some embodiments, t is 0. In some embodiments, t is 1-6. In some embodiments, t is 1-5. In some embodiments, t is 1-4. In some embodiments, t is 1. In some embodiments, t is 2. In some embodiments, t is 3. In some embodiments, t is 4. In some embodiments, t is 5. In some embodiments, t is 6. In some embodiments, t is 7.

In some embodiments, m is 0-3. In some embodiments, m is 0. In some embodiments, m is 1-3. In some embodiments, m is 1. In some embodiments, m is 2. In some embodiments, m is 3.

In some embodiments, $Ar^b$ is an optionally substituted 10-14 membered bicyclic or polycyclic aryl ring. In some embodiments, $Ar^b$ is R, wherein R is an optionally substituted 10-membered bicyclic aryl ring. In some embodiments, $Ar^b$ is an optionally substituted 14-membered tricyclic aryl ring. In some embodiments, $Ar^b$ is R, wherein R is an optionally substituted 5-6 membered monocyclic heteroaryl ring having 1-4 heteroatoms independently selected from nitrogen, oxygen or sulfur. In some embodiments, $Ar^b$ is an optionally substituted 8-14 membered bicyclic or polycyclic heteroaryl ring having 1-5 heteroatoms independently selected from nitrogen, oxygen or sulfur. In some embodiments, $Ar^b$ is R, wherein R is an optionally substituted 8-10 membered bicyclic heteroaryl ring having 1-5 heteroatoms independently selected from nitrogen, oxygen or sulfur. In some embodiments, $Ar^b$ is an optionally substituted tricyclic heteroaryl ring having 1-5 heteroatoms independently selected from nitrogen, oxygen or sulfur.

In some embodiments, $R^{5'}$ is —OAr$^b$, wherein Ar$^b$ is

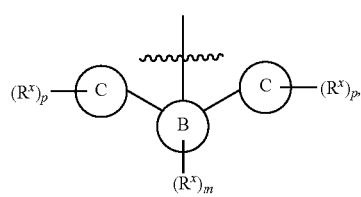

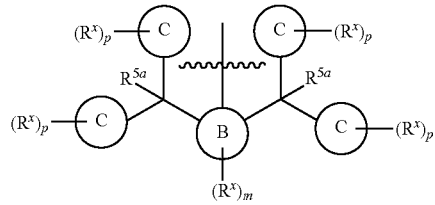

In some embodiments, $R^{5'}$ is —OAr$^b$, wherein Ar$^b$ is

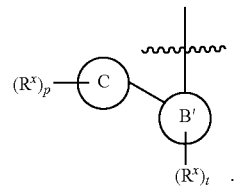

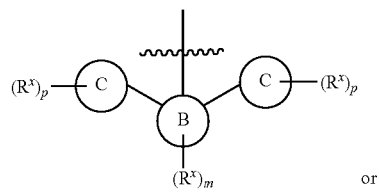

In some embodiments, $R^{5'}$ is —OAr$^b$, wherein Ar$^b$ is is

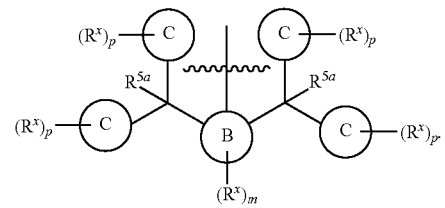

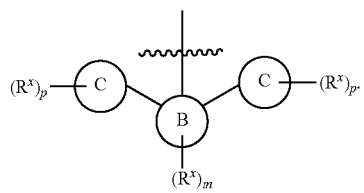

In some embodiments, $R^{5'}$ is optionally substituted

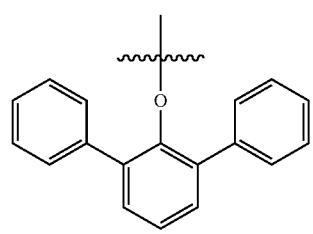

In some embodiments, R⁵' is substituted
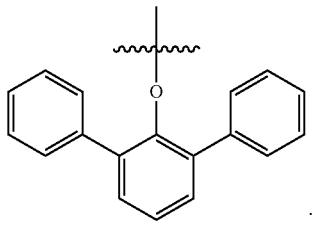 [SMILES: *Oc1c(-c2ccccc2)cccc1-c1ccccc1]
In some embodiments, R⁵' is
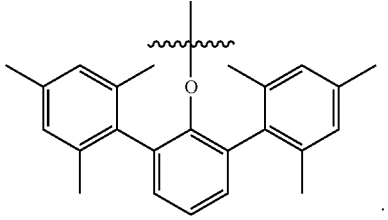
In some embodiments, R⁵' is
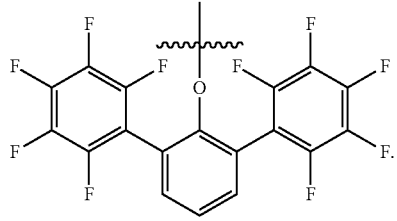 [SMILES: *Oc1c(-c2c(F)c(F)c(F)c(F)c2F)cccc1-c1c(F)c(F)c(F)c(F)c1F]
In some embodiments, In some embodiments, R⁵' is —OAr^b, wherein Ar^b is
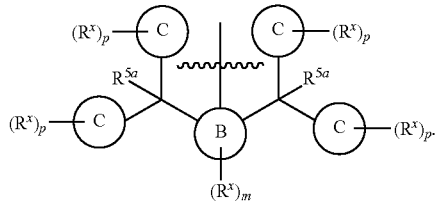
In some embodiments, In some embodiments, R⁵' is —OAr^b, wherein Ar^b is
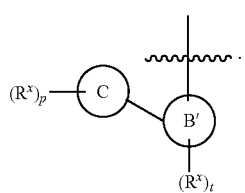
Exemplary R⁵' is depicted below:
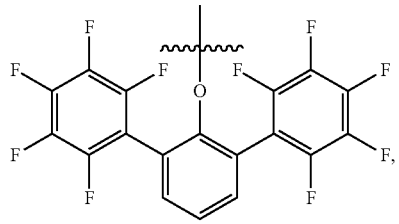
(DFTO)
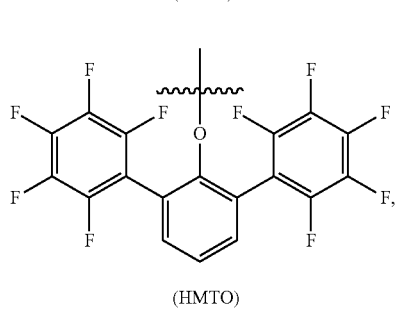
(HMTO)
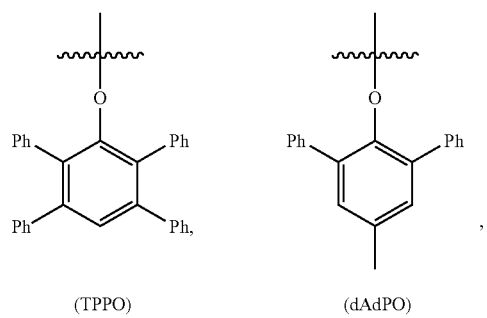
(TPPO)  (dAdPO)
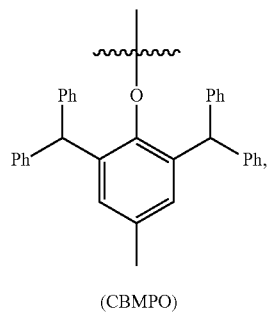
(CBMPO)
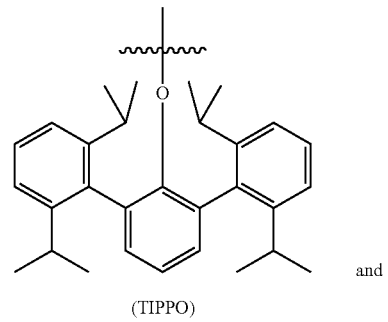
and
(TIPPO)

-continued

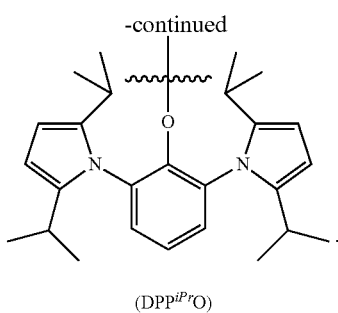

(DPP$^{iPr}$O)

As generally defined above, each R$^6$ is independently —R, —OR, —SR, —N(R)$_2$, —OC(O)R, —S(O)R, —SO$_2$R, —SO$_2$N(R)$_2$, —C(O)N(R)$_2$, —NRC(O)R, or —NRSO$_2$R, wherein each R is independently as defined above and described herein.

In some embodiments, R$^6$ is R, wherein R is as defined above and described herein. In some embodiments, R$^6$ is hydrogen. In some embodiments, R$^6$ is an optionally substituted group selected from C$_{1-10}$ aliphatic, C$_{1-10}$ heteroalkyl having 1-3 heteroatoms independently selected from nitrogen, oxygen or sulfur, phenyl, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur. In some embodiments, R$^6$ is optionally substituted C$_{1-10}$ aliphatic. In some embodiments, R$^6$ is optionally substituted C$_{1-6}$ aliphatic. In some embodiments, R$^6$ is optionally substituted C$_{1-6}$ alkyl. In some embodiments, R$^6$ is methyl. In some embodiments, each R$^6$ is methyl.

In some embodiments, R$^6$ is —OR, —SR, —N(R)$_2$, —OC(O)R, —S(O)R, —SO$_2$R, —SO$_2$N(R)$_2$, —C(O)N(R)$_2$, —NRC(O)R, or —NRSO$_2$R, wherein each R is independently as defined above and described herein. In some embodiments, R$^6$ is —OR, wherein R is as defined above and described herein. In some embodiments, R$^6$ is —SR, wherein R is as defined above and described herein. In some embodiments, R$^6$ is —N(R)$_2$, wherein each R is independently as defined above and described herein. In some embodiments, R$^6$ is —OC(O)R, wherein R is as defined above and described herein. In some embodiments, R$^6$ is —S(O)R, wherein R is as defined above and described herein. In some embodiments, R$^6$ is —S(O)$_2$R, wherein R is as defined above and described herein. In some embodiments, R$^6$ is —SO$_2$N(R)$_2$, wherein each R is independently as defined above and described herein. In some embodiments, R$^6$ is —C(O)N(R)$_2$, wherein each R is independently as defined above and described herein. In some embodiments, R$^6$ is —NRC(O)R, wherein each R is independently as defined above and described herein. In some embodiments, R$^6$ is —NRSO$_2$R, wherein each R is as defined above and described herein. In some embodiments, each R$^6$ is methyl, and R$^7$ is phenyl.

As generally defined above, R$^7$ is optionally substituted phenyl. In some embodiments, R$^7$ is phenyl. In some embodiments, R$^7$ is substituted phenyl.

As generally defined above, each R$^8$ is independently a phosphorus-containing ligand, wherein the phosphorus-containing ligand is bonded to W through a phosphorus atom. In some embodiments, R$^8$ is a compound having the structure of P(R$^{8a}$)$_3$, wherein each R$^{8a}$ is independently —R, —N(R)$_2$ or —OR. In some embodiments, R$^8$ is a compound having the structure of P(R)$_3$, wherein each R is independently as defined above and described herein. In some embodiments, R$^8$ is a compound having the structure of P(R)$_3$, wherein each R is independently optionally substituted C$_{1-10}$ aliphatic or phenyl. In some embodiments, R$^8$ is PPhMe$_2$. In some embodiments, R$^8$ is optionally substituted PPh$_2$Me. In some embodiments, a ligand, for example R$^8$, dissociates fast enough when used in a metathesis reaction, such as ROMP. In some embodiments, a ligand dissociates fast enough to form a compound of formula II wherein n is 0.

As generally defined above, each R$^9$ is independently a neutral ligand. In some embodiments, R$^9$ is a phosphorus-containing ligand. In some embodiments, R$^9$ is R$^8$. In some embodiments, R$^9$ has the structure of P(R$^{8a}$)$_3$, wherein each R$^{8a}$ is independently —R, —N(R)$_2$ or —OR. In some embodiments, R$^9$ has the structure of P(R)$_3$, wherein each R is independently as defined above and described herein. In some embodiments, R$^9$ is a nitrogen-containing ligand. In some embodiments, R$^9$ has the structure of N(R)$_3$, wherein each R is independently as defined above and described herein. In some embodiments, R$^9$ is an oxygen-containing ligand. In some embodiments, R$^9$ has the structure of (R)$_2$O, wherein each R is independently as defined above and described herein.

As generally defined above, each R is independently hydrogen or an optionally substituted group selected from C$_{1-10}$ aliphatic, C$_{1-10}$ heteroalkyl having 1-3 heteroatoms independently selected from nitrogen, oxygen or sulfur, phenyl, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; or:
  two R groups are optionally taken together with the intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen or sulfur.

In some embodiments, R is hydrogen or an optionally substituted group selected from C$_{1-10}$ aliphatic, C$_{1-10}$ heteroalkyl having 1-3 heteroatoms independently selected from nitrogen, oxygen or sulfur, phenyl, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur. In some embodiments, two R groups on the same atom are optionally taken together with the atom to which they are attached to form an optionally substituted 3-10 membered, monocyclic or bicyclic, saturated, partially unsaturated, or aryl ring having, in addition to the atom to which they are attached, 0-4 heteroatoms independently selected from nitrogen, oxygen or sulfur.

In some embodiments, R is optionally substituted $C_{1-10}$ aliphatic. In some embodiments, R is optionally substituted $C_{1-6}$ aliphatic. In some embodiments, R is optionally substituted $C_{1-6}$ alkyl. In some embodiments, R is optionally substituted hexyl, pentyl, butyl, propyl, ethyl or methyl. In some embodiments, R is optionally substituted hexyl. In some embodiments, R is optionally substituted pentyl. In some embodiments, R is optionally substituted butyl. In some embodiments, R is optionally substituted propyl. In some embodiments, R is optionally substituted ethyl. In some embodiments, R is optionally substituted methyl. In some embodiments, R is hexyl. In some embodiments, R is pentyl. In some embodiments, R is butyl. In some embodiments, R is propyl. In some embodiments, R is ethyl. In some embodiments, R is methyl. In some embodiments, R is isopropyl. In some embodiments, R is n-propyl. In some embodiments, R is tert-butyl. In some embodiments, R is sec-butyl. In some embodiments, R is n-butyl.

In some embodiments, R is optionally substituted $C_{1-10}$ heteroalkyl having 1-3 heteroatoms independently selected from nitrogen, oxygen or sulfur. In some embodiments, R is optionally substituted $C_{1-6}$ heteroalkyl having 1-3 heteroatoms independently selected from nitrogen, oxygen or sulfur. In some embodiments, R is optionally substituted $C_{1-6}$ heteroalkyl comprising 1-3 moieties independently selected from

—N=, ≡N, —S—, —S(O)—, —S(O)$_2$—, —O— or =O.

In some embodiments, R is optionally substituted phenyl. In some embodiments, R is optionally substituted phenyl wherein one or more substituents are halogen. In some embodiments, R is optionally substituted phenyl wherein one or more substituents are —F. In some embodiments, R is optionally substituted phenyl wherein one or more substituents are —Cl. In some embodiments, R is optionally substituted phenyl wherein one or more substituents are —Br. In some embodiments, R is optionally substituted phenyl wherein one or more substituents are —I. In some embodiments, R is phenyl.

In some embodiments, R is an optionally substituted 3-7 membered saturated or partially unsaturated carbocyclic ring. In some embodiments, R is or an optionally substituted 3-membered saturated or partially unsaturated carbocyclic ring. In some embodiments, R is or an optionally substituted 4-membered saturated or partially unsaturated carbocyclic ring. In some embodiments, R is or an optionally substituted 5-membered saturated or partially unsaturated carbocyclic ring. In some embodiments, R is or an optionally substituted 6-membered saturated or partially unsaturated carbocyclic ring. In some embodiments, R is or an optionally substituted 7-membered saturated or partially unsaturated carbocyclic ring. In some embodiments, R is a 3-7 membered saturated or partially unsaturated carbocyclic ring. In some embodiments, R is a 3-membered saturated or partially unsaturated carbocyclic ring. In some embodiments, R is a 4-membered saturated or partially unsaturated carbocyclic ring. In some embodiments, R is a 5-membered saturated or partially unsaturated carbocyclic ring. In some embodiments, R is a 6-membered saturated or partially unsaturated carbocyclic ring. In some embodiments, R is a 7-membered saturated or partially unsaturated carbocyclic ring. In some embodiments, R is optionally substituted cycloheptyl. In some embodiments, R is cycloheptyl. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, R is or an optionally substituted 6-10 membered bicyclic saturated, partially unsaturated or aryl ring. In some embodiments, R is or an optionally substituted 6-10 membered bicyclic saturated ring. In some embodiments, R is or an optionally substituted 8-10 membered bicyclic partially unsaturated ring. In some embodiments, R is or an optionally substituted 8-10 membered bicyclic aryl ring. In some embodiments, R is a 6-10 membered bicyclic saturated, partially unsaturated or aryl ring. In some embodiments, R is a 6-10 membered bicyclic saturated ring. In some embodiments, R is an 8-10 membered bicyclic partially unsaturated ring. In some embodiments, R is an 8-10 membered bicyclic aryl ring. In some embodiments, R is optionally substituted naphthyl.

In some embodiments, R is an optionally substituted 5-6 membered monocyclic heteroaryl ring having 1-4 heteroatoms independently selected from nitrogen, oxygen or sulfur. In some embodiments, R is a substituted 5-6 membered monocyclic heteroaryl ring having 1-4 heteroatoms independently selected from nitrogen, oxygen or sulfur. In some embodiments, R is an unsubstituted 5-6 membered monocyclic heteroaryl ring having 1-4 heteroatoms independently selected from nitrogen, oxygen or sulfur.

In some embodiments, R is an optionally substituted 5-membered monocyclic heteroaryl ring having 1-4 heteroatoms independently selected from nitrogen, oxygen or sulfur. In some embodiments, R is an optionally substituted 6-membered monocyclic heteroaryl ring having 1-4 heteroatoms independently selected from nitrogen, oxygen or sulfur.

In some embodiments, R is an optionally substituted 5-membered monocyclic heteroaryl ring having one heteroatom selected from nitrogen, oxygen or sulfur. In some embodiments, R is selected from optionally substituted pyrrolyl, furanyl, or thienyl.

In some embodiments, R is an optionally substituted 5-membered heteroaryl ring having two heteroatoms independently selected from nitrogen, oxygen or sulfur. In certain embodiments, R is an optionally substituted 5-membered heteroaryl ring having one nitrogen atom, and an additional heteroatom selected from sulfur or oxygen. Exemplary R groups include but are not limited to optionally substituted pyrazolyl, imidazolyl, thiazolyl, isothiazolyl, oxazolyl or isoxazolyl.

In some embodiments, R is an optionally substituted 5-membered heteroaryl ring having three heteroatoms independently selected from nitrogen, oxygen or sulfur. Exemplary R groups include but are not limited to optionally substituted triazolyl, oxadiazolyl or thiadiazolyl.

In some embodiments, R is an optionally substituted 5-membered heteroaryl ring having four heteroatoms independently selected from nitrogen, oxygen or sulfur. Exemplary R groups include but are not limited to optionally substituted tetrazolyl, oxatriazolyl and thiatriazolyl.

In some embodiments, R is or an optionally substituted 6-membered heteroaryl ring having 1-4 nitrogen atoms. In some embodiments, R is or an optionally substituted 6-membered heteroaryl ring having 1-3 nitrogen atoms. In some embodiments, R is a 6-membered heteroaryl ring having 1-4 nitrogen atoms. In some embodiments, R is a 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having four nitrogen atoms. In some embodiments, R is an optionally substituted 6-membered heteroaryl ring having three nitrogen atoms. In some embodiments, R is an optionally substituted 6-membered heteroaryl ring having two nitrogen atoms. In certain embodiments, R is an optionally substituted 6-membered heteroaryl ring having one nitrogen atom. Exemplary R groups include but are not limited to optionally substituted pyridinyl, pyrimidinyl, pyrazinyl, pyridazinyl, triazinyl, or tetrazinyl.

In some embodiments, R is an optionally substituted 3-7 membered saturated or partially unsaturated heterocyclic ring having 1-3 heteroatoms independently selected from nitrogen, oxygen or sulfur. In some embodiments, R is a substituted 3-7 membered saturated or partially unsaturated heterocyclic ring having 1-3 heteroatoms independently selected from nitrogen, oxygen or sulfur. In some embodiments, R is an unsubstituted 3-7 membered saturated or partially unsaturated heterocyclic ring having 1-3 heteroatoms independently selected from nitrogen, oxygen or sulfur.

In certain embodiments, R is an optionally substituted 5-7 membered partially unsaturated monocyclic ring having 1-3 heteroatoms independently selected from nitrogen, oxygen or sulfur. In certain embodiments, R is an optionally substituted 5-6 membered partially unsaturated monocyclic ring having 1-3 heteroatoms independently selected from nitrogen, oxygen or sulfur. In certain embodiments, R is an optionally substituted 5-membered partially unsaturated monocyclic ring having 1-3 heteroatoms independently selected from nitrogen, oxygen or sulfur. Exemplary R groups include but are not limited to optionally substituted dihydroimidazolyl, dihydrothiazolyl, dihydrooxazolyl, or oxazolinyl. In certain embodiments, R is an optionally substituted 6-membered partially unsaturated monocyclic ring having 1-3 heteroatoms independently selected from nitrogen, oxygen or sulfur. Exemplary R groups include but are not limited to optionally substituted dihydropyridinyl, tetrahydropyridinyl, dihydropyrimidinyl, tetrahydropyrimidinyl, dihydropyrazinyl, tetrohydropyrazinyl, dihydrotriazinyl, tetrahydrotriazinyl, dihydrodioxinyl, dihydrooxathiinyl, dihydrooxazinyl, dihydrodithiine, dihydrothiazine, dioxinyl, oxathiinyl, oxazinyl, dithiinyl, or thiazinyl. In certain embodiments, R is an optionally substituted 7-membered partially unsaturated monocyclic ring having 1-3 heteroatoms independently selected from nitrogen, oxygen or sulfur. Exemplary R groups include but are not limited to optionally substituted azepiyl, oxepinyl, thiepinyl, diazepinyl, oxazepinyl, thiazepinyl, triazepinyl, oxadiazepinyl, thiadiazepinyl, dihydroazepiyl, dihydrooxepinyl, dihydrothiepinyl, dihydrodiazepinyl, dihydrooxazepinyl, dihydrothiazepinyl, dihydrotriazepinyl, dihydrooxadiazepinyl, dihydrothiadiazepinyl, tetrahydroazepiyl, tetrahydrooxepinyl, tetrahydrothiepinyl, tetrahydrodiazepinyl, tetrahydrooxazepinyl, tetrahydrothiazepinyl, tetrahydrotriazepinyl, tetrahydrooxadiazepinyl, or tetrahydrothiadiazepinyl.

In some embodiments, R is optionally substituted 3-membered heterocyclic ring having one heteroatom selected from nitrogen, oxygen or sulfur. Exemplary R groups include but are not limited to optionally substituted aziridinyl, thiiranyl or oxiranyl. In some embodiments, R is optionally substituted 4-membered heterocyclic ring having 1-3 heteroatoms independently selected from nitrogen, oxygen or sulfur. Exemplary R groups include but are not limited to optionally substituted azetidinyl, oxetanyl, thietanyl, oxazetidinyl, thiazetidinyl, or diazetidinyl. In some embodiments, R is optionally substituted 5-membered heterocyclic ring having 1-3 heteroatoms independently selected from nitrogen, oxygen or sulfur. Exemplary R groups include but are not limited to optionally substituted pyrrolidinyl, tetrahydrofuranyl, tetrahydrothienyl, oxazolidinyl, dioxolanyl, oxathiolanyl, thiazolidinyl, dithiolanyl, imidazolidinyl, isothiazolidinyl, pyrazolidinyl, isoxazolidinyl, isothiazolidinyl, triazolidinyl, oxadiazolidinyl, thiadiazolidinyl, oxadiazolidinyl, dioxazolidinyl, oxathiazolidinyl, thiadiazolidinyl or dithiazolidinyl. In some embodiments, R is optionally substituted 6-membered heterocyclic ring having 1-3 heteroatoms independently selected from nitrogen, oxygen or sulfur. Exemplary R groups include but are not limited to optionally substituted piperidinyl, tetrahydropyranyl, tetrahydrothiopyranyl, piperazinyl, morpholinyl, thiomorpholinyl, dithianyl, dioxanyl, oxathianyl, triazinanyl, oxadiazinanyl, thiadiazinanyl, dithiazinanyl, dioxazinanyl, oxathiazinanyl, oxadithianyl, trioxanyl, dioxathianyl or trithianyl. In some embodiments, R is optionally substituted 7-membered heterocyclic ring having 1-3 heteroatoms independently selected from nitrogen, oxygen or sulfur. Exemplary R groups include but are not limited to optionally substituted azepanyl, oxepanyl, thiepanyl, diazepanyl, oxazepanyl, thiazepanyl, dioxepanyl, oxathiepanyl, dithiepanyl, triazepanyl, oxadiazepanyl, thiadiazepanyl, dioxazepanyl, oxathiazepanyl, dithiazepanyl, trioxepanyl, dioxathiepanyl, oxadithiepanyl or trithiepanyl.

In certain embodiments, R is optionally substituted oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothienyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothienyl, or tetrahydrothiopyranyl.

In some embodiments, R is an optionally substituted 7-10 membered bicyclic saturated or partially unsaturated heterocyclic ring having 1-5 heteroatoms independently selected from nitrogen, oxygen or sulfur. In some embodiments, R is a 7-10 membered bicyclic saturated or partially unsaturated heterocyclic ring having 1-5 heteroatoms independently selected from nitrogen, oxygen or sulfur. In some embodiments, R is optionally substituted indolinyl. In some embodiments, R is optionally substituted isoindolinyl. In some embodiments, R is optionally substituted 1,2,3,4-tetrahydroquinolinyl. In some embodiments, R is optionally substituted 1,2,3,4-tetrahydroisoquinolinyl. In some embodiments, R is an optionally substituted azabicyclo[3.2.1]octanyl.

In some embodiments, R is an optionally substituted 8-10 membered bicyclic heteroaryl ring having 1-5 heteroatoms independently selected from nitrogen, oxygen or sulfur. In some embodiments, R is an 8-10 membered bicyclic heteroaryl ring having 1-5 heteroatoms independently selected from nitrogen, oxygen or sulfur.

In some embodiments, R is an optionally substituted 5,6-fused heteroaryl ring having 1-5 heteroatoms independently selected from nitrogen, oxygen or sulfur. In some embodiments, R is an optionally substituted 5,6-fused heteroaryl ring having 1-4 heteroatoms independently selected from nitrogen, oxygen or sulfur. In some embodiments, R is an optionally substituted 5,6-fused heteroaryl ring having 1-3 heteroatoms independently selected from nitrogen, oxygen or sulfur. In some embodiments, R is an optionally substituted 5,6-fused heteroaryl ring having two heteroatoms independently selected from nitrogen, oxygen or sulfur. In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is an optionally substituted 5,6-fused heteroaryl ring having three heteroatoms independently selected from nitrogen, oxygen or sulfur. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, R is an optionally substituted 5,6-fused heteroaryl ring having four heteroatoms independently selected from nitrogen, oxygen or sulfur. In some embodiments, R is an optionally substituted 5,6-fused heteroaryl ring having five heteroatoms independently selected from nitrogen, oxygen or sulfur.

In some embodiments, R is an optionally substituted 5,6-fused heteroaryl ring having 1-5 heteroatoms independently selected from nitrogen, oxygen or sulfur. In other embodiments, R is an optionally substituted 5,6-fused heteroaryl ring having 1-2 heteroatoms independently selected from nitrogen, oxygen or sulfur. In certain embodiments, R is an optionally substituted 5,6-fused heteroaryl ring having one heteroatom independently selected from nitrogen, oxygen or sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen or sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen or sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen or sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen or sulfur.

In certain embodiments, R is an optionally substituted 6,6-fused heteroaryl ring having 1-5 heteroatoms independently selected from nitrogen, oxygen or sulfur. In some embodiments, R is an optionally substituted 6,6-fused heteroaryl ring having 1-2 heteroatoms independently selected from nitrogen, oxygen or sulfur. In other embodiments, R is an optionally substituted 6,6-fused heteroaryl ring having one heteroatom selected from nitrogen, oxygen or sulfur. In some embodiments, R is optionally substituted quinolinyl. In some embodiments, R is optionally substituted isoquinolinyl. In some embodiments, R is an optionally substituted 6,6-fused heteroaryl ring having two heteroatoms independently selected from nitrogen, oxygen or sulfur. In some embodiments, R is optionally substituted quinazolinyl, phthalazinyl, quinoxalinyl or naphthyridinyl. In some embodiments, R is an optionally substituted 6,6-fused heteroaryl ring having three heteroatoms independently selected from nitrogen, oxygen or sulfur. In some embodiments, R is optionally substituted pyridopyrimidinyl, pyridopyridazinyl, pyridopyrazinyl, or benzotriazinyl. In some embodiments, R is an optionally substituted 6,6-fused heteroaryl ring having four heteroatoms independently selected from nitrogen, oxygen or sulfur. In some embodiments, R is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, R is an optionally substituted 6,6-fused heteroaryl ring having five heteroatoms independently selected from nitrogen, oxygen or sulfur.

In some embodiments, two R groups are optionally taken together with the intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen or sulfur. In some embodiments, two R groups on the same atom are optionally taken together with the atom to which they are attached to form an optionally substituted 3-10 membered, monocyclic or bicyclic, saturated, partially unsaturated, or aryl ring having 0-4 heteroatoms independently selected from nitrogen, oxygen or sulfur. In some embodiments, two R groups on the same carbon atom are optionally taken together with the carbon atom to form an optionally substituted 3-10 membered, monocyclic or bicyclic, saturated, partially unsaturated, or aryl ring having 0-4 heteroatoms independently selected from nitrogen, oxygen or sulfur. In some embodiments, two R groups on the same nitrogen atom are optionally taken together with the nitrogen atom to form an optionally substituted 3-10 membered, monocyclic or bicyclic, saturated, partially unsaturated, or aryl ring having 1-5 heteroatoms independently selected from nitrogen, oxygen or sulfur. In some embodiments, two R groups on the same sulfur atom are optionally taken together with the sulfur atom to form an optionally substituted 3-10 membered, monocyclic or bicyclic, saturated, partially unsaturated, or aryl ring having 1-5 heteroatoms independently selected from nitrogen, oxygen or sulfur. In some embodiments, two R groups on the same oxygen atom are optionally taken together with the oxygen atom to form an optionally substituted 3-10 membered, monocyclic or bicyclic, saturated, partially unsaturated, or aryl ring having 1-5 heteroatoms independently selected from nitrogen, oxygen or sulfur. In some embodiments, two R groups on the same phosphorus atom are optionally taken together with the phosphorus atom to form an optionally substituted 3-10 membered, monocyclic or bicyclic, saturated, partially unsaturated, or aryl ring having, in addition to the phosphorus atom, 0-4 heteroatoms independently selected from nitrogen, oxygen or sulfur. In some embodiments, two R groups are optionally taken together with the intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen or sulfur, wherein the two R groups are attached to two different atoms.

In some embodiments, two R groups are taken together to form an optionally substituted saturated ring. In some embodiments, two R groups are taken together to form an optionally substituted partially unsaturated ring. In some embodiments, two R groups are taken together to form an optionally substituted aryl ring. In some embodiments, two R groups are taken together to form an optionally substituted heteroaryl ring. In some embodiments, two R groups are taken together to form an optionally substituted phenyl ring. In some embodiments, two R groups are taken together to form a bivalent optionally substituted phenyl ring.

As generally defined above, n is 0-2. In some embodiments, n is 0. In some embodiments, n is not 0. In some embodiments, n is 1 or 2. In some embodiments, n is 1. In some embodiments, n is 2. In some embodiments, $R^8$ or $R^9$ is a bidentate or polydentate ligand, and n can be a fraction.

In some embodiments, a provided compound of formula I is

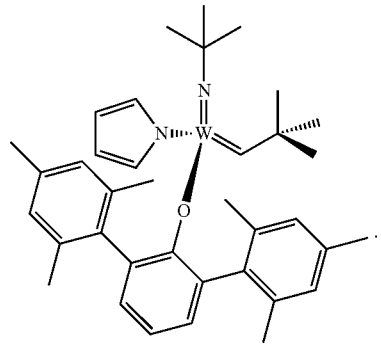

In some embodiments, a provided compound of formula II is

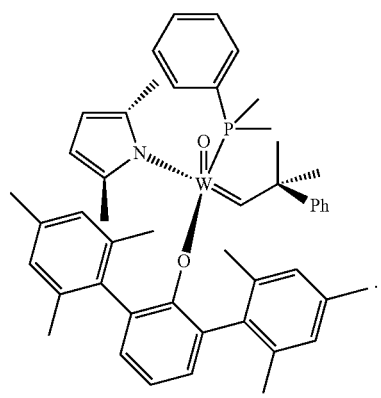

In some embodiments, a provided compound of formula III is

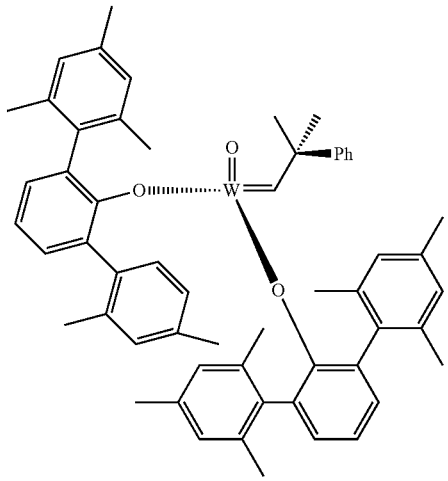

Figure 3:
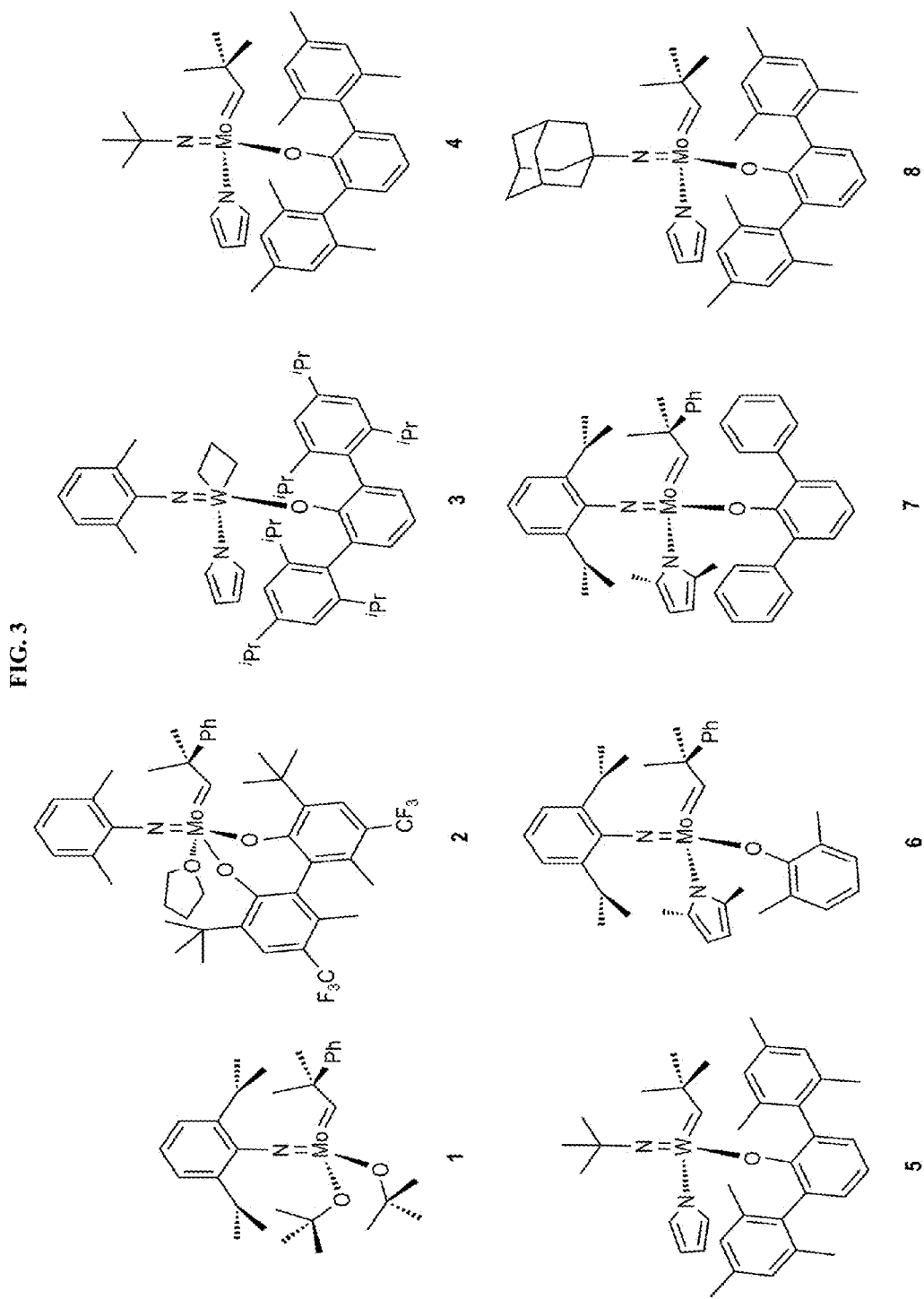
FIG. 3. Exemplary metal complex compounds.

In some embodiments, a provided compound is a compound selected from FIG. 3. In some embodiments, a provided compound is a compound selected from FIG. 5. In some embodiments, a provided compound is a compound selected from FIG. 8.

In some embodiments, a provided method of the present invention comprises providing a Lewis acid. Exemplary Lewis acids are widely known in the art. In some embodiments, a provided Lewis acid is a boron-based Lewis acid. In some embodiments, a provided Lewis acid comprises boron. In some embodiments, a provided Lewis acid is a compound having the structure of $B(R)_3$. In some embodiments, a compound of $B(R)_3$ is $B(C_6F_5)_3$. In some embodiments, a Lewis acid is $B(C_6F_5)_3$. In some embodiments, a compound of $B(R)_3$ is $BPh_3$. In some embodiments, a Lewis acid is $BPh_3$.

In some embodiments, the present invention provides a method for performing ring opening metathesis polymerization ("ROMP") with high syndiotactic selectivity. In some embodiments, the present invention provides a method for performing ROMP with high syndiotactic selectivity, comprising providing a compound of formula I. In some embodiments, the present invention provides a method for performing ROMP with high syndiotactic selectivity, comprising providing a compound of formula II. In some embodiments, the present invention provides a method for performing ROMP with high syndiotactic selectivity, comprising providing a compound of formula III. In some embodiments, the present invention provides a method for performing ROMP with high syndiotactic selectivity, comprising providing a compound of formula III and a Lewis acid. In some embodiments, the present invention provides a method for performing ROMP with high syndiotactic selectivity, comprising providing a compound of formula III and a Lewis acid. In some embodiments, a Lewis acid comprises boron. In some embodiments, a Lewis acid is a compound having the structure of $B(R)_3$. In some embodiments, a Lewis acid is $B(C_6F_5)_3$.

In some embodiments, an ROMP product is greater than about 50% syndiotactic. In some embodiments, an ROMP product is greater than about 60% syndiotactic. In some embodiments, an ROMP product is greater than about 70% syndiotactic. In some embodiments, an ROMP product is greater than about 80% syndiotactic. In some embodiments, an ROMP product is greater than about 85% syndiotactic. In some embodiments, an ROMP product is greater than about 90% syndiotactic. In some embodiments, an ROMP product is greater than about 91% syndiotactic. In some embodiments, an ROMP product is greater than about 92% syndiotactic. In some embodiments, an ROMP product is greater than about 93% syndiotactic. In some embodiments, an ROMP product is greater than about 94% syndiotactic. In some embodiments, an ROMP product is greater than about 95% syndiotactic. In some embodiments, an ROMP product is greater than about 96% syndiotactic. In some embodiments, an ROMP product is greater than about 97% syndiotactic. In some embodiments, an ROMP product is greater than about 98% syndiotactic. In some embodiments, an ROMP product is greater than about 99% syndiotactic. In some embodiments, an ROMP product is greater than about 99.5% syndiotactic. In some embodiments, an ROMP product is 100% syndiotactic. In some embodiments, syndiotacticity is measured by NMR.

In some embodiments, the present invention provides a method for performing ring opening metathesis polymerization ("ROMP") with high syndiotactic selectivity and cis selectivity for newly formed double bonds in the backbone of a produced polymer. Measured by percentage of the newly formed double bonds through ROMP in cis configuration, in some embodiments, an ROMP product is greater than about 50% cis. In some embodiments, an ROMP product is greater than about 60% cis. In some embodiments, an ROMP product is greater than about 70% cis. In some embodiments, an ROMP product is greater than about 80% cis. In some embodiments, an ROMP product is greater than about 85% cis. In some embodiments, an ROMP product is greater than about 90% cis. In some embodiments, an ROMP product is greater than about 91% cis. In some embodiments, an ROMP product is greater than about 92% cis. In some embodiments, an ROMP product is greater than about 93% cis. In some embodiments, an ROMP product is greater than about 94% cis. In some embodiments, an ROMP product is greater than about 95% cis. In some embodiments, an ROMP product is greater than about 96% cis. In some embodiments, an ROMP product is greater than about 97% cis. In some embodiments, an ROMP product is greater than about 98% cis. In some embodiments, an ROMP product is greater than about 99% cis.

In some embodiments, an ROMP product is greater than about 50% cis and greater than about 50% syndiotactic. In some embodiments, an ROMP product is greater than about 60% cis and greater than about 50% syndiotactic. In some embodiments, an ROMP product is greater than about 70% cis and greater than about 50% syndiotactic. In some embodiments, an ROMP product is greater than about 80% cis and greater than about 50% syndiotactic. In some embodiments, an ROMP product is greater than about 85% cis and greater than about 50% syndiotactic. In some embodiments, an ROMP product is greater than about 90% cis and greater than about 50% syndiotactic. In some embodiments, an ROMP product is greater than about 95% cis and greater than about 50% syndiotactic. In some embodiments, an ROMP product is greater than about 98% cis and greater than about 50% syndiotactic. In some embodiments, an ROMP product is greater than about 90% cis and greater than about 60% syndiotactic. In some embodiments, an ROMP product is greater than about 90% cis and greater than about 70% syndiotactic. In some embodiments, an ROMP product is greater than about 90% cis and greater than about 80% syndiotactic. In some embodiments, an ROMP product is greater than about 90% cis and greater than about 90% syndiotactic. In some embodiments, an ROMP product is greater than about 95% cis and greater than about 90% syndiotactic. In some embodiments, an ROMP product is greater than about 98% cis and greater than about 90% syndiotactic. In some embodiments, an ROMP product is greater than about 95% cis and greater than about 95% syndiotactic. In some embodiments, an ROMP product is greater than about 95% cis and greater than about 96% syndiotactic. In some embodiments, an ROMP product is greater than about 95% cis and greater than about 97% syndiotactic. In some embodiments, an ROMP product is greater than about 95% cis and greater than about 98% syndiotactic. In some embodiments, an ROMP product is greater than about 95% cis and greater than about 99% syndiotactic. In some embodiments, an ROMP product is greater than about 99% cis and greater than about 99% syndiotactic. In some embodiments, an ROMP product is 100% cis and 100% syndiotactic.

In some embodiments, the present invention provides a method for improving the stereoselectivity of ROMP, comprising providing a Lewis acid. In some embodiments, the present invention provides a method for improving the tactic selectivity of an ROMP reaction, comprising providing a Lewis acid. In some embodiments, the present invention provides a method for improving the syndiotactic selectivity of an ROMP reaction, comprising providing a Lewis acid. In some embodiments, the present invention provides a method for improving the syndiotactic selectivity of an ROMP reaction, wherein the ROMP reaction comprises the use of a compound of formula III, comprising providing a Lewis acid. In some embodiments, a compound of formula III promotes the ROMP. In some embodiments, a compound of formula III initiates the ROMP. In some embodiments, a monomer is polymerized in the presence of a compound of formula III.

Acceleration of ROMP can lead to decreased stereoselectivity, including tacticity, in the polymer formed. Surprisingly, in some embodiments, the present invention provides a method for accelerating ROMP, comprising providing a Lewis acid, wherein the syndiotacticity of the produced polymer is not lowered. In some embodiments, the present invention provides a method for accelerating ROMP, comprising providing a Lewis acid, wherein the syndiotacticity of the produced polymer is increased. In some embodiments, the present invention provides a method for accelerating ROMP, wherein the ROMP comprising using a compound of formula III, comprising providing a Lewis acid, wherein the syndiotacticity of the produced polymer is increased. In some embodiments, a compound of formula III promotes the ROMP. In some embodiments, a compound of formula III initiates the ROMP. In some embodiments, a monomer is polymerized in the presence of a compound of formula III.

In some embodiments, an ROMP substrate of a provided method is optionally substituted norbornene. In some embodiments, an ROMP substrate of a provided method is substituted norbornene. In some embodiments, an ROMP substrate is highly reactive. In some embodiments, an ROMP substrate is more reactive than norbornene. In some embodiments, an ROMP substrate is more reactive than DCMNBD. In some embodiments, an ROMP substrate of a provided method is dicyclopentadiene. In some embodiments, an ROMP substrate of a provided method is endo-dicyclopentadiene. Highly reactive substrates such as dicyclopentadiene present unique challenges for ROMP; it is much more difficult to control stereoselectivity of the polymerization process of these monomers and accordingly, polymers with certain configurations, such as highly syndiotactic poly(DCPD) and hydrogenated poly(DCPD), could not be obtained prior to the present invention.

Conditions

Suitable conditions for performing provided methods generally employ one or more solvents. In certain embodiments, one or more organic solvents are used. Examples of such organic solvents include, but are not limited to, hydrocarbons such as benzene, toluene, and pentane, halogenated hydrocarbons such as dichloromethane, chloroform, or polar aprotic solvents, such as ethereal solvents including ether, DME, tetrahydrofuran (THF), or dioxanes, or protic solvents, such as alcohols, or mixtures thereof. In certain embodiments, one or more solvents are deuterated. In some embodiments, a single solvent is used. In certain embodiments, a solvent is benzene. In certain embodiments, a solvent is ether. In some embodiments, a solvent is a cyclohexane. In some embodiments, a solvent is chloroform. In some embodiments, a solvent is dichloromethane.

In some embodiments, mixtures of two or more solvents are used, and in some cases may be preferred to a single solvent. In certain embodiments, the solvent mixture is a mixture of an ethereal solvent and a hydrocarbon. Examplary such mixtures include, for instance, an ether/benzene mixture. Solvent mixtures may be comprised of equal volumes of each solvent or may contain one solvent in excess of the other solvent or solvents. In certain embodiments wherein a solvent mixture is comprised of two solvents, the solvents may be present in a ratio of about 20:1, about 10:1, about 9:1, about 8:1, about 7:1, about 6:1, about 5:1, about 4:1, about 3:1, about 2:1, or about 1:1. One of skill in the art would appreciate that other solvent mixtures and/or ratios are contemplated herein, that the selection of such other solvent mixtures and/or ratios will depend on factors such as the solubility of species present in the reaction (e.g., substrates, additives, etc.) and stability and activity of metal complexes, and that experimentation required to optimized the solvent mixture and/or ratio would be routine in the art and not undue.

Suitable conditions, in some embodiments, employ ambient temperatures. In some embodiments, a suitable temperature is about 15° C., about 20° C., about 25° C., or about 30° C. In some embodiments, a suitable temperature is from about 15° C. to about 25° C. In certain embodiments, a suitable temperature is about 20° C., 21° C., 22° C., 23° C., 24° C., or 25° C.

In certain embodiments, a provided method is performed at elevated temperature. In some embodiments, a suitable temperature is from about 25° C. to about 200° C. In certain embodiments, a suitable temperature is from about 40° C. to about 200° C., from about 50° C. to about 200° C., from about 60° C. to about 200° C., from about 70° C. to about 200° C., from about 80° C. to about 200° C., from about 90° C. to about 200° C., from about 40° C. to about 100° C., from about 50° C. to about 100° C., from about 60° C. to about 100° C., from about 70° C. to about 100° C., from about 80° C. to about 100° C., or from about 90° C. to about 100° C. In some embodiments, a suitable temperature is about 25° C. In some embodiments, a suitable temperature is about 30° C. In some embodiments, a suitable temperature is about 40° C. In some embodiments, a suitable temperature is about 50° C. In some embodiments, a suitable temperature is about 60° C. In some embodiments, a suitable temperature is about 70° C. In some embodiments, a suitable temperature is about 80° C. In some embodiments, a suitable temperature is about 90° C. In some embodiments, a suitable temperature is about 100° C. In some embodiments, a suitable temperature is about 110° C. In some embodiments, a suitable temperature is about 120° C. In some embodiments, a suitable temperature is about 130° C. In some embodiments, a suitable temperature is about 140° C. In some embodiments, a suitable temperature is about 150° C. In some embodiments, a suitable temperature is about 160° C. In some embodiments, a suitable temperature is about 170° C. In some embodiments, a suitable temperature is about 180° C. In some embodiments, a suitable temperature is about 190° C. In some embodiments, a suitable temperature is about 200° C. In some embodiments, a suitable temperature is greater than about 200° C.

In certain embodiments, a provided method is performed at temperature lower than ambient temperatures. In some embodiments, a suitable temperature is from about −100° C. to about 10° C. In certain embodiments, a suitable temperature is from about −80° C. to about 0° C. In certain embodiments, a suitable temperature is from about −70° C. to about 10° C. In certain embodiments, a suitable temperature is from about −60° C. to about 10° C. In certain embodiments, a suitable temperature is from about −50° C. to about 10° C. In certain embodiments, a suitable temperature is from about −40° C. to about 10° C. In certain embodiments, a suitable temperature is or from about −30° C. to about 10° C. In some embodiments, a suitable temperature is below 0° C. In some embodiments, a suitable temperature is about −100° C. or lower. In some embodiments, a suitable temperature is about −100° C. In some embodiments, a suitable temperature is about −90° C. In some embodiments, a suitable temperature is about −80° C. In some embodiments, a suitable temperature is about −70° C. In some embodiments, a suitable temperature is about −60° C. In some embodiments, a suitable temperature is about −50° C. In some embodiments, a suitable temperature is about −40° C. In some embodiments, a suitable temperature is about −30° C. In some embodiments, a suitable temperature is about −20° C. In some embodiments, a suitable temperature is about −10° C. In some embodiments, a suitable temperature is about 0° C. In some embodiments, a suitable temperature is about 10° C.

In some embodiments, a provided method is performed at different temperatures. In some embodiments, temperature changes in a provided method. In some embodiments, a provided method involves temperature increase from a lower suitable temperature to a higher suitable temperature. In some embodiments, a provided method comprises temperature increase from about −100° C. or lower, −90° C., −80° C., about −70° C., about −60° C., about −50° C., about −40° C., about −30° C., about −20° C., about −10° C., or about 0° C. to about 0° C., about 10° C., about 20° C., ambient temperature, about 22° C., about 25° C., about 30° C., about 40° C., about 50° C., about 60° C., about 70° C., about 80° C., about 90° C., about 100° C., or about 110° C. or higher. In some embodiments, a provided method comprises temperature increase from about 30° C. to 22° C. In some embodiments, a provided method comprises temperature decrease from a higher suitable temperature to a lower suitable temperature. In some embodiments, a provided method comprises temperature decrease from about 110° C. or higher, about 100° C., about 90° C., about 80° C., about 70° C., about 60° C., about 50° C., about 40° C., about 30° C., about 25° C., about 22° C., ambient temperature, about 20° C., about 10° C., or about 0° C. to about 0° C., about −10° C., about −20° C., about −30° C., about −40° C., about −50° C., about −60° C., about −70° C., about −80° C., about −90° C., or about −100° C. or lower.

Suitable conditions typically involve reaction times of about 1 second to about one or more days. In some embodiments, a reaction time ranges from less than about 1 second to about 72 hours. In some embodiments, a reaction time ranges from less than about 1 second to about 24 hours. In some embodiments, a reaction time ranges from less than about 1 second to about 12 hours. In some embodiments, a reaction time ranges from less than about 1 second to about 6 hours. In some embodiments, a reaction time ranges from less than about 1 second to about 4 hours. In some embodiments, a reaction time ranges from less than about 1 second to about 2 hours. In some embodiments, a reaction time ranges from less than about 1 second to about 60 minutes. In some embodiments, a reaction time ranges from less than about 1 second to about 50 minutes. In some embodiments, a reaction time ranges from less than about 1 second to about 40 minutes. In some embodiments, a reaction time ranges from less than about 1 second to about 30 minutes. In some embodiments, a reaction time ranges from less than about 1 second to about 20 minutes. In some embodiments, a reaction time ranges from less than about 1 second to about 10 minutes. In some embodiments, a reaction time ranges from less than about 1 second to about 9 minutes. In some embodiments, a reaction time ranges from less than about 1 second to about 8 minutes. In some embodiments, a reaction time ranges from less than about 1 second to about 7 minutes. In some embodiments, a reaction time ranges from less than about 1 second to about 6 minutes. In some embodiments, a reaction time ranges from less than about 1 second to about 5 minutes. In some embodiments, a reaction time ranges from less than about 1 second to about 4 minutes. In some embodiments, a reaction time ranges from less than about 1 second to about 3 minutes. In some embodiments, a reaction time ranges from less than about 1 second to about 2 minutes. In some embodiments, a reaction time ranges from less than about 1 second to about 60 seconds. In some embodiments, a reaction time ranges from less than about 1 second to about 60 seconds. In some embodiments, a reaction time ranges from less than about 1 second to about 50 seconds. In some embodiments, a reaction time ranges from less than about 1 second to about 40 seconds. In some embodiments, a reaction time ranges from less than about 1 second to about 30 seconds. In some embodiments, a reaction time ranges from less than about 1 second to about 20 seconds. In some embodiments, a reaction time ranges from less than about 1 second to about 10 seconds. In some embodiments, a reaction time ranges from less than about 1 second to about 5 seconds. In some embodiments, a reaction time ranges from about 0.5 hour to about 72 hours. In some embodiments, a reaction time ranges from about 0.5 hour to about 48 hours. In some embodiments, a reaction time ranges from about 0.5 hour to about 20 hours. In some embodiments, a reaction time ranges from about 0.5 hour to about 15 hours. In some embodiments, a reaction time ranges from about 1.0 hour to about 12 hours. In some embodiments, a reaction time ranges from about 1 hour to about 10 hours. In some embodiments, a reaction time ranges from about 1 hour to about 8 hours. In some embodiments, a reaction time ranges from about 1 hour to about 6 hours. In some embodiments, a reaction time ranges from about 1 hour to about 4 hours. In some embodiments, a reaction time ranges from about 1 hour to about 2 hours. In some embodiments, a reaction time ranges from about 2 hours to about 8 hours. In some embodiments, a reaction time ranges from about 2 hours to about 4 hours. In some embodiments, a reaction time ranges from about 2 hours to about 3 hours. In some embodiments, a reaction time is about 1 second. In some embodiments, a reaction time is about 5 seconds. In some embodiments, a reaction time is about 10 seconds. In some embodiments, a reaction time is about 20 seconds. In some embodiments, a reaction time is about 30 seconds. In some embodiments, a reaction time is about 40 seconds. In some embodiments, a reaction time is about 50 seconds. In some embodiments, a reaction time is about 60 seconds. In some embodiments, a reaction time is about 2 minutes. In some embodiments, a reaction time is about 5 minutes. In some embodiments, a reaction time is about 10 minutes. In some embodiments, a reaction time is about 15 minutes. In some embodiments, a reaction time is about 20 minutes. In some embodiments, a reaction time is about 25 minutes. In some embodiments, a reaction time is about 30 minutes. In some embodiments, a reaction time is about 35 minutes. In some embodiments, a reaction time is about 40 minutes. In some embodiments, a reaction time is about 45 minutes. In some embodiments, a reaction time is about 50 minutes. In some embodiments, a reaction time is about 60 minutes. In certain embodiments, a reaction time is about 1, 2, 3, 4, 5, 6, 7, 8, 9, 10, 11, 12, 24, 36, 48, 60, 72, 96 or 120 hours. In some embodiments, a reaction time is about 2 hours. In some embodiments, a reaction time is about 3 hours. In some embodiments, a reaction time is about 4 hours. In some embodiments, a reaction time is about 5 hours. In some embodiments, a reaction time is about 6 hours. In some embodiments, a reaction time is about 8 hours. In some embodiments, a reaction time is about 10 hours. In some embodiments, a reaction time is about 12 hours. In some embodiments, a reaction time is about 16 hours. In some embodiments, a reaction time is about 50 hours. In some embodiments, a reaction time is about 24 hours. In some embodiments, a reaction time is about 36 hours. In some embodiments, a reaction time is about 48 hours. In some embodiments, a reaction time is about 60 hours. In some embodiments, a reaction time is about 72 hours. In some embodiments, the reaction time is about 96 hours. In some embodiments, the reaction time is about 120 hours In some embodiments, a provided metal complex compound, e.g. a compound of formula I, II, or III, or an active catalyst formed therefrom, is stable under metathesis conditions. In some embodiments, a provided compound, or an active catalyst formed therefrom, decomposes under metathesis conditions. In some embodiments, a provided compound, or an active catalyst formed therefrom, decomposes under metathesis conditions within about 1 hour. In some embodiments, a provided compound, or an active catalyst formed therefrom, decomposes under metathesis conditions within about 2 hours. In some embodiments, a provided compound, or an active catalyst formed therefrom, decomposes under metathesis conditions within about 6 hours. In some embodiments, a provided compound, or an active catalyst formed therefrom, decomposes under metathesis conditions within about 12 hours. In some embodiments, a provided compound, or an active catalyst formed therefrom, decomposes under metathesis conditions within about 24 hours. In some embodiments, a provided compound, or an active catalyst formed therefrom, decomposes under metathesis conditions within about 48 hours. In some embodiments, a provided compound, or an active catalyst formed therefrom, decomposes under metathesis conditions within about 96 hours.

In some embodiments, a provided method requires an amount of a provided compound (e.g., a metal complex compound having the structure of formula I, II or III) such that the loading is from about 0.01 mol % to about 20 mol % of the provided compound relative to substrate (e.g., a monomer to be polymerized). In certain embodiments, a provided compound is used in an amount of between about 0.01 mol % to about 10 mol %. In certain embodiments, a provided compound is used in an amount of between about 0.01 mol % to about 6 mol %. In certain embodiments, a provided compound is used in an amount of between about 0.01 mol % to about 5 mol %. In certain embodiments, a provided compound is used in an amount of between about 0.01 mol % to about 4 mol %. In certain embodiments, a provided compound is used in an amount of between about 0.01 mol % to about 3 mol %. In certain embodiments, a provided compound is used in an amount of between about 0.01 mol % to about 1 mol %. In certain embodiments, a provided compound is used in an amount of between about 0.01 mol % to about 0.5 mol %. In certain embodiments, a provided compound is used in an amount of between about 0.01 mol % to about 0.2 mol %. In certain embodiments, a provided compound is used in an amount of about 0.05%, 0.1%, 0.2%, 0.5%, 1%, 2%, 3 mol %, 4 mol %, 5 mol %, 6 mol %, 7 mol %, 8 mol %, 9 mol %, or 10 mol %. In some embodiments, a provided metal complex compound is used in an amount of about 0.05%. In some embodiments, a provided metal complex compound is used in an amount of about 0.1%. In some embodiments, a provided metal complex compound is used in an amount of about 0.2%. In some embodiments, a provided metal complex compound is used in an amount of about 0.3%. In some embodiments, a provided metal complex compound is used in an amount of about 0.4%. In some embodiments, a provided metal complex compound is used in an amount of about 0.5%. In some embodiments, a provided metal complex compound is used in an amount of about 1%. In some embodiments, a provided metal complex compound is used in an amount of about 2%. In some embodiments, a provided metal complex compound is used in an amount of about 3%. In some embodiments, a provided metal complex compound is used in an amount of about 4%. In some embodiments, a provided metal complex compound is used in an amount of about 5%. In some embodiments, a provided metal complex compound is used in an amount of about 6%. In some embodiments, a provided metal complex compound is used in an amount of about 7%. In some embodiments, a provided metal complex compound is used in an amount of about 8%. In some embodiments, a provided metal complex compound is used in an amount of about 9%. In some embodiments, a provided metal complex compound is used in an amount of about 10%. In some embodiments, a provided metal complex compound is used in an amount of about 15%. In some embodiments, a provided metal complex compound is used in an amount of about 20%.

In some embodiments, a method of the present invention requires an amount of solvent such that the concentration of the reaction is between about 0.01 M and about 1 M. In some embodiments, the concentration of the reaction is between about 0.01 M and about 0.5 M. In some embodiments, the concentration of the reaction is between about 0.01 M and about 0.1 M. In some embodiments, the concentration of the reaction is between about 0.01 M and about 0.05 M. In some embodiments, the concentration of the reaction is about 0.01 M. In some embodiments, the concentration of the reaction is about 0.02 M. In some embodiments, the concentration of the reaction is about 0.03 M. In some embodiments, the concentration of the reaction is about 0.04 M. In some embodiments, the concentration of the reaction is about 0.05 M. In some embodiments, the concentration of the reaction is about 0.1 M. In some embodiments, the concentration of the reaction is about 0.3 M.

In some embodiments, a method of the present invention is performed at ambient pressure. In some embodiments, a method of the present invention is performed at reduced pressure. In some embodiments, a method of the present invention is performed at a pressure of less than about 20 torr. In some embodiments, a method of the present invention is performed at a pressure of less than about 15 torr. In some embodiments, a method of the present invention is performed at a pressure of less than about 10 torr. In some embodiments, a method of the present invention is performed at a pressure of about 9, 8, 7, 6, 5, 4, 3, 2, or 1 torr. In certain embodiments, a method of the present invention is performed at a pressure of about 7 torr. In certain embodiments, a method of the present invention is performed at a pressure of about 1 torr.

In some embodiments, a method of the present invention is performed at increased pressure. In some embodiments, a method of the present invention is performed at greater than about 1 atm. In some embodiments, a method of the present invention is performed at greater than about 2 atm. In some embodiments, a method of the present invention is performed at greater than about 3 atm. In some embodiments, a method of the present invention is performed at greater than about 5 atm. In some embodiments, a method of the present invention is performed at greater than about 10 atm. In some embodiments, a method of the present invention is performed at about 2 atm. In some embodiments, a method of the present invention is performed at about 3 atm. In some embodiments, a method of the present invention is performed at about 5 atm. In some embodiments, a method of the present invention is performed at about 10 atm.

It will be appreciated that, in certain embodiments, each variable recited is as defined above and described in embodiments, herein, both singly and in combination.

In some embodiments, the present invention provides the following exemplary embodiments:

1. A poly(dicyclopentadiene) polymer, wherein the polymer is greater than 80% syndiotactic.
2. The polymer of example 1, wherein double bonds in the polymer backbone is greater than 90% cis.
3. The polymer of any one of the preceding examples, wherein double bonds in the polymer backbone is greater than 95% cis.
4. A hydrogenated poly(dicyclopentadiene) polymer, wherein the polymer is greater than 80% syndiotactic.
5. The polymer of anyone of the preceding examples, wherein the polymer is greater than 85% syndiotactic.
6. The polymer of any one of the preceding claims, wherein the polymer is greater than 90% syndiotactic.
7. The polymer of any one of the preceding claims, wherein the polymer is greater than 95% syndiotactic.
8. The polymer of any one of the preceding examples, wherein the polymer is greater than 97% syndiotactic.
9. The polymer of any one of the preceding examples, wherein the polymer is greater than 99% syndiotactic.
10. The polymer of any one of the preceding examples, wherein $M_n$ of the polymer is greater than about 5,000.
11. A composition comprising a polymer of any one of the preceding examples.
12. The composition of example 11, further comprising a tungsten salt, $R^4$—H, $R^5$—H, $R^{5'}$—H, or one of more neutral ligands independently selected from $R^8$ or $R^9$.

13. The composition of example 11, further comprising a tungsten salt, $R^{5'}$—H, or one of more neutral ligands independently selected from $R^8$ or $R^9$.

14. The composition of example 11, further comprising a tungsten salt, $R^4$—H, or $R^5$—H.

15. The composition of example 11, further comprising $R^4$—H.

16. The composition of example 11, further comprising $R^5$—H.

17. The composition of example 11, further comprising a tungsten salt, $R^4$—H, and $R^5$—H.

18. The composition of example 11, further comprising a tungsten salt.

19. A compound of formula I:

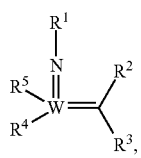

wherein:

$R^1$ is —$C(R^{1a})_3$;

each $R^{1a}$ is independently an optionally substituted group selected from $C_{1-10}$ aliphatic, $C_{1-10}$ heteroalkyl having 1-3 heteroatoms independently selected from nitrogen, oxygen or sulfur, phenyl, a 3-7 membered saturated or partially unsaturated carbocyclic ring, an 8-10 membered bicyclic or polycyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; or:

two $R^{1a}$ groups are optionally taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur; or:

three $R^{1a}$ groups are optionally taken together with the carbon atom to which they are attached to form an optionally substituted 4-10 membered, bicyclic or polycyclic, saturated or partially unsaturated ring having 0-4 heteroatoms independently selected from nitrogen, oxygen or sulfur;

each of $R^2$ and $R^3$ is independently —R, —OR, —SR, —N(R)$_2$, —OC(O)R, —S(O)R, —SO$_2$R, —SO$_2$N(R)$_2$, —C(O)N(R)$_2$, —NRC(O)R, or —NRSO$_2$R; or:

$R^2$ and $R^3$ are optionally taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur;

each R is independently hydrogen or an optionally substituted group selected from $C_{1-10}$ aliphatic, $C_{1-10}$ heteroalkyl having 1-3 heteroatoms independently selected from nitrogen, oxygen or sulfur, phenyl, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; or:

two R groups are optionally taken together with the intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen or sulfur;

$R^4$ is optionally substituted 5-14 membered heteroaryl having 1-4 heteroatoms independently selected from nitrogen, oxygen or sulfur, wherein at least one heteroatom is nitrogen;

$R^5$ is —OAr$^a$; and

Ar$^a$ is optionally substituted

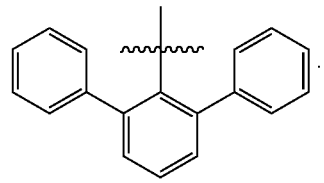 [SMILES: *c1c(-c2ccccc2)cccc1-c1ccccc1]

20. The compound of example 19, wherein each $R^{1a}$ is optionally substituted $C_{1-6}$ aliphatic or phenyl.

21. The compound of example 19 or 20, wherein $R^1$ is

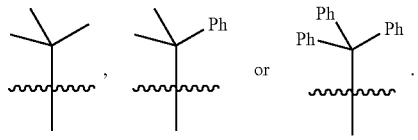

22. The compound of example 19 or 20, wherein $R^1$ is

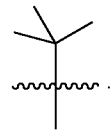 [SMILES: *C(C)(C)C]

23. The compound of example 19, wherein two $R^{1a}$ groups are taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur.

24. The compound of example 19 or 23, wherein $R^1$ is

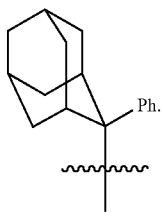 [SMILES: *C1(c2ccccc2)C2CC3CC(C2)CC1C3]

25. The compound of example 19, wherein three $R^{1a}$ groups are optionally taken together with the carbon atom to which they are attached to form an optionally substituted 4-10 membered, bicyclic or polycyclic, saturated or partially unsaturated ring having 0-4 heteroatoms independently selected from nitrogen, oxygen or sulfur.

26. The compound of example 19 or 25, wherein $R^1$ is

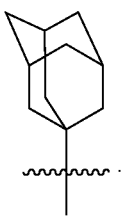

27. The compound of example 19, wherein $R^1$ is

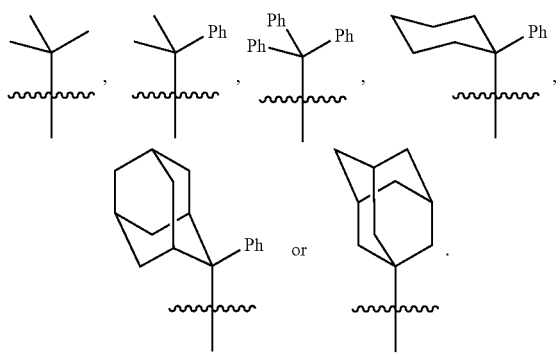

28. A compound of formula II:
wherein:

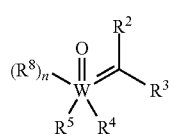

each of $R^2$ and $R^3$ is independently —R, —OR, —SR, —N(R)$_2$, —OC(O)R, —S(O)R, —SO$_2$R, —SO$_2$N(R)$_2$, —C(O)N(R)$_2$, —NRC(O)R, or —NRSO$_2$R; or:

$R^2$ and $R^3$ are optionally taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur;

each R is independently hydrogen or an optionally substituted group selected from $C_{1-10}$ aliphatic, $C_{1-10}$ heteroalkyl having 1-3 heteroatoms independently selected from nitrogen, oxygen or sulfur, phenyl, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; or:

two R groups are optionally taken together with the intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen or sulfur;

$R^4$ is optionally substituted 5-14 membered heteroaryl having 1-4 heteroatoms independently selected from nitrogen, oxygen or sulfur, wherein at least one heteroatom is nitrogen;

$R^5$ is —OAr$^a$;

Ar$^a$ is optionally substituted

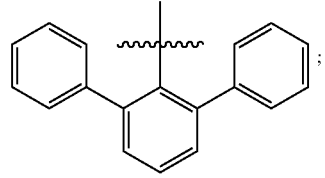 [SMILES: *c1c(-c2ccccc2)cccc1-c1ccccc1]

n is 0-2; and each $R^8$ is independently a phosphorus-containing ligand, wherein the phosphorus-containing ligand is bonded to W through a phosphorus atom.

29. The compound of example 28, wherein the compound of formula II has the structure of formula II-a:

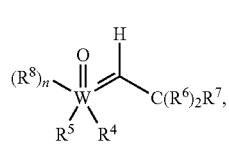

wherein:

$R^4$ is optionally substituted 5-14 membered heteroaryl having 1-4 heteroatoms independently selected from nitrogen, oxygen or sulfur, wherein at least one heteroatom is nitrogen;

$R^5$ is —OAr$^a$;

Ar$^a$ is optionally substituted

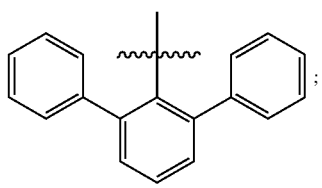 [SMILES: *c1c(-c2ccccc2)cccc1-c1ccccc1]

each R$^6$ is independently —R, —OR, —SR, —N(R)$_2$, —OC(O)R, —S(O)R, —SO$_2$R, —SO$_2$N(R)$_2$, —C(O)N(R)$_2$, —NRC(O)R, or —NRSO$_2$R;

each R is independently hydrogen or an optionally substituted group selected from C$_{1-10}$ aliphatic, C$_{1-10}$ heteroalkyl having 1-3 heteroatoms independently selected from nitrogen, oxygen or sulfur, phenyl, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; or:

two R groups are optionally taken together with the intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen or sulfur;

R$^7$ is optionally substituted phenyl;

n is 0-2; and each R$^8$ is independently a phosphorus-containing ligand, wherein the phosphorus-containing ligand is bonded to W through a phosphorus atom.

30. The compound of example 29, wherein each R$^6$ is independently optionally substituted C$_{1-6}$ alkyl, and R$^7$ is optionally substituted phenyl.

31. The compound of example 29 or 30, wherein each R$^6$ is methyl and R$^7$ is phenyl.

32. The compound of any one of examples 28-31, wherein n is 1.

33. The compound of any one of examples 28-32, wherein each R$^8$ is independently a compound having the structure of P(R)$_3$.

34. The compound of any one of examples 28-32, wherein n is 0.

35. The compound of any one of examples 19-34, wherein R$^4$ is an optionally substituted 5-membered heteroaryl ring having 1-4 heteroatoms independently selected from nitrogen, oxygen or sulfur, wherein at least one heteroatom is nitrogen.

36. The compound of any one of examples 19-35, wherein the at least one heteroatom is nitrogen, and the nitrogen is directly bond to tungsten.

37. The compound of any one of examples 19-36, wherein R$^4$ is optionally substituted

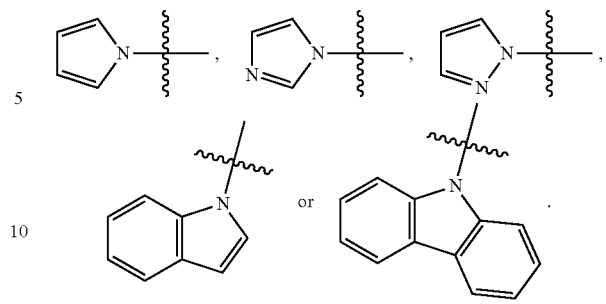

38. The compound of any one of examples 19-37, wherein R$^4$ is optionally substituted

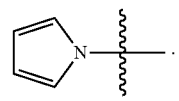 [SMILES: *n1cccc1]

39. The compound of any one of examples 19-38, wherein R$^4$ is

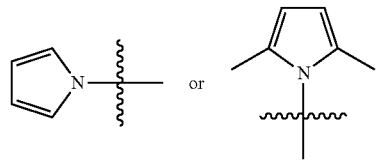

40. The compound of any one of examples 19-39, wherein R$^5$ is substituted

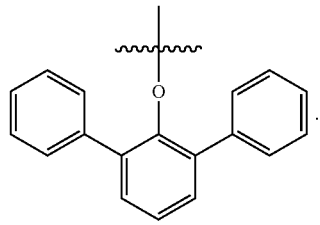 [SMILES: *Oc1c(-c2ccccc2)cccc1-c1ccccc1]

41. The compound of any one of examples 19-40, wherein R$^5$ is substituted

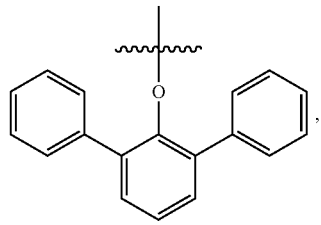 [SMILES: *Oc1c(-c2ccccc2)cccc1-c1ccccc1]

wherein each of the 2', 2", 6' and 6" positions is independently substituted.

42. The compound of any one of examples 19-41, wherein R$^5$ is —O-2,6-(Mesityl)$_2$C$_6$H$_3$ or —O-2,6-(C$_6$F$_5$)$_2$C$_6$H$_3$.

43. The compound of any one of examples 19-41, wherein $R^5$ is

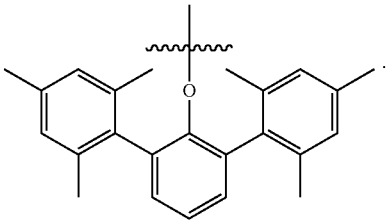

44. A compound of formula III:
wherein:

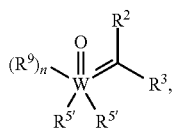

III each of $R^2$ and $R^3$ is independently —R, —OR, —SR, —N(R)$_2$, —OC(O)R, —S(O)R, —SO$_2$R, —SO$_2$N(R)$_2$, —C(O)N(R)$_2$, —NRC(O)R, or —NRSO$_2$R; or:
  $R^2$ and $R^3$ are optionally taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur;
each R is independently hydrogen or an optionally substituted group selected from $C_{1-10}$ aliphatic, $C_{1-10}$ heteroalkyl having 1-3 heteroatoms independently selected from nitrogen, oxygen or sulfur, phenyl, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; or:
  two R groups are optionally taken together with the intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen or sulfur;
each $R^{5'}$ is independently —OAr$^b$;
Ar$^b$ is

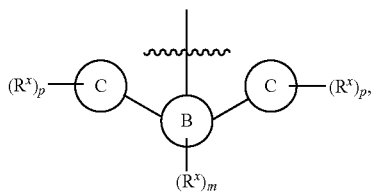

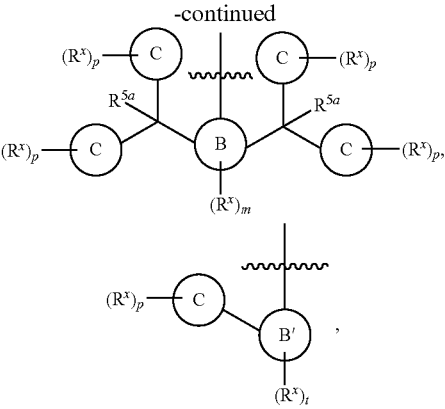

or an optionally substituted group selected from phenyl, a 10-14 membered bicyclic or polycyclic aryl ring, a 5-6 membered monocyclic heteroaryl ring having 1-4 heteroatoms independently selected from nitrogen, oxygen or sulfur, or an 8-14 membered bicyclic or polycyclic heteroaryl ring having 1-5 heteroatoms independently selected from nitrogen, oxygen or sulfur;
Ring B is an optionally substituted group selected from phenyl or a 5-6 membered monocyclic heteroaryl ring having 1-4 heteroatoms independently selected from nitrogen, oxygen or sulfur;
Ring B' is an optionally substituted group selected from phenyl, a 10-14 membered bicyclic or tricyclic aryl ring, a 5-6 membered monocyclic heteroaryl ring having 1-4 heteroatoms independently selected from nitrogen, oxygen or sulfur, or an 8-14 membered bicyclic or tricyclic heteroaryl ring having 1-5 heteroatoms independently selected from nitrogen, oxygen or sulfur;
each Ring C is independently an optionally substituted group selected from phenyl, a 3-7 membered saturated or partially unsaturated carbocyclic ring, an 6-14 membered bicyclic or tricyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-14 membered bicyclic or tricyclic heteroaryl ring having 1-5 heteroatoms independently selected from nitrogen, oxygen or sulfur;
each $R^x$ is independently R, halogen, —CN, —C(O)R, —C(O)OR, —C(O)N(R)$_2$, —C(O)N(R)(OR), —OR, —OC(O)R, —OC(O)N(R)$_2$, —OSi(R)$_3$, —SR, —S(O)R, —S(O)$_2$R, —S(O)$_2$OR, —S(O)$_2$N(R)$_2$, —NO$_2$, —N(R)$_2$, —NROR, —NRC(O)R, —N(R)C(O)OR, —N(R)C(O)N(R)$_2$, —N(R)S(O)$_2$R, —N(R)S(O)$_2$N(R)$_2$, —P(R)$_2$, —P(OR)$_2$, —P(O)(R)$_2$, —P(O)(OR)$_2$, —P(O)[N(R)$_2$]$_2$, or —Si(R)$_3$;
each $R^{5a}$ is independently R;
each of p and t is independently 0-7;
m is 0-3;
n is 0-2; and
each $R^9$ is independently a neutral ligand.

45. The compound of example 44, wherein n is 0.

46. The compound of example 44 or 45, wherein each Ar$^b$ is independently

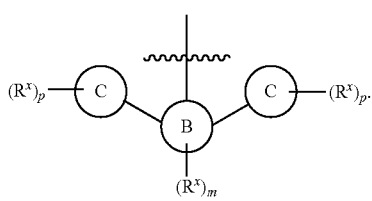

47. The compound of any one of examples 44-46, wherein each $Ar^b$ is independently optionally substituted

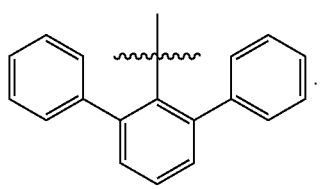 [SMILES: *c1c(-c2ccccc2)cccc1-c1ccccc1]

48. The compound of any one of examples 44-47, wherein $Ar^b$

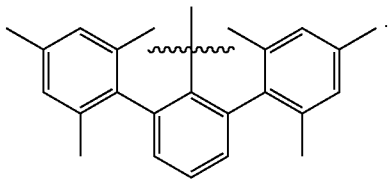

49. The compound of any one of examples 44-48, wherein the compound is coordinated to a Lewis acid.

50. The compound of any one of examples 44-49, wherein the compound is coordinated to a Lewis acid having the structure of $B(R)_3$.

51. The compound of any one of examples 34-40, wherein the compound is coordinated to $B(C_6F_5)_3$.

52. The compound of any one of examples 19-51, wherein one of $R^2$ and $R^3$ is hydrogen, and the other is optionally substituted $C_{1-4}$ alkyl.

53. The compound of any one of examples 19-52, wherein one of $R^2$ and $R^3$ is hydrogen, and the other is t-butyl.

54. The compound of any one of examples 19-52, wherein one of $R^2$ and $R^3$ is hydrogen, and the other is —$C(Me)_2Ph$.

55. The composition of any one of examples 12, 14, 15 or 17, wherein $R^4$ is an optionally substituted 5-membered heteroaryl ring having 1-4 heteroatoms independently selected from nitrogen, oxygen or sulfur, wherein at least one heteroatom is nitrogen.

56. The composition of any one of examples 12, 14, 15 or 17, wherein $R^4$ is optionally substituted

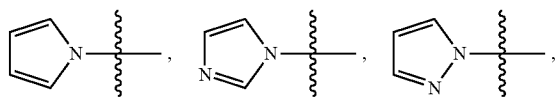

57. The composition of any one of examples 12, 14, 15 or 17, wherein $R^4$ is optionally substituted

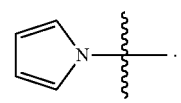

58. The composition of any one of examples 12, 14, 15 or 17, wherein $R^4$ is

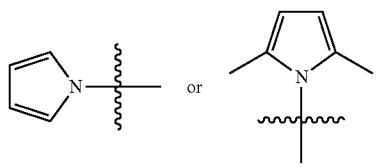

59. The composition of any one of examples 12, 14, 16, 17 or 55-58, wherein the composition comprises $R^5$—H, wherein $R^5$ is substituted

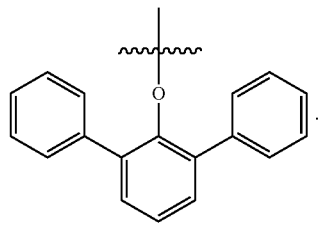 [SMILES: *Oc1c(-c2ccccc2)cccc1-c1ccccc1]

60. The composition of any one of examples 12, 14, 16, 17 or 55-59, wherein the composition comprises $R^5$—H, wherein $R^5$ is substituted

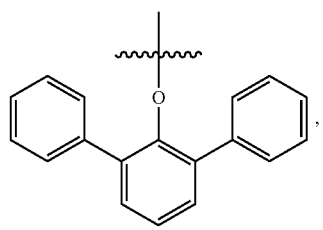 [SMILES: *Oc1c(-c2ccccc2)cccc1-c1ccccc1]

wherein each of the 2', 2", 6' and 6" positions is independently substituted.

61. The composition of any one of examples 12, 14, 16, 17 or 55-60, wherein the composition comprises $R^5$—H, wherein $R^5$ is —O-2,6-(Mesityl)$_2C_6H_3$ or —O-2,6-($C_6F_5$)$_2C_6H_3$.

62. The composition of any one of examples 12, 14, 16, 17 or 55-61, wherein the composition comprises R⁵—H, wherein R⁵ is

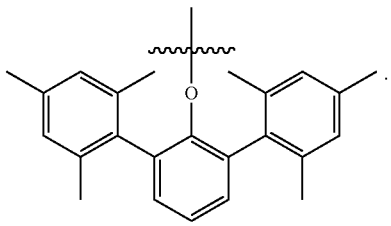

63. The composition of any one of examples 12-14, 17-18 and 55-62, wherein the composition comprises a tungsten salt, wherein the tungsten salt is a compound of any one of examples 19-54.
63. The composition of any one of examples 12-14, 17-18 and 55-62, wherein the composition comprises a tungsten salt, wherein the tungsten salt is a compound of any one of examples 19-54.
63. The composition of any one of examples 12-14, 17-18 and 55-62, wherein the composition comprises a tungsten salt, wherein the tungsten salt is a compound of a quenched product of any one of examples 19-54 after metathesis.
64. A method for preparing a polymer of any one of examples 1-10, comprising a step of:
   a) providing a compound of any one of examples 19-54.
65. A method for preparing a composition of any one of examples 11-18 and 55-63, comprising a step of:
   a) providing a compound of any one of examples 19-54.
66. The method of example 64 or 65, wherein the compound is a compound of formula I.
67. The method of example 64 or 65, wherein the compound is a compound of formula II.
68. The method of example 64 or 65, wherein the compound is a compound of formula III.
69. The method of example 68, further comprising a step of:
   a2) providing a Lewis acid.
70. The method of example 69, wherein the Lewis acid comprises boron.
71. The method of example 69 or 70, wherein the Lewis acid is B(R)₃.
72. The method of any one of examples 69-71, wherein the Lewis acid is B(C₆F₅)₃.
73. The method of example 64, 65 or 66, wherein the catalyst is compound 5.
74. The method of example 64, 65 or 67, wherein the catalyst is compound 12.
75. The method of 64, 65 or 68, wherein the catalyst is compound 13.
76. The method of any one of examples 64-75, further comprising steps of:
   b) providing dicyclopentadiene; and
   c) polymerizing the provided dicyclopentadiene in the presence of the provided compound of any one of examples 19-54 to provide the polymer.
77. The method of any one of examples 64-76, further comprising a step of:
   d) hydrogenating the provided highly syndiotactic poly (DCPD) to provide highly syndiotactic hydrogenated poly (DCPD).
78. A method for performing ring opening metathesis polymerization ("ROMP") with high syndiotactic selectivity, wherein the monomeric substrate is highly reactive, comprising a step of:
   a) providing a compound of any one of examples 19-54.
79. The method of example 78, wherein the monomeric substrate is endo-dicyclopentadiene.
80. The method of example 78 or 79, wherein the compound has the structure of formula I.
81. The method of example 78 or 79, wherein the compound has the structure of formula II.
82. The method of example 78 or 79, wherein the compound is a compound of formula III, further comprising a step of:
   b) optionally providing a Lewis acid.
83. A method for improving the tactic selectivity of ROMP, comprising a step of:
   a) providing a Lewis acid.
84. The method of example 83, wherein the ROMP comprising providing a compound of formula III.
85. The method of example 84, wherein the compound of formula III is a compound of any one of examples 44-48 and 52-54.
86. The method of any one of examples 82-85, wherein the Lewis acid comprises boron.
87. The method of any one of examples 82-86, wherein the Lewis acid is B(R)₃.
88. The method of any one of examples 82-87, wherein the Lewis acid is B(C₆F₅)₃.

EXEMPLIFICATION

Polymers with certain stereoregularity, for example, highly syndiotactic poly(DCPD) and hydrogenated poly (DCPD), are particularly challenging to make. Among other things, the present invention provides polymers with high stereoregularity, compositions thereof, and compounds and methods for preparing the same. Non-limiting examples are depicted herein.

As a byproduct in the steam cracking of gas oils, dicyclopentadiene (DCPD) is co-produced in large quantities, turning the compound into one of the cheapest technically relevant monomers for ring-opening metathesis polymerization (ROMP)[1,2,3,4]. In some embodiments, the formation of linear ROMP derived poly(dicyclopentadiene) (poly (DCPD)) proceeds via the exclusive opening of the strained norbornene ring as illustrated in FIG. 1[5,6].

[1] T. Oshika, H. Tabuchi, *Bull. Chem. Soc. Jpn.*, 1968, 41, 211.
[2] C. Z. Winstein, *Chem. Abstr.*, 1977, 86, 122050n.
[3] D. W. Klosiewicz, U.S. Pat. No. 4,657,981, 1987.
[4] K. J. Ivin, J. C. Mol, *Olefin Metathesis and Metathesis Polymerization*, Academic Press, London, 1997.
[5] T. A. Davidson, K. B. Wagener, D. B. Priddy, *Macromolecules*, 1996, 29, 786.

Figure 2:
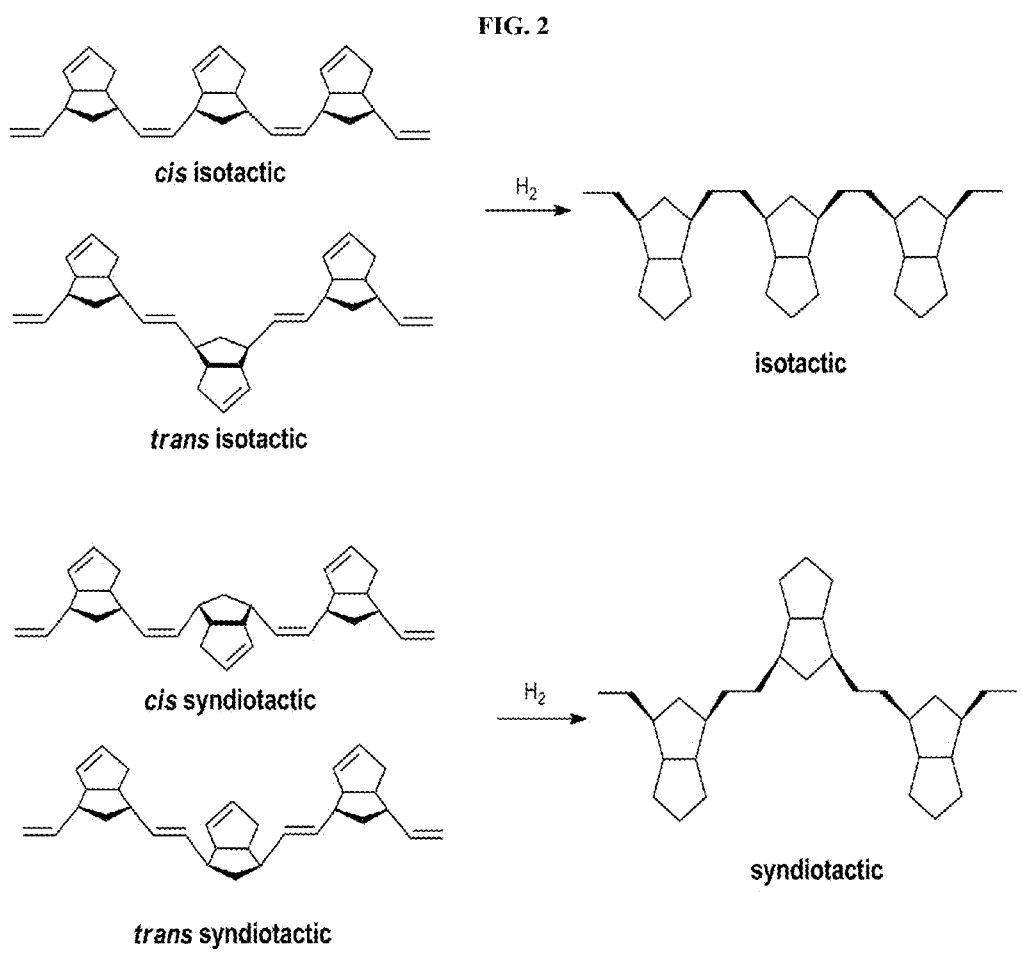
FIG. 2. Possible structural elements of poly(DCPD) and hydrogenated poly(DCPD).

In industry most often classical catalyst systems, composed of a transition metal halide and a main group metal cocatalyst such as the system WCl₆/Et₂AlCl are used[3]. The thus synthesized poly(DCPD) is entirely crosslinked as a consequence of both, ring-opening metathesis and olefin addition polymerization[5]. Generally, the double bond geometry and the crosslink density of the resulting poly(DCPD) is determined by the catalyst system used for its preparation. Neglecting head-to-tail versus head-to-head orientation of the monomer units, in case of ROMP derived poly(DCPD)s there are two steric structural factors (cis/trans and meso/racemo) in the polymer main chain (FIG. 2)[8,9,10,11]. Some physical properties of a polymer significantly depend on its microstructure; it is thus crucial being capable of precisely controlling the above mentioned stereochemical factors during synthesis of the material. Mo, W and Ru complexes are capable of promoting metathesis[12,13,14,15,16,17,18,19,20], including ROMP of endo-dicyclopentadiene[9,10,21,22,23], and other substituted norbornenes[9,10,12,13,14,15,17,18,24,25]. Despite all the efforts, highly syndiotactic poly(DCPD) or hydrogenated poly (DCPD) could not be obtained prior to the present invention, and the polymerization process could be slow. In some embodiments, the present invention provides stereoselective ROMP of endo-dicyclopentadiene initiated by well defined W and Mo alkylidene complexes, giving access to highly-structured poly(DCPD), including highly syndiotactic poly(DCPD), at high rates.

[6] T. A. Davidson, K. B. Wagener, *J. Mol. Catal. A: Chem.*, 1998, 133, 67.
[7] A. Pacreau, M. Fontanille, Makromol. *Chem.*, 1987, 188, 2585.
[8] J. G. Hamilton, K. J. Ivin, J. J. Rooney, *J. Mol. Catal. A: Chem*, 1988, 36, 115.
[9] S. Hayano, H. Kurakata, D. Uchida, M. Sakamoto, N. Kishi, H. Matsumoto, Y. Tsunogae, I. Igarashi, *Chem. Lett.*, 2003, 32, 670.
[10] S. Hayano, Y. Takeyama, Y. Tsunogae, I. Igarashi, *Macromolecules*, 2006, 39, 4663.
[11] M. Lindmark-Hamberg, K. B. Wagener, *Macromolecules*, 1987, 20, 2949.
[12] H. Jeong, D. J. Kozera, R. R. Schrock, S. J. Smith, J. Zhang, N. Ren, M. A. Hillmyer, *Organometallics*, 2013, 32, 4843.
[13] M. M. Flook, A. J. Jiang, R. R. Schrock, A. H. Hoveyda, *J. Am. Chem. Soc.*, 2009, 131, 7962.
[14] R. R. Schrock, *Dalton Trans*, 2011, 40, 7484.
[15] M. M. Flook, J. Borner, S. M. Kilyanek, L. C. H. Gerber, R. R. Schrock, *Organometallics*, 2012, 31, 6231.
[16] L. E. Rosebrugh, V. M. Marx, B. K. Keitz, R. H. Grubbs, *J. Am. Chem. Soc.*, 2013, 135, 10032.
[17] M. M. Flook, L. C. H. Gerber, G. T. Debelouchina, R. R. Schrock, *Macromolecules*, 2010, 43, 7515.
[18] M. M. Flook, V. W. L. Ng, R. R. Schrock, *J. Am. Chem. Soc.*, 2011, 133, 1784.
[19] B. K. Keitz, A. Fedorov, R. H. Grubbs, *J. Am. Chem. Soc.*, 2012, 134, 2040.
[20] S. Kobayashi, L. M. Pitet, M. A. Hillmyer, *J. Am. Chem. Soc.*, 2011, 133, 5794.
[21] S. Hayano, Y. Tsunogae, *Chem. Lett.*, 2005, 34, 1520.
[22] S. Hayano, H. Kurakata, Y. Tsunogae, Y. Nakayama, Y. Sato, H. Yasuda, *Macromolecules*, 2003, 36, 7422.
[23] S. Hayano, Y. Tsunogae, *Chem. Lett.*, 2008, 37, 518.
[24] R. R. Schrock, A. H. Hoveyda, *Angew. Chem. Int. Ed.*, 2003, 42, 4592.
[25] J. Yuan, R. R. Schrock, L. C. H. Gerber, P. Müller, S. Smith, *Organometallics*, 2013, 32, 2983.

Preparation of poly(DCPD)

Figure 12:
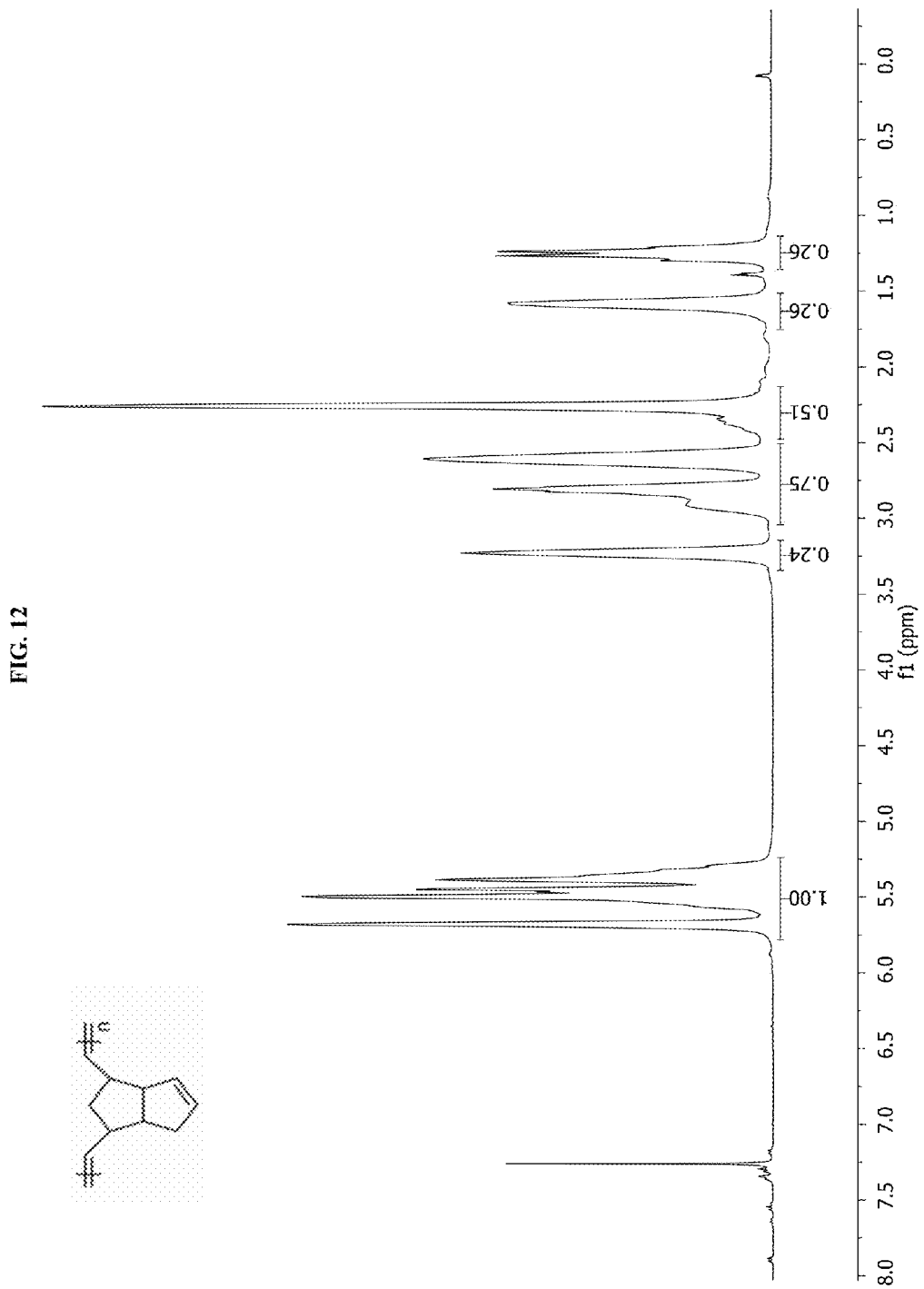
FIG. 12. $^1$H NMR (CDCl$_3$) of linear poly(DCPD) derived by the reaction of compound 1. The ratio of the olefinic to the aliphatic region is 1:2.
Figure 13:
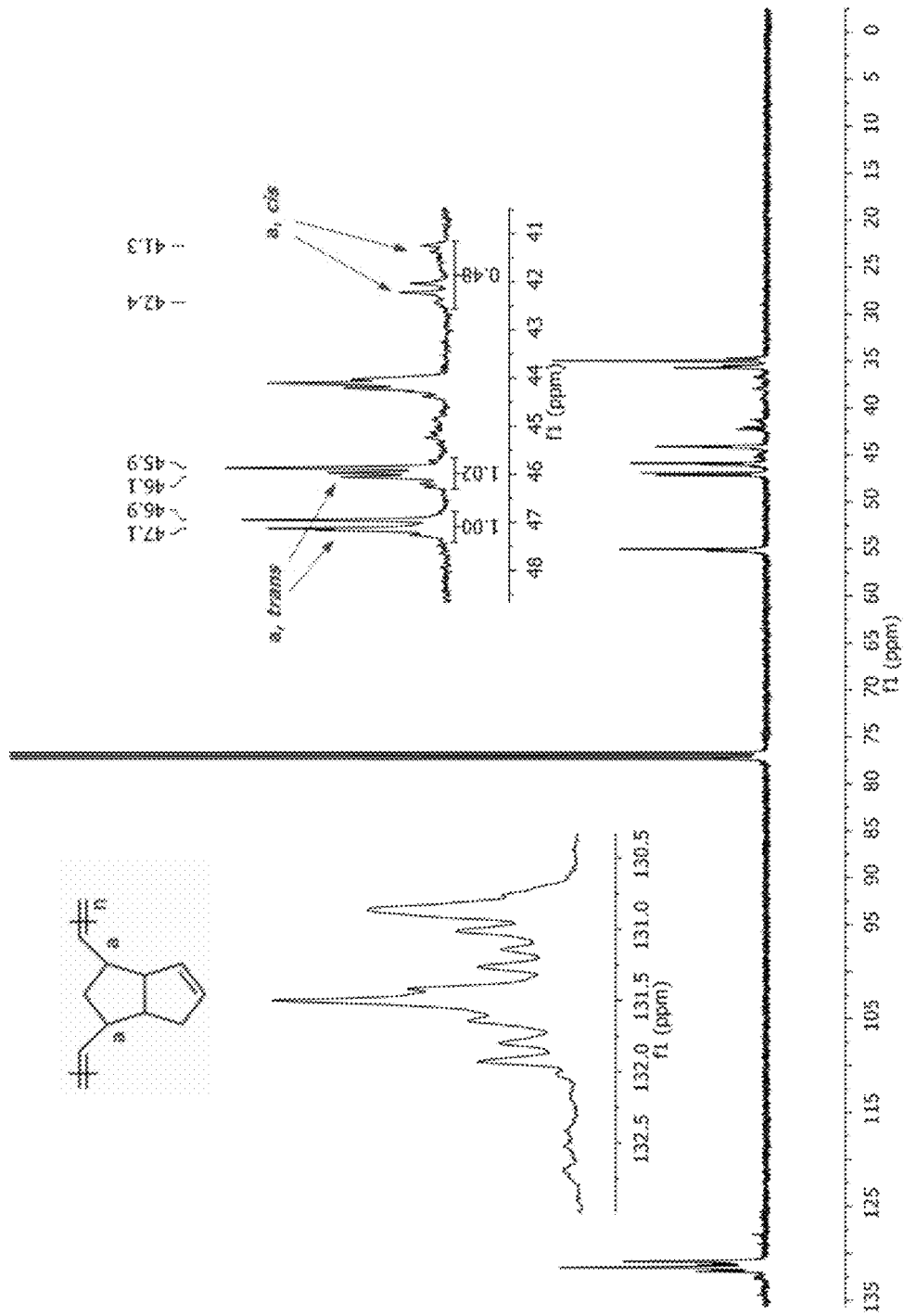
FIG. 13. $^{13}$C NMR (CDCl$_3$) of atactic poly(DCPD) derived by the reaction of compound 1.
Figure 14:
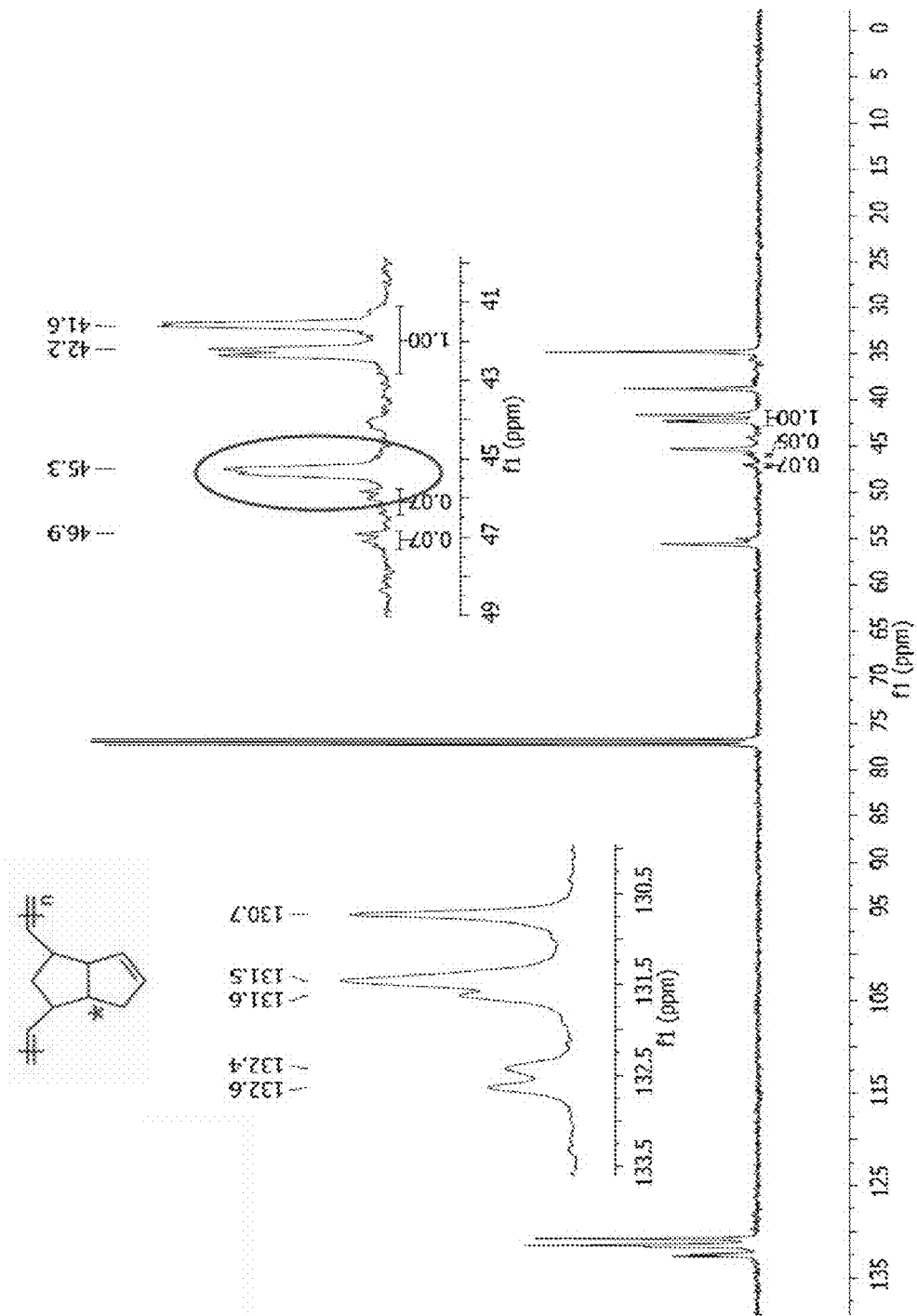
FIG. 14. $^{13}$C NMR (CDCl$_3$) of 90% cis, >95% isotactic poly(DCPD) derived by the reaction of compound 2. The doublet for C* at 45.4/45.3 ppm is indicative for a cis, isotactic structure.
Figure 15:
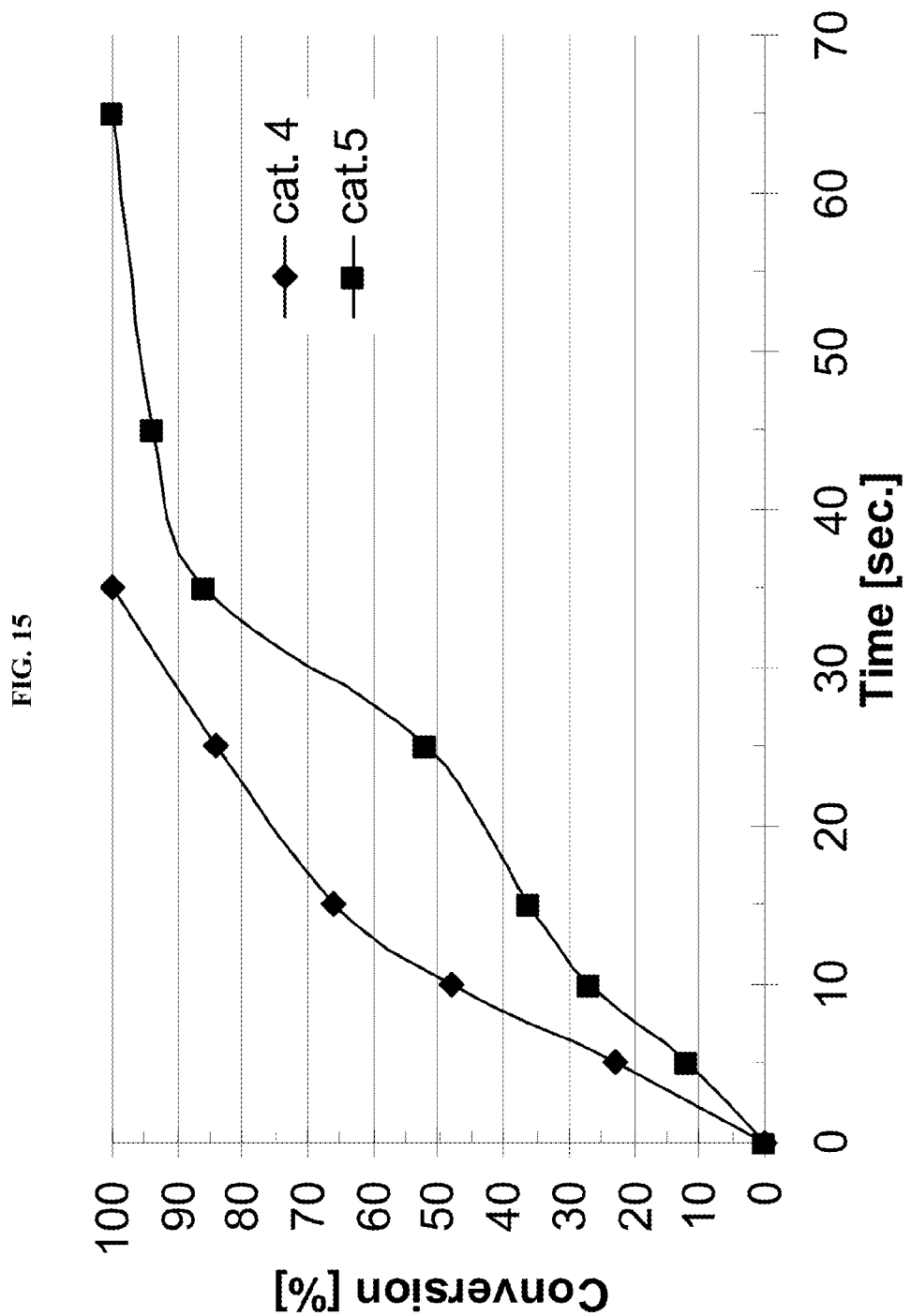
FIG. 15. Polymerization of 100 equiv. DCPD by Mo complex 4 and W complex 5 at room temperature in CH$_2$Cl$_2$.
Figure 16:
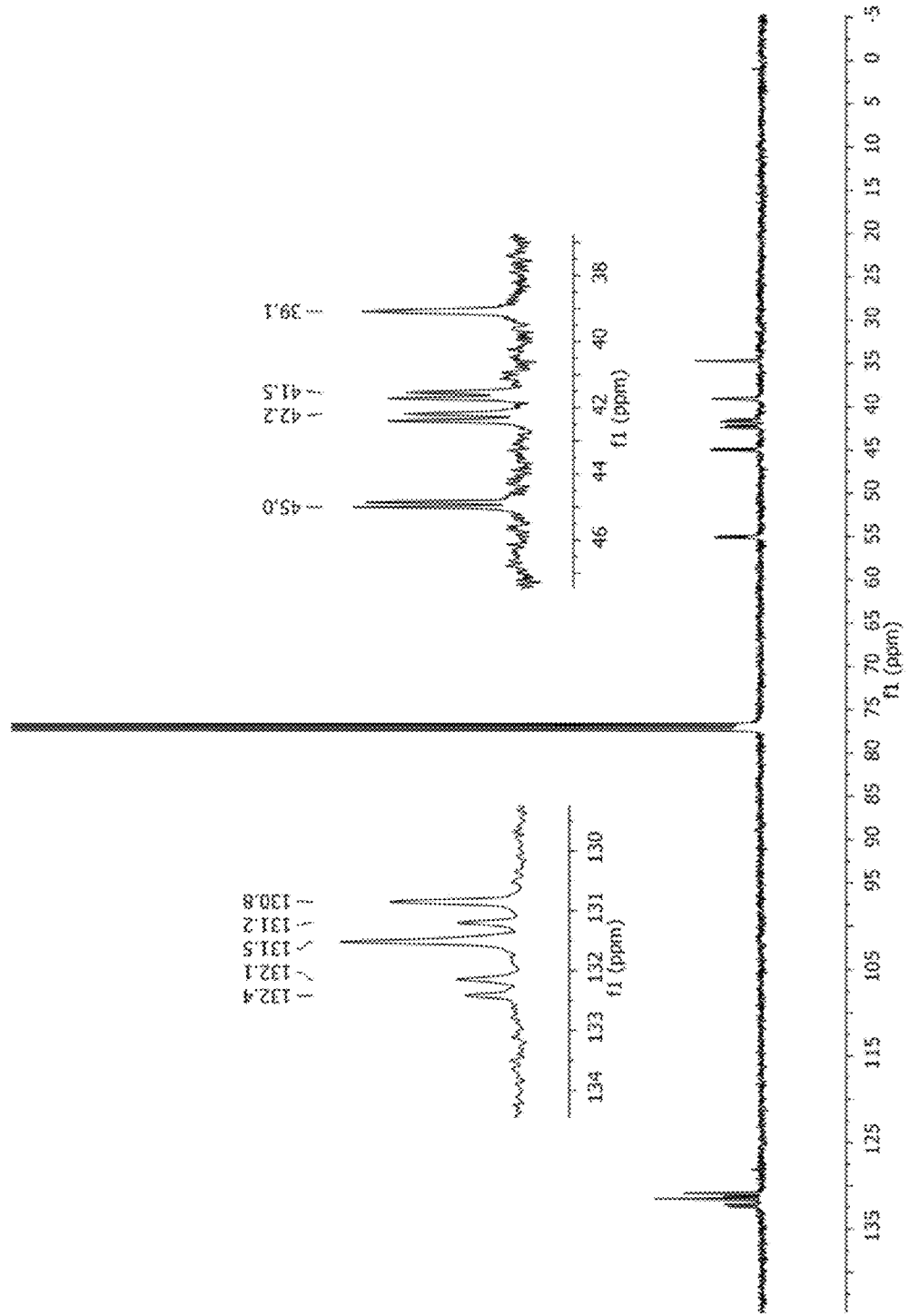
FIG. 16. $^{13}$C NMR (CDCl$_3$) of 100% cis, 100% syndiotactic poly(DCPD) derived by the reaction of compound 12. The doublet for C* at 45.0/44.9 ppm is indicative for a cis, syndiotactic structure.

Catalysts in FIG. 3 were tested for ROMP of DCPD. All catalysts quantitatively polymerized 200 equivalents of monomer at high rates (see Table 1). molybdenum based monoaryloxide monopyrrolide (MAP) complexes 6 and 7 yielded insoluble, without the intention to be limited by theory, probably cross-linked polymers, whereas the other catalysts provided soluble, linear poly(DCPD)s. Linearity of the polymer was proven by integration of the olefinic region to the aliphatic region in the $^1$H NMR spectrum. Ideally the ratio is 4:8, respectively (for an example see FIG. 12). The molybdenum based bis-tert-butoxide complex 1 gave an atactic, highly soluble polymer, which shall serve as a reference for the more tactic polymers generated by the other catalysts. The polymer exhibited 80% trans double bonds in the polymer backbone and the atacticity caused a quite complex NMR spectrum (for $^{13}$C NMR see FIG. 13). In comparison, the spectrum of poly(DCPD) derived by biphenolate complex 2 was much clearer. The polymer was possessing 90% cis double bonds in its backbone and was >95% isotactic. This finding was in accordance with previous reports[9,26,27]. ROMP of DCPD mediated by 2 proceeded at high rates; 100 equivalents of monomer were polymerized within less than 30 seconds at room temperature. Poly (DCPD) derived by 2 was less soluble than the atactic polymer yielded by 1. In case 200 equiv. DCPD were polymerized by 2, the resulting polymer was soluble in CHCl$_3$ only upon heating to 50° C. The $^{13}$C NMR spectra of polymers theoretically made up of 50 monomer units and those made up of 200 monomer units were virtually identical. This finding was true for all catalysts 1-5 and 8 and implied that the resulting polymer structures were reproducible and independent from the molecular weight of the poly(DCPD)s.

[26] R. R. Schrock, J. K. Lee, R. O'Dell, J. H. Oskam, *Macromolecules*, 1995, 28, 5933.
[27] R. O'Dell, D. H. McConville, G. E. Hofmeister, R. R. Schrock, *J. Am. Chem. Soc.*, 1994, 116, 3414.

Tungsten based MAP catalyst 3 bearing the bulky HIPTO ligand [HIPTO=O-2,6-(2,4,6-(i-Pr)$_3$C$_6$H$_2$)$_2$C$_6$H$_3$] produced a polymer that is made up of over 80% cis double bonds in its backbone and was 70% syndiotactic. Catalyst 3 is providing the lowest rates of all initiators given in FIG. 3; 100 equivalents of monomer were converted within 60 minutes. Without the invention to be limited by theory, the low rates may contribute to a loss of selectivity. The molybdenum based MAP complexes 4 and 8 bearing the somewhat smaller HMTO ligand showed even less stereoselectivity. Catalyst 4 is giving a polymer showing 68% cis configuration, and the polymer yielded by 8 is made up of 62% cis double bonds. Both polymers are atactic with racemo:meso ratios close to 1:1. The ROMP of DCPD induced by 4 and 8 proceed at very high rates; at room temperature 100 equivalents of monomer are converted within less than 30 seconds. Without the intention to be limited by theory, the very high reaction rates may compensate the stereoselectivity induced by stereogenic metal control and thus inversion of the stereogenic metal center after each insertion step.

Figure 4:
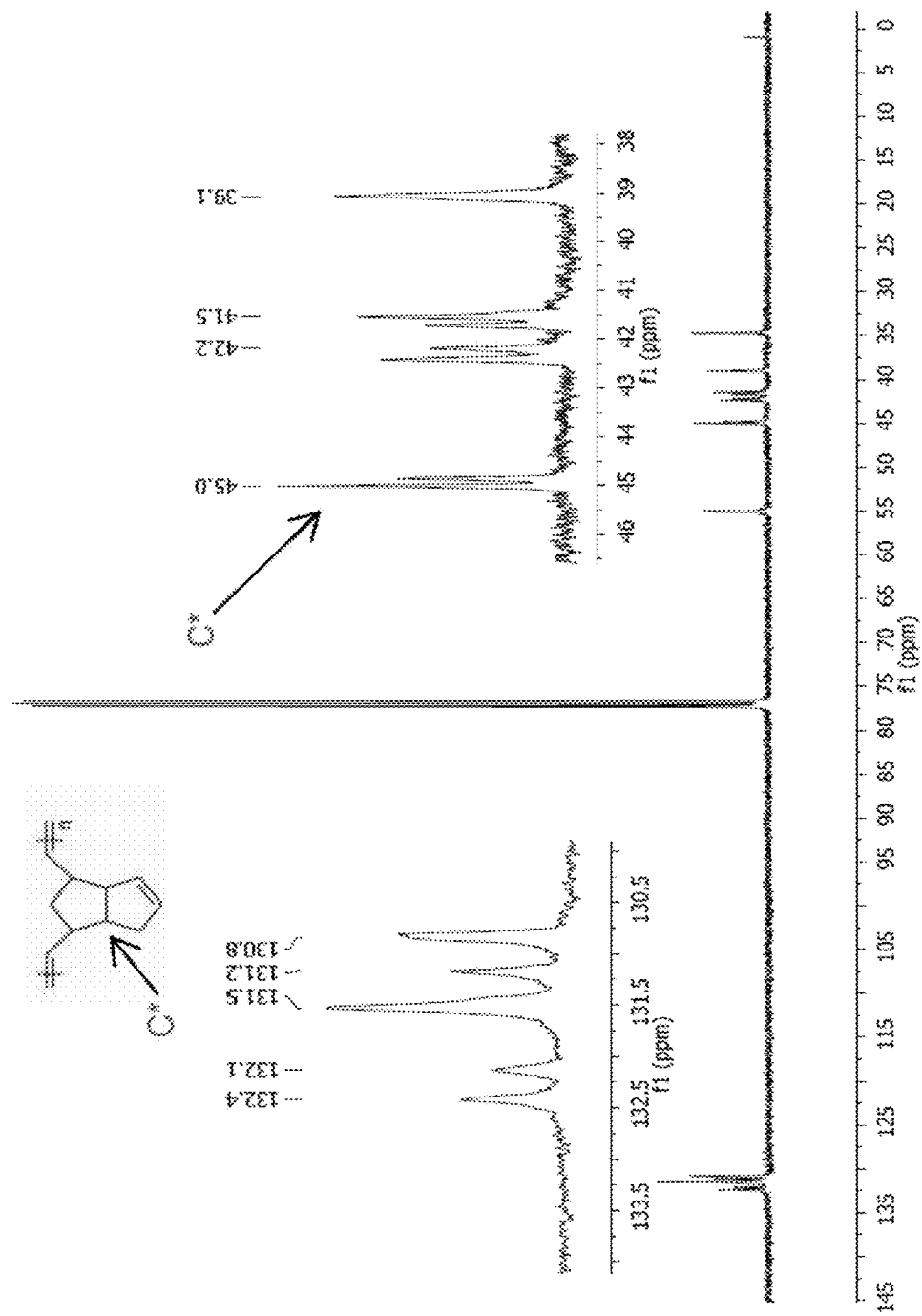
FIG. 4. $^{13}$C NMR (CDCl$_3$) of 100% cis, 100% syndiotactic poly(DCPD) derived by the reaction of compound 5. The doublet for C* at 45.0/44.9 ppm is indicative for a cis, syndiotactic structure.

It is surprisingly found that compounds of formula I, for example, compound 5, promoted ROMP with high syndiotacticity. ROMP of DCPD with 5 proceeded quickly, and yielded a 100% cis configured, 100% syndiotactic material[8,28] polymer (FIG. 4). Without the intention to be limited by theory, Applicant proposes that the combination of a tertiary alkyl R$^1$ group and the aryloxide R$^5$ group may be responsible for the observed results.

Figure 5:
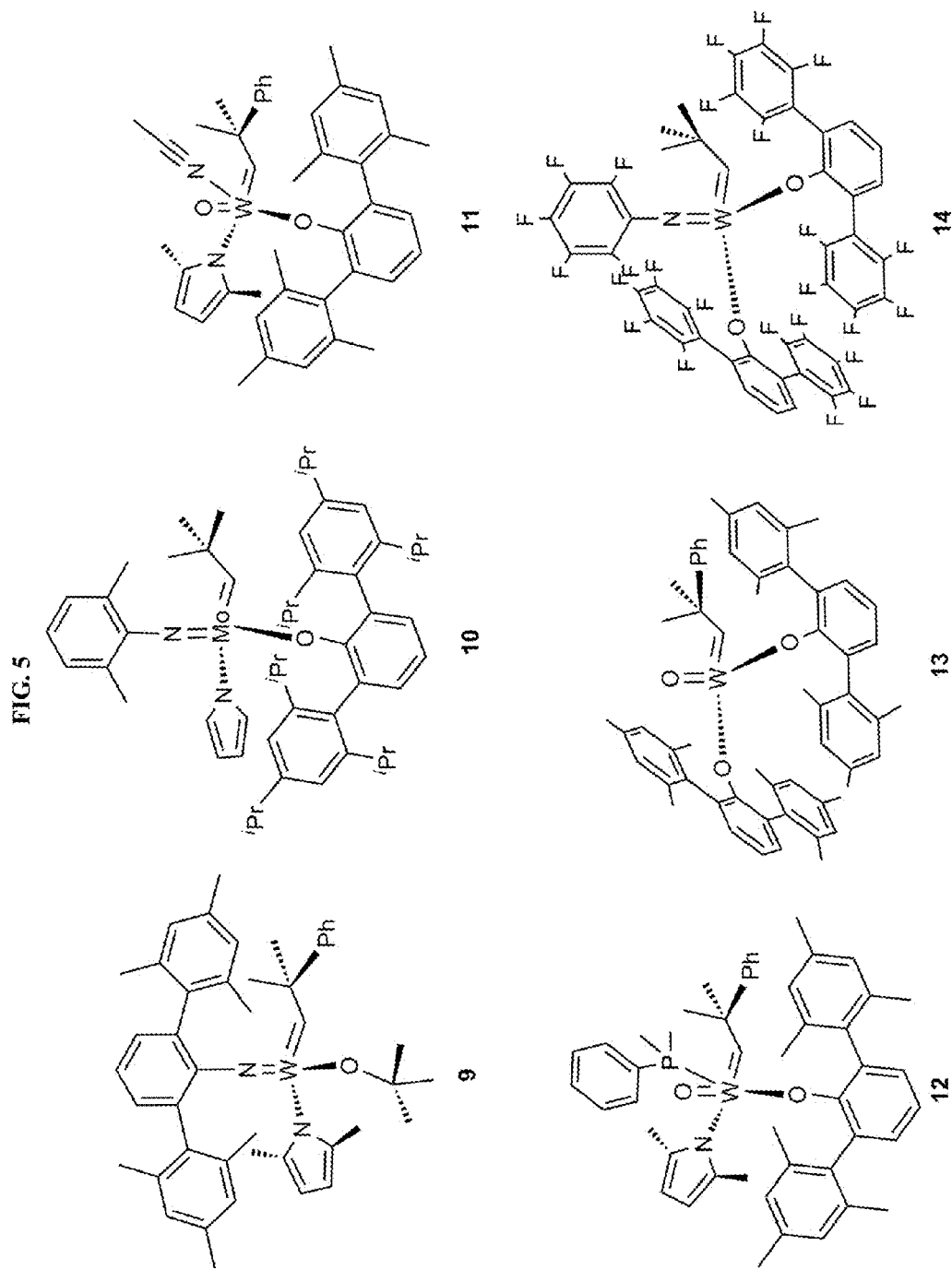
FIG. 5. Exemplary metal complex compounds.

More metal complexes were tested (FIG. 5). Unexpectedly, compounds of formula II, for example, compound 12, provided 100% cis configured, 100% syndiotactic poly (DCPD), thus providing another method for preparing highly syndiotactic poly(DCPD). Without the intention to be limited by theory, it is proposed that the combination of the small oxo group and the aryloxide group in a compound of formula II may be responsible for the observed high rates and high syndiotactic selectivity.

[28] J. G. Hamilton, K. J. Ivin, J. J. Rooney, *Brit. Polym. J.*, 1984, 16, 21.

Figure 6:
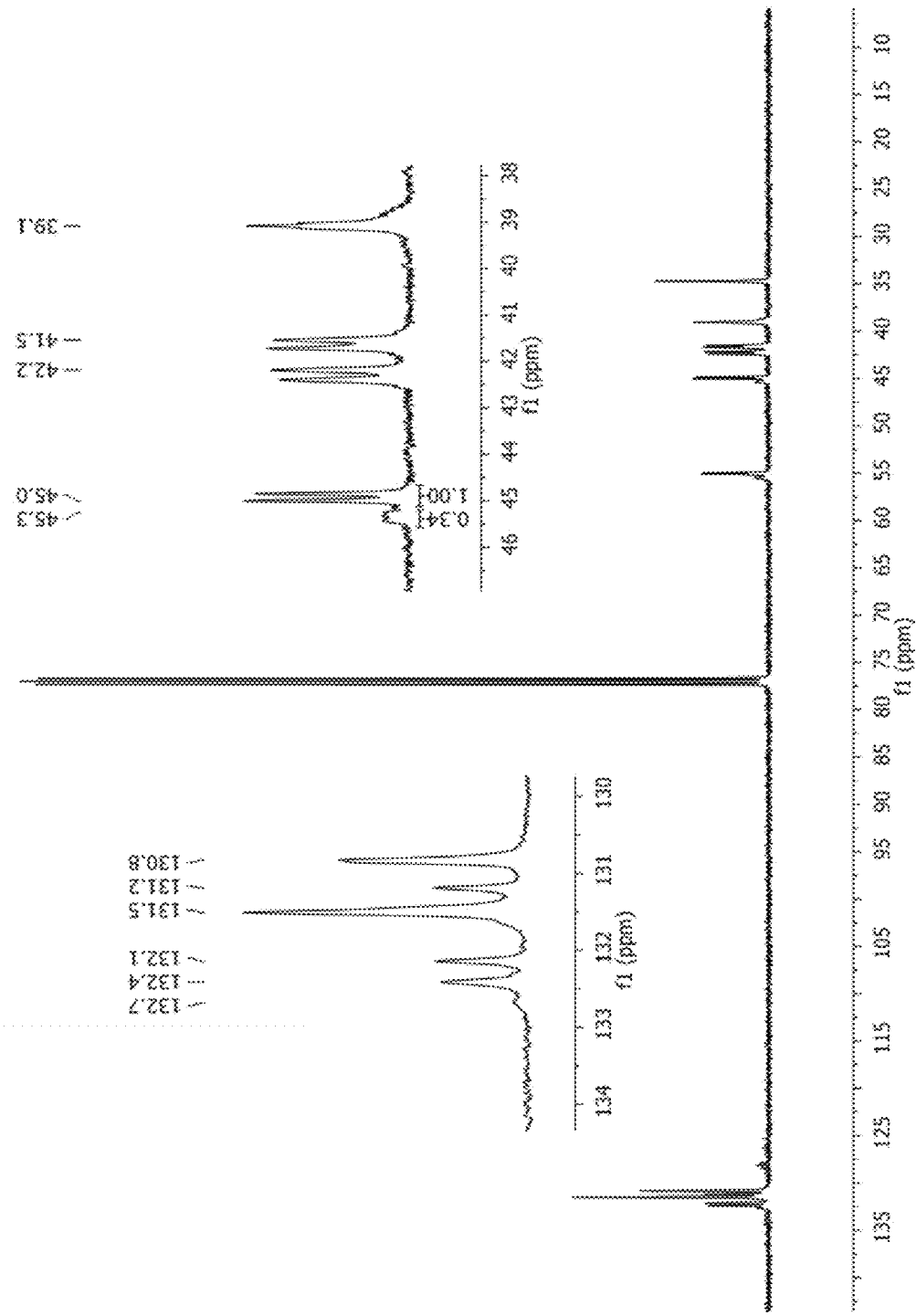
FIG. 6. $^{13}$C NMR (CDCl$_3$) of 100% cis, 75% syndiotactic poly(DCPD) derived by the reaction of compound 11. The doublet for C* at 45.0/44.9 ppm is indicative for a cis, syndiotactic structure; the doublet at 45.4/45.3 ppm is indicative for a cis, isotactic structure.

In comparison, poly(DCPD) prepared with compound 9 is atactic showing 56% trans double bonds in its backbone. At room temperature 10 produces an atactic polymer possessing a fraction of 60% cis double bonds in its backbone. Compound 11 provided 100% cis configured polymers with about 75% syndiotacticity at room temperature (FIG. 6). Without the intention to be limited by theory, the relatively low syndiotacticity may be due to stronger coordination of the acetonitrile ligand to the tungsten center: phosphine dissociation can be fast and irreversible at the time scale of the ROMP reaction. Reaction with compound 11 was performed at variable temperatures. It was found that at a temperature of 30° C. the syndioselectivity went up to 83%. However, at a temperature of 50° C. an atactic, though 100% cis-configured polymer was yielded. Without the intention to be limited by theory, the increased stereoselectivity at 30° C. might be attributed to a more rapid loss of acetonitrile; at 50° C. the enhanced reactivity causes the loss of syndioselectivity. For comparison complex 5 was used at 50° C., too. Again, a 100% cis-configured but atactic polymer was yielded. Not to be limited by theory, the maintained cis-selectivity indicated the absences of alkylidene rotation, and that a small axial and a large aryloxide ligand contribute to the cis-selectivity. At elevated temperature the monomer, without the intention to be limited by theory, may not selectively approach trans to the pyrrolide ligand at each insertion step causing the loss of syndioselectivity.

Figure 7:
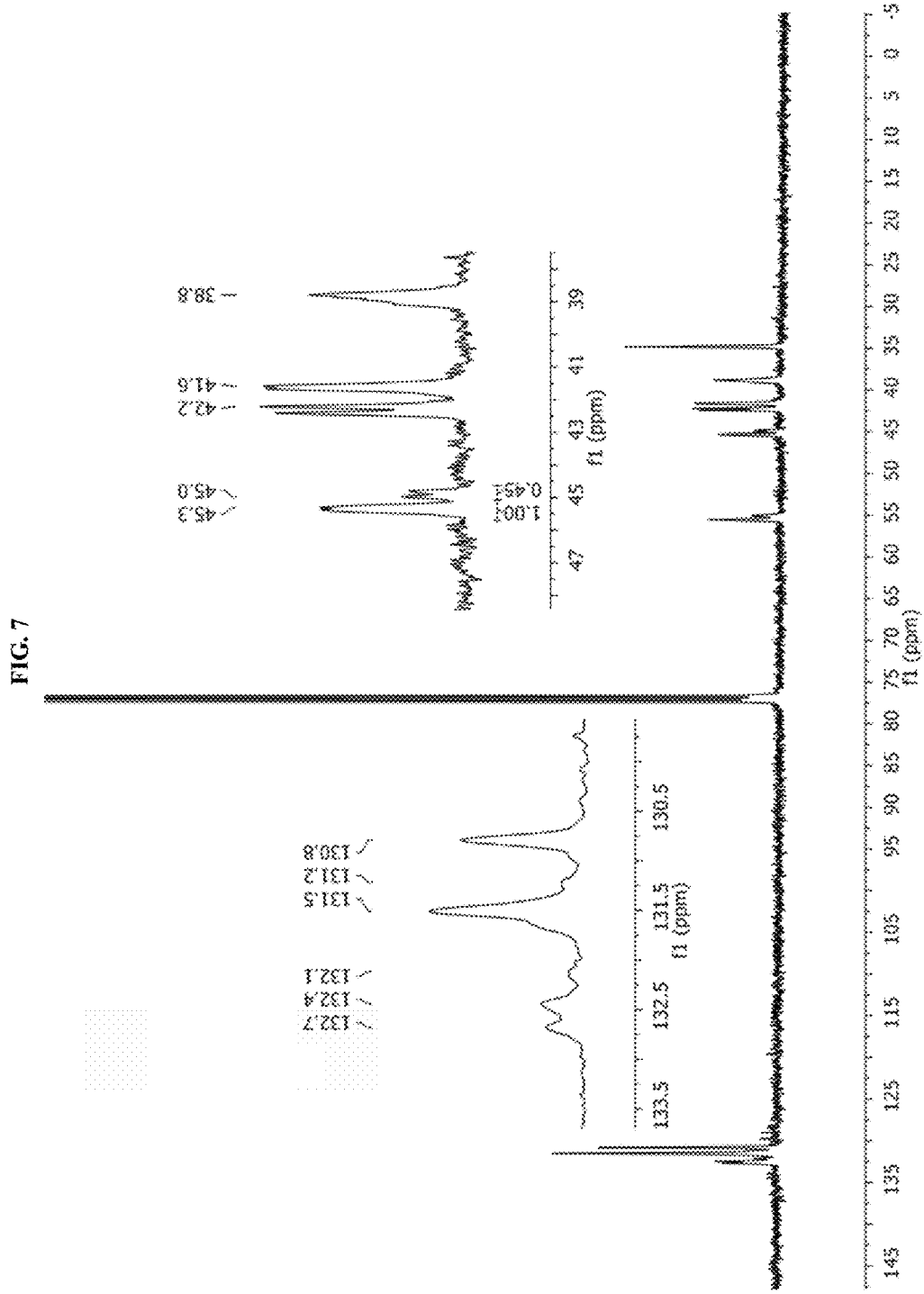
FIG. 7. $^{13}$C NMR (CDCl$_3$) of 100% cis, 70% isotactic poly(DCPD) derived by the reaction of compound 14. The doublet for C* at 45.4/45.3 ppm is indicative for a cis, isotactic structure; the doublet at 45.0/44.9 ppm is indicative for a cis, syndiotactic structure.

Both bis-alkoxide complexes 13 and 14 yielded poly (DCPD) that possess 100% cis double bonds in their backbones. W(O)(CHCMe$_2$Ph)(OHMT)$_2$ 13 shows a relatively low activity, 50 equivalents of monomer are converted within 30 minutes, and this particular catalyst provided a polymer that is 70% syndiotactic. In contrast, when applying W(N—C$_6$F$_5$)(CHCMe$_2$Ph)(ODFT)$_2$ 14 the reaction was terminated after 30 seconds. FIG. 7 shows the $^{13}$C NMR spectrum of a 70% isotactic poly(DCPD) sample derived by the reaction of 14.

In some embodiments, the present invention provides a method for improving syndiotactic selectivity of ROMP, and yet another method for preparing highly syndiotactic polymer. Much to our surprise, when a Lewis acid, for example, B(C$_6$F$_5$)$_3$, was added, compound 13 provided poly(DCPD) with about 100% syndiotactic selectivity, a dramatic, unexpected increase from about 70%.

Figure 8:
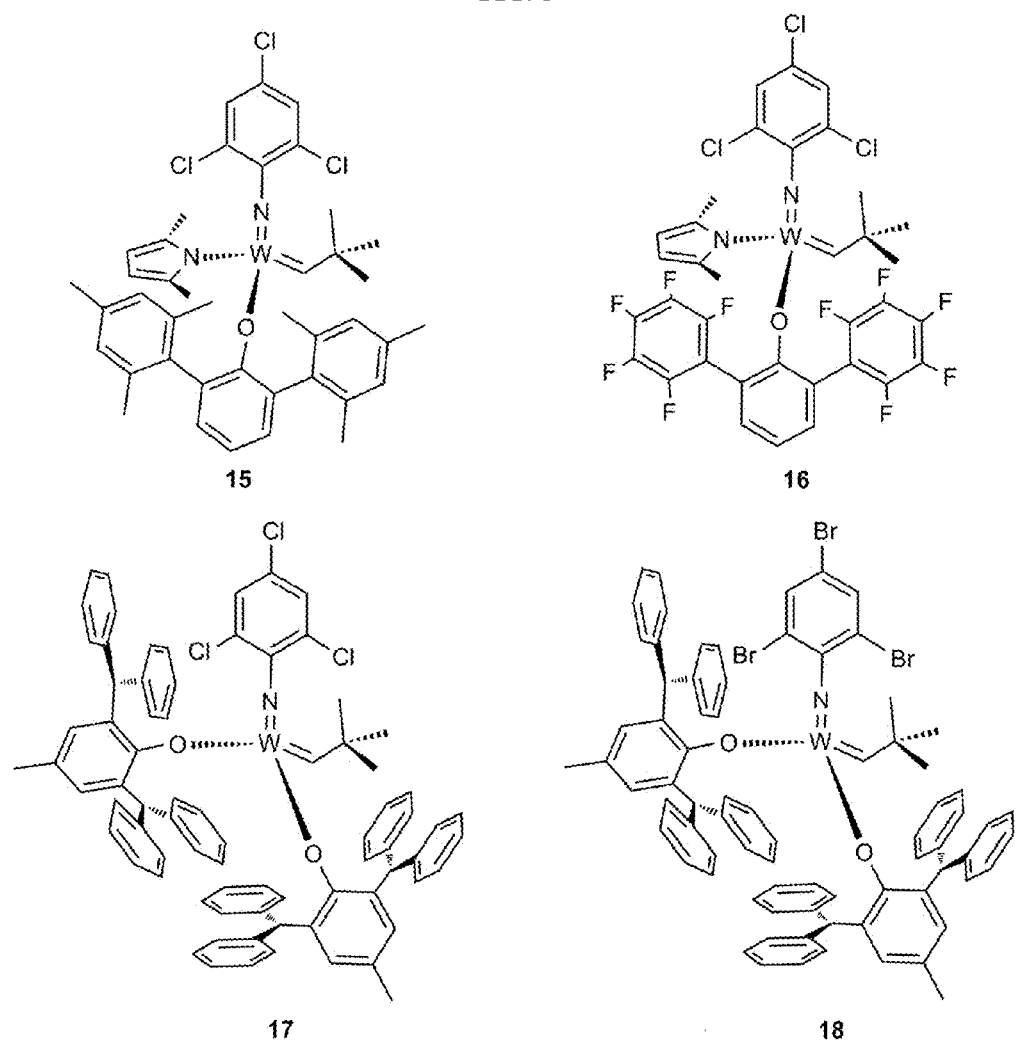
FIG. 8. Exemplary metal complex compounds.
Figure 17:
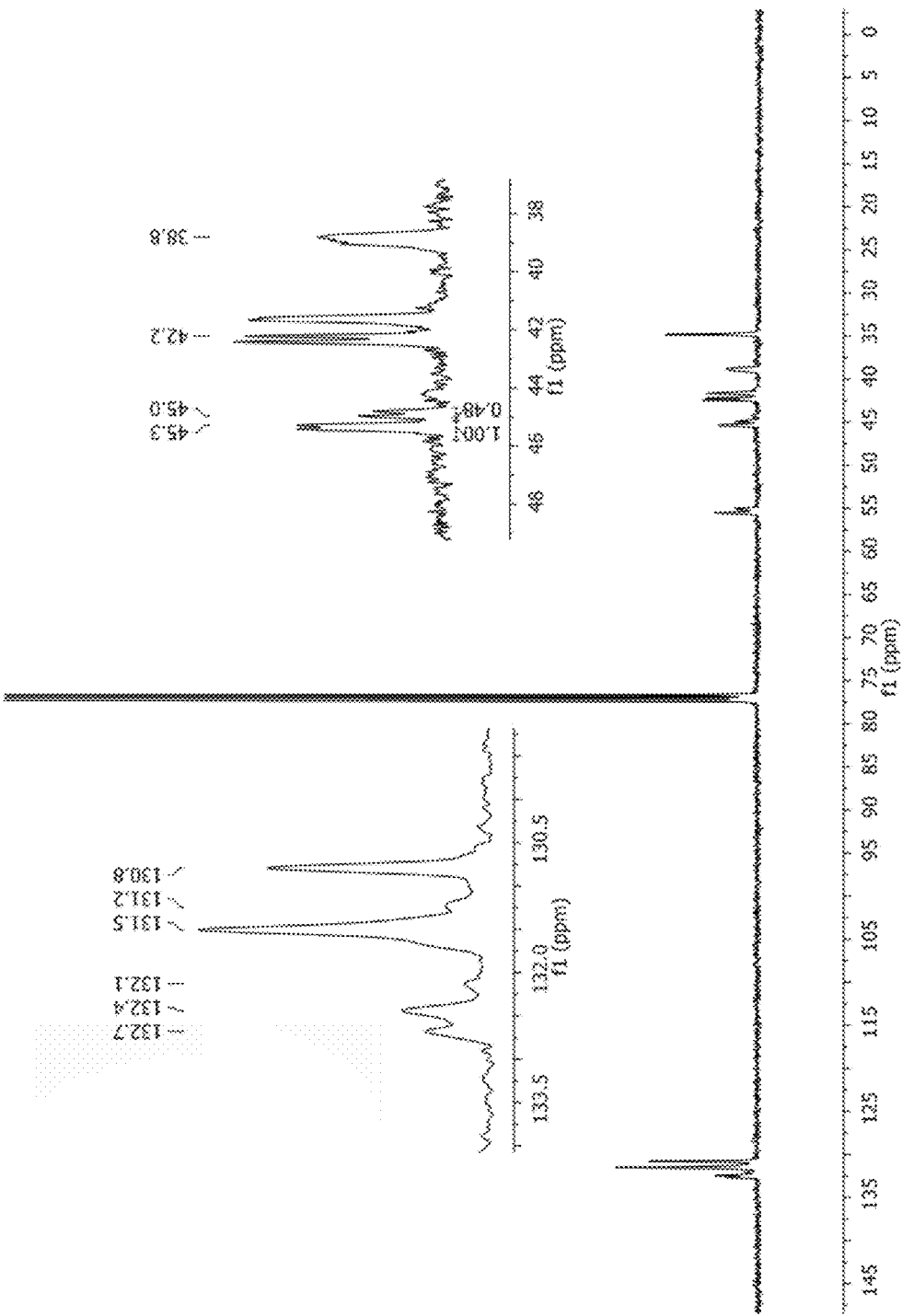
FIG. 17. $^{13}$C NMR (CDCl$_3$) of 100% cis, 70% isotactic poly(DCPD) derived by the reaction of compound 17. The doublet for C* at 45.4/45.3 ppm is indicative for a cis, isotactic structure; the doublet at 45.0/44.9 is indicative for a cis, syndiotactic structure.

Compounds 15-18 were also tested (FIG. 8). MAP catalyst 15 yielded a polymer that is about 90% cis. The reaction is fast but does not proceed as controlled as in case of than analog complexes 5 and 12. Catalyst 16 provided a polymer that is all cis configured but is atactic; the meso:racemo ratio was found to be 34:66. Poly(DCPD) generated by catalyst W(N-2,4,6-Cl$_3$Ph)(CHCMe$_2$Ph)(O-2,6-((C$_6$H$_5$)CH)$_2$C$_6$H$_3$)$_2$ 17 virtually resembles the one prepared by the reaction of 14. The polymer has a 100% cis configuration and is 70% isotactic (FIG. 17). Complex 18 differs from 17 in that its phenylimido ligand is bromo substituted in 2, 4 and 6 positions. The reaction proceeds faster and the resulting polymer is bearing a fraction of 19% trans double bonds in its backbone, the meso:racemo ratio is reduced to 63:37. Without the intention to be limited by theory, this finding might be attributed to the more bulky imido ligand compared to its chloro-substituted analog in complex 17, and as a consequence this might reduce the tendency of the substituents pointing towards the same direction in the metallacyclobutane transition state what in turn is believed to be the prerequisite to form an all cis structure.

Some of the results were summarized in Table 1, below.

TABLE 1

Polymerization of endo-DCPD with catalysts 1-18.

| catalyst | entry | equiv. monomer [a] | t [b] | cis (%) [c] | tacticity [c] |
|---|---|---|---|---|---|
| 1 | 2 | 100 | 60 s | 18 | 55% iso |
|  | 3 | 200 | 120 s | 20 | 57% iso |
| 2 | 4 | 50 | <20 s | 90 | >95% iso |
|  | 5 | 100 | 30 s | 90 | >95% iso |
|  | 6 | 200 | <60 s | 87 | 91% iso |
| 3 | 7 | 50 | 25 min | 85 | 70% syndio |
|  | 8 | 100 | 60 min | 83 | 73% syndio |
| 4 | 9 | 100 | 30 s | 68 | 55% syndio |
| 5 | 11 | 50 | 30 s | 100 | 100% syndio |
|  | 12 | 100 | 60 s | 100 | 100% syndio |
|  | 13 | 200 | 150 s | 100 | 100% syndio |
| 6 | 14 | 200 | 30 s | — [d] | — |
| 7 | 15 | 200 | 30 s | — | — |
| 8 | 16 | 100 | 30 s | 62 | 53% syndio |
| 9 | 17 | 100 | 60 s | 44 | — |
| 10 | 18 | 100 | 5 min | 60 | — |
| 11 | 19 | 50 | 60 s | 100 | 75% syndio |
|  | 20 | 100 | <120 s | 100 | 78% syndio |
| 12 | 21 | 50 | 60 s | 100 | 100% syndio |
|  | 22 | 100 | <120 s | 100 | 100% syndio |
| 13 | 23 | 50 | 30 min | 100 | 70% syndio |
| 14 | 24 | 50 | <30 s | 100 | 70% iso |
|  | 25 | 100 | <60 s | 100 | 73% iso |
| 15 | 26 | 50 | 60 s | 90 | Not determined |
| 16 | 27 | 50 | 30 s | 100 | 66% syndio |
| 17 | 28 | 50 | 180 s | 100 | 70% iso |
| 18 | 29 | 50 | 120 s | 81 | 63% iso |

[a] With respect to one equivalent catalyst.
[b] Time until 100% monomer conversion.
[c] Determined by $^{13}$C NMR.
[d] Not determined due to partial insolubility or unclear NMR spectra.

Figure 9:
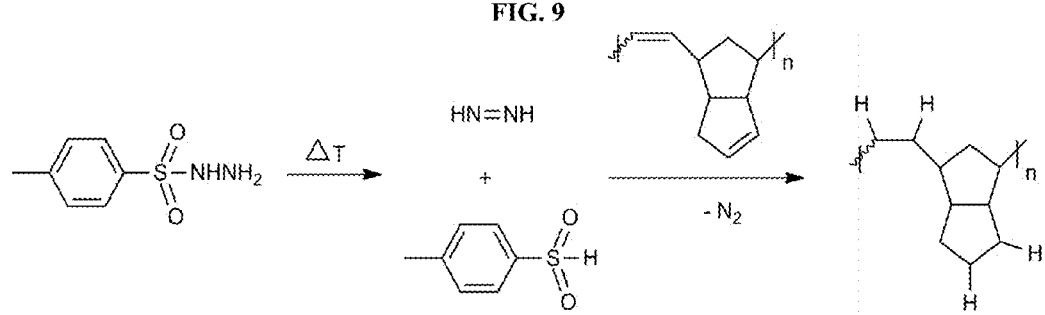
FIG. 9. Hydrogenation of poly(DCPD) with diimine generated in situ.

Preparation of Hydrogenated H-Poly(DCPD) and Investigation of Thermal Properties In some embodiments, the present invention provides highly syndiotactic hydrogenated poly(DCPD). The poly (DCPD)s were hydrogenated by diimine generated in situ from p-toluenesulfonyl hydrazide (p-Tos-NHNH$_2$, FIG. 9). Other suitable hydrogenation methods are also widely known in the art. In order to achieve complete saturation the polymers were solubilized throughout the entire reaction. The hydrogenation reactions were performed in a pressure tube at 130° C. using four equivalents of p-Tos-NHNH$_2$ per DCPD-unit and chloroform as the solvent.

Figure 10:
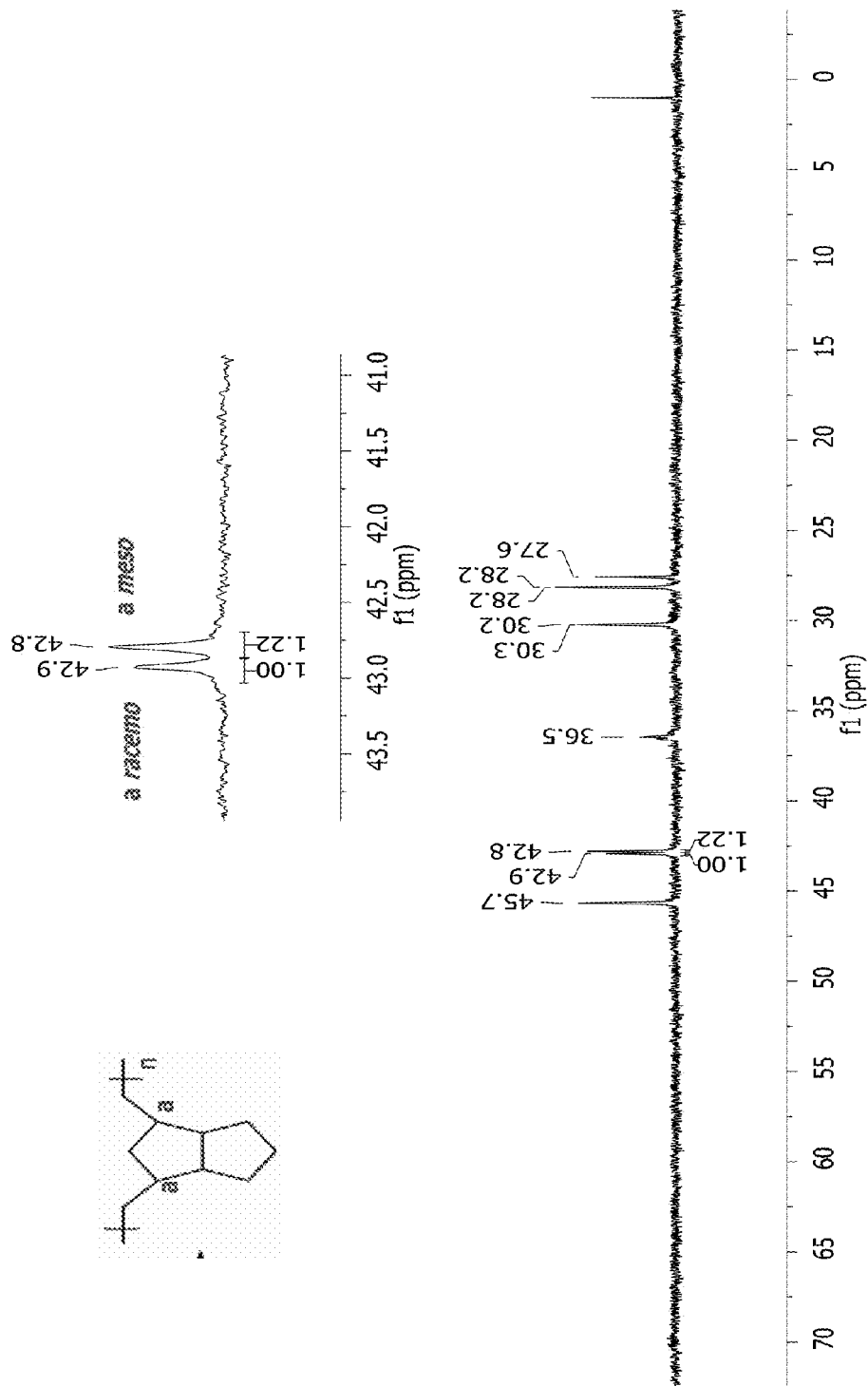
FIG. 10. $^{13}$C NMR (CDCl$_3$) of atactic H-poly(DCPD) derived by the reaction of compound 1 (Table 1, entry 2). The signal for C(a) at 42.9 ppm is indicative for a syndiotactic structure; the signal at 42.8 ppm is indicative for an isotactic structure.
Figure 18:
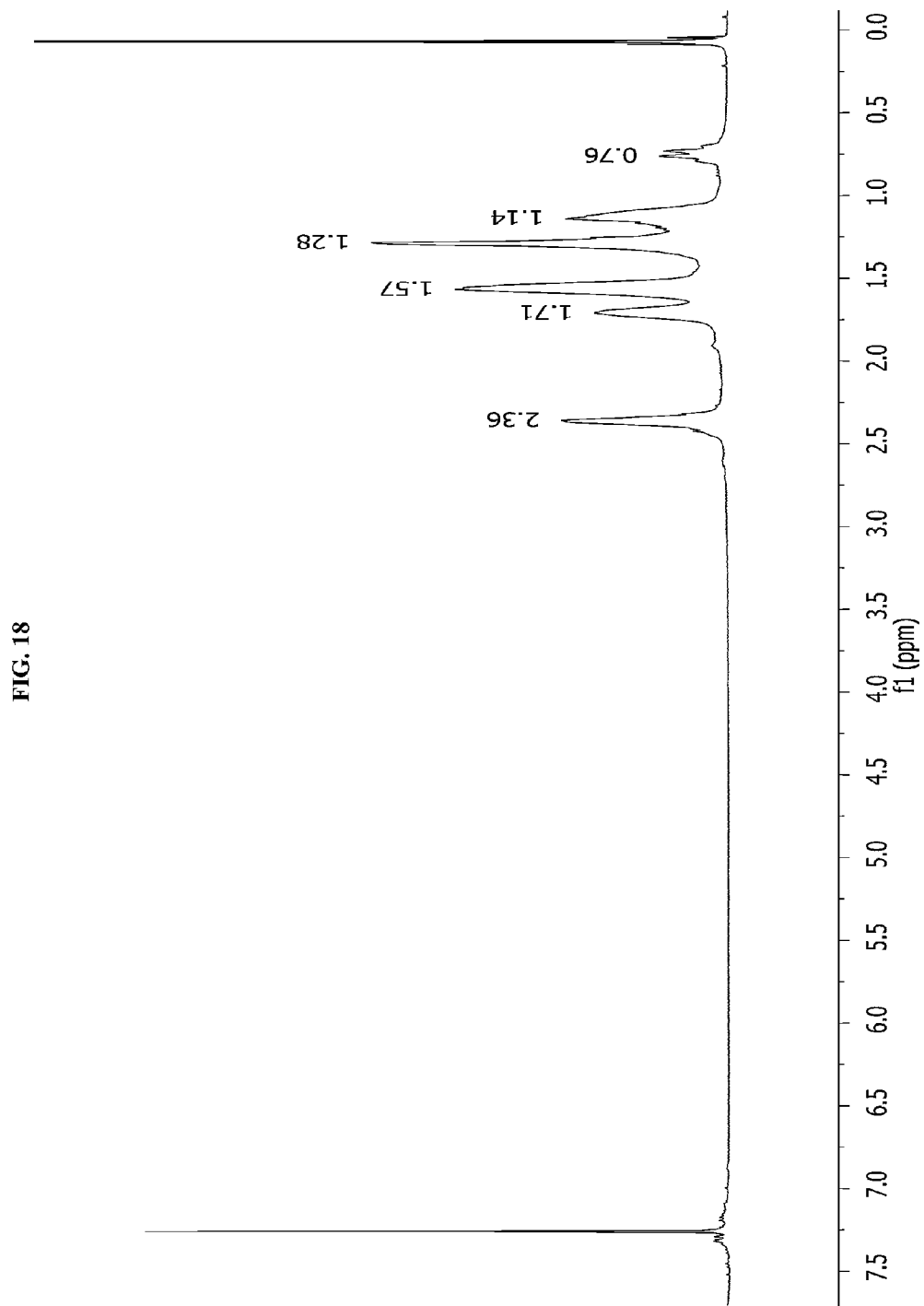
FIG. 18. $^1$H NMR (CDCl$_3$) of atactic H-poly(DCPD) derived by the reaction of compound 1. The absence of signals in the olefinic region demonstrates complete hydrogenation.

Hydrogenated poly(DCPD) (H-poly(DCPD)) derived from atactic poly(DCPD) prepared by catalyst 1 was soluble in chloroform at room temperature; its $^{13}$C NMR spectrum was shown in FIG. 10 (for the corresponding $^1$H NMR see FIG. 18). Complete saturation was illustrated by the absence of olefinic signals in both the $^{13}$C and the $^1$H NMR spectra. The $^{13}$C NMR showed six signals, thereby the signal for the methine carbon C(a) splits due to iso- and syndiostereoregularity, respectively. The signal at 42.9 ppm can be assigned to a syndiotactic structure; the signal at 42.8 ppm is indicative for an isotactic structure[8,10,28].

Figure 19:
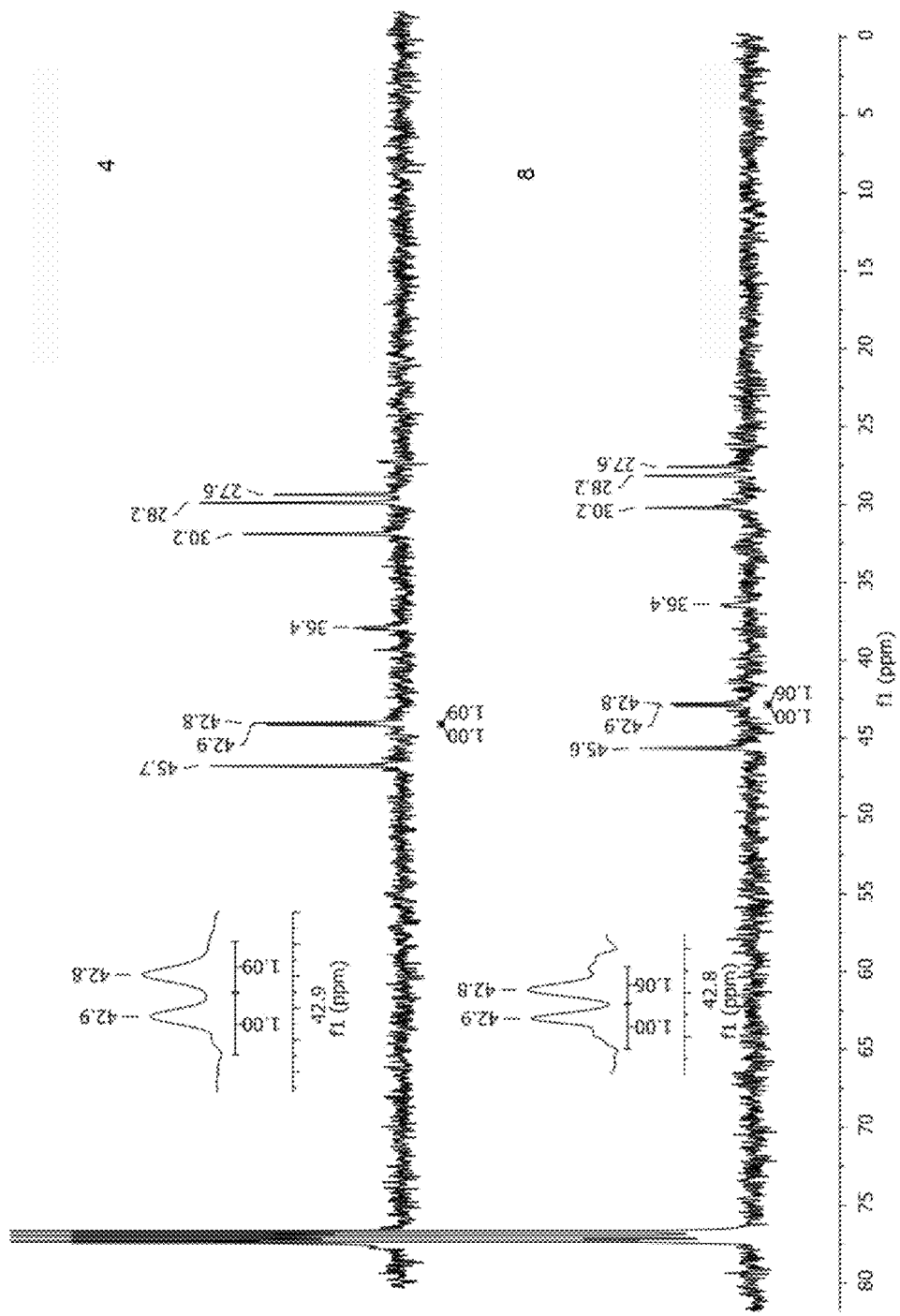
FIG. 19. $^{13}$C NMR (CDCl$_3$) of atactic H-poly(DCPD) derived by the reaction of compounds 4 (top) and 8 (bottom).
Figure 20:
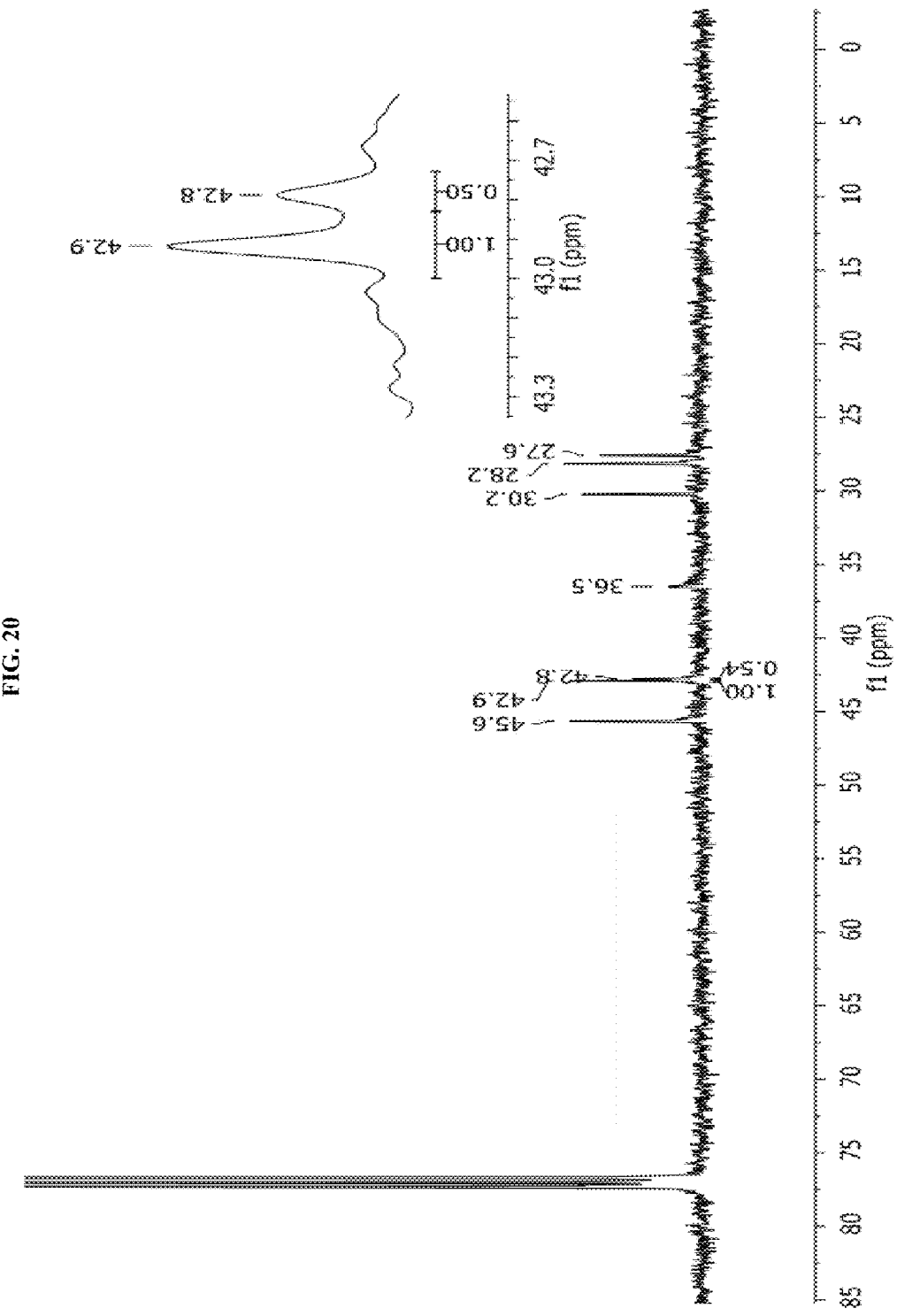
FIG. 20. $^{13}$C NMR (CDCl$_3$) of 70% syndiotactic H-poly(DCPD) derived by the reaction of compound 3.
Figure 21:
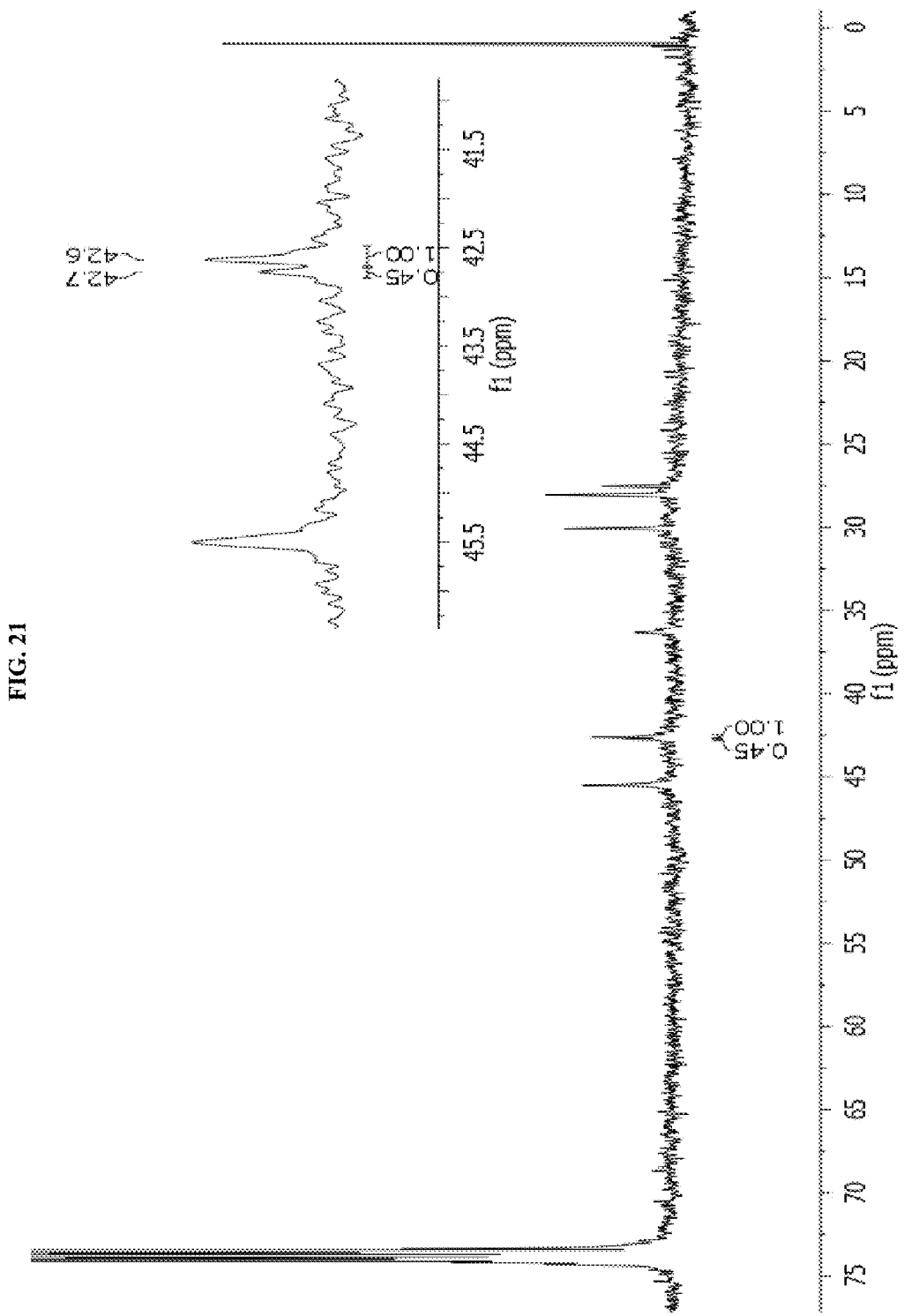
FIG. 21. $^{13}$C NMR (CDCl$_3$) of 70% isotactic H-poly(DCPD) derived by the reaction of compound 14.

The atactic polymers prepared by molybdenum MAP complexes 4 and 8 remained well soluble upon hydrogenation; their $^{13}$C NMR spectra are shown in FIG. 19. Generally it is observed that the more structured the parent poly (DCPD)s are, the less soluble are the resulting H-poly (DCPD)s. Tungsten MAP catalyst 3 was found to give a 80% cis structured 70% syndiotactic poly(DCPD); the hydrogenated version of this polymer is soluble in CHCl$_3$ when made up of theoretically up to 100 monomer units (for the $^{13}$C NMR see FIG. 20). The unsaturated as well as the hydrogenated version of the 70% isotactic polymer generated by the reaction of 14 proved to be less soluble than its 70% syndiotactic analog. The $^{13}$C NMR of a 70% isotactic H-poly(DCPD) consisting theoretically of 50 monomer units was shown in FIG. 21. At room temperature, the highly structured polymers derived from catalysts 2 (isotactic), 5 and 12 (syndiotactic) were entirely insoluble in common organic solvents. The solubility increases with decreasing molecular weight but even for the H-poly(DCPD)s theoretically made up of only 50 monomer units a temperature of 100° C. is necessary to obtain a decent $^1$H NMR spectra. Without the intention to be limited by theory, this observation is a further hint for the highly ordered, crystalline structure of these polymers.

Figure 11:
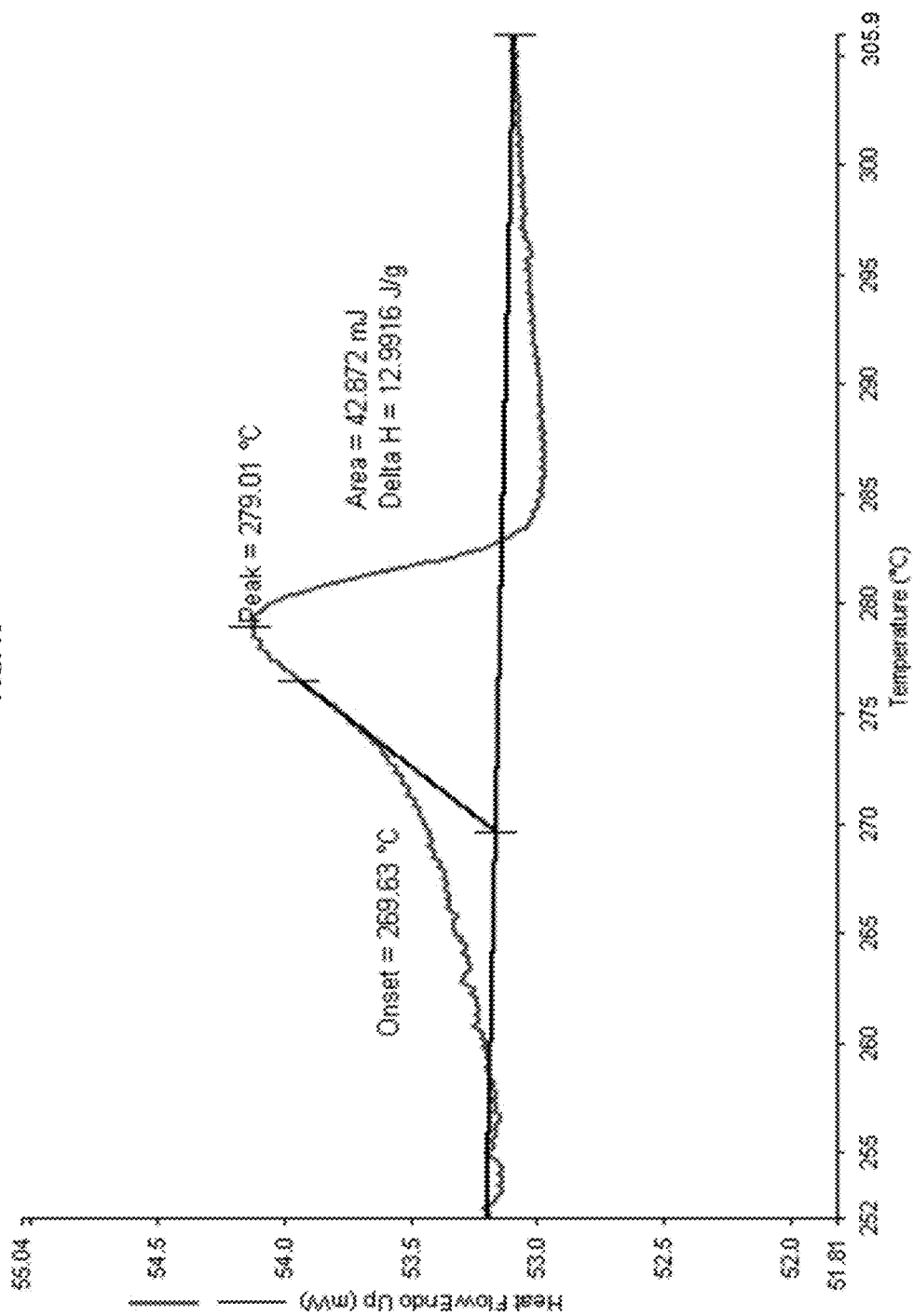
FIG. 11. DSC thermogram of isotactic H-poly(DCPD) obtained by catalyst 2, indicating a melting point at around 280° C. in the first heating cycle. The ratio DCPD:2 was 50:1.
Figure 22:
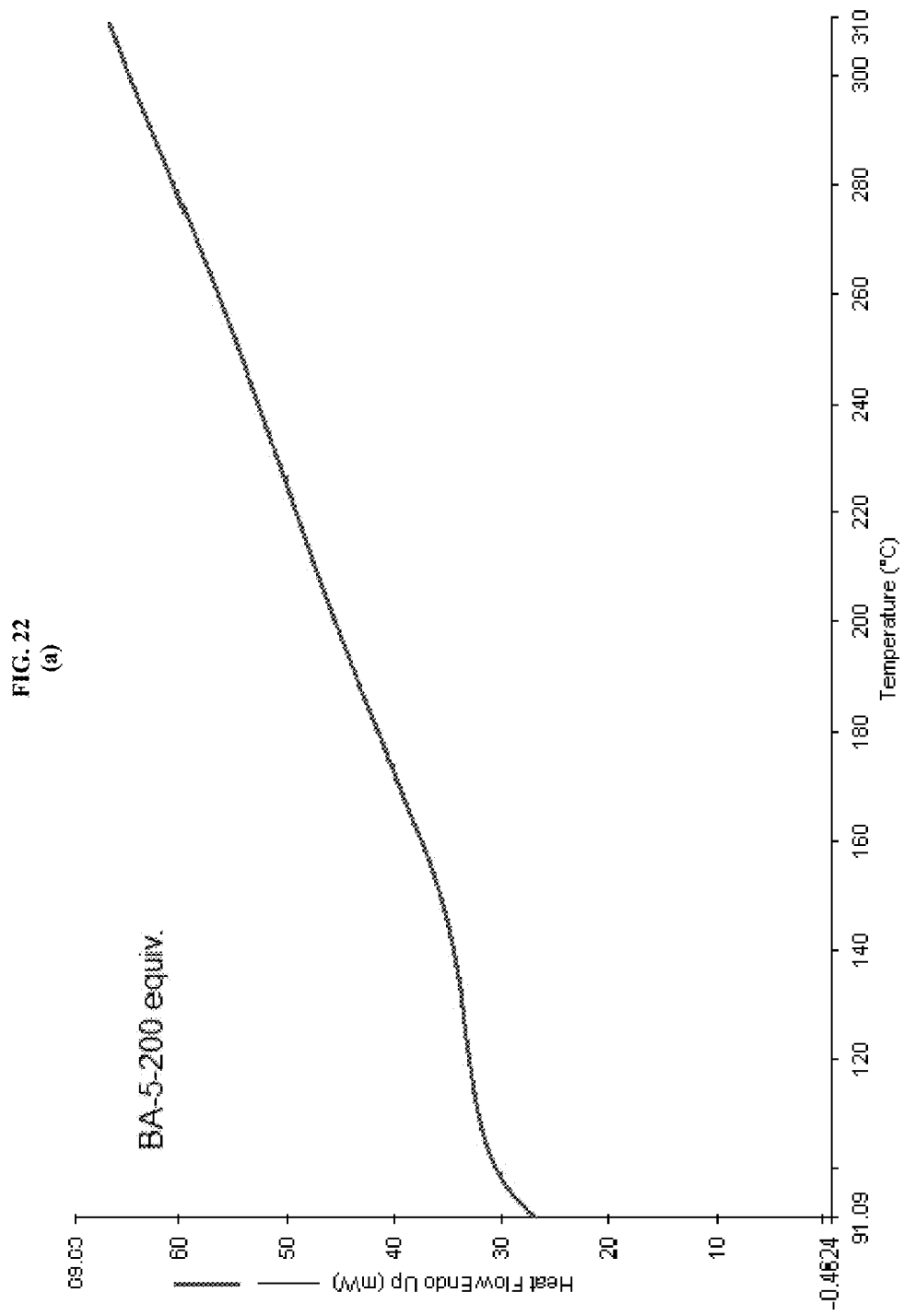
FIG. 22. DSC thermogram of amorphous cis, syndiotactic poly(DCPD) obtained by catalyst 5 showing a faint T$_g$ at ~150° C. (a). The corresponding crystalline syndiotactic H-poly(DCPD) shows a melting point at around 270° C. in the first heating cycle (b). The ratio DCPD:5 was 200:1.
Figure 22:
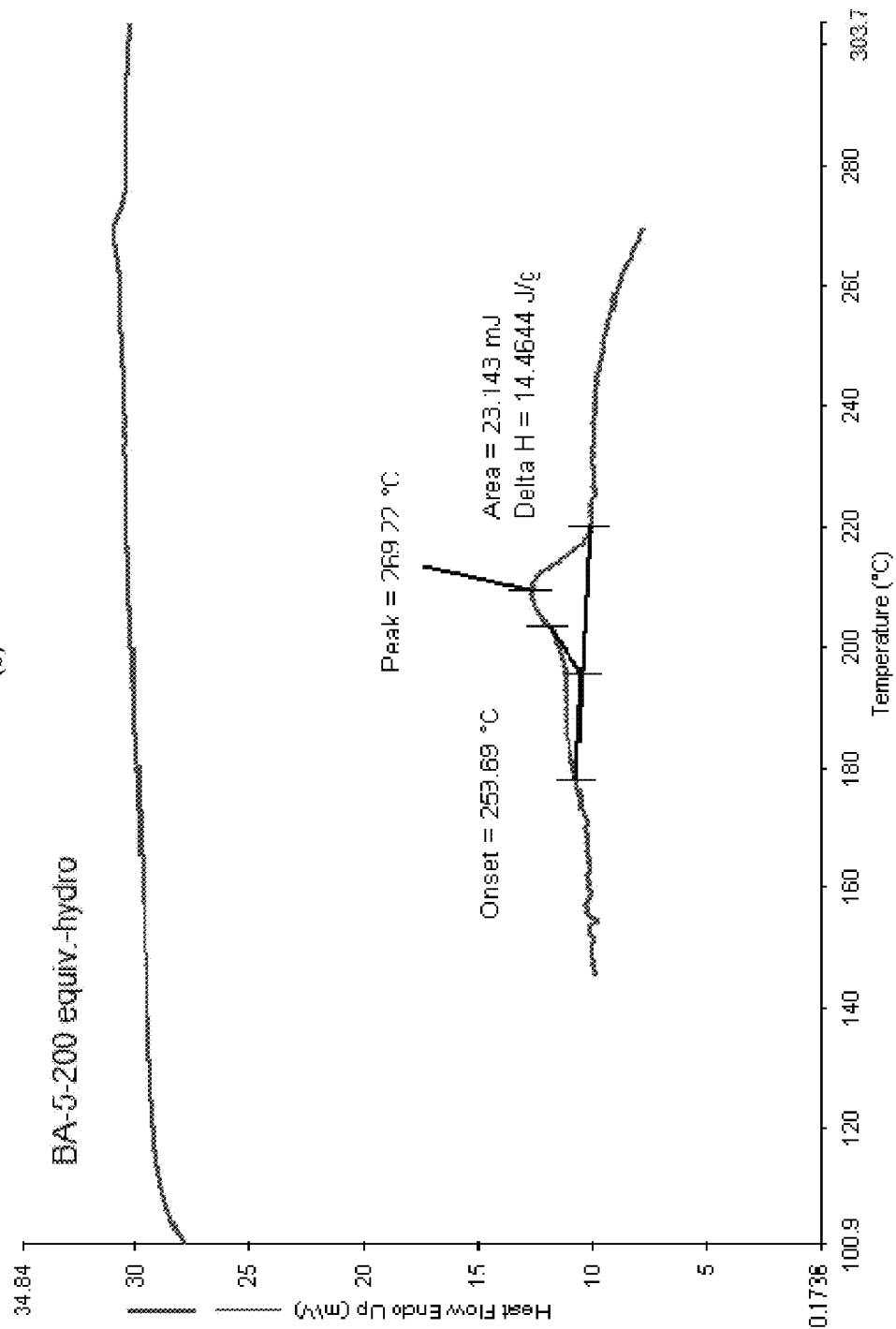

Thermal properties of some of the ROMP derived poly (DCPD)s as well as their analogous hydrogenated versions were characterized by differential scanning calorimetry (DSC). The atactic poly(DCPD)s prepared by catalysts 1 and 4, as well as the corresponding well soluble H-poly(DCPD)s did not show melting points. The atactic poly(DCPD)s and H-poly(DCPD)s were amorphous polymers and did not possess crystalline melting behavior. The DSC thermogram of cis, syndiotactic poly(DCPD) obtained by catalyst 5 showed a glass transition temperature ($T_g$) at ~150° C., indicating this polymer as an amorphous material, too. In contrast, the corresponding crystalline syndiotactic H-poly (DCPD) exhibited a melting point of around 270° C. (FIG. 22). FIG. 11 exemplarily displayed the DSC thermogram of highly isotactic H-poly(DCPD) prepared by molybdenum complex 2. The insoluble, crystalline material possessed a melting point at around 280° C. Other than the atactic and syndiotactic poly(DCPD)s, the poorly soluble, highly isotactic, 90% cis configured poly(DCPD) showed a first order transition at 275° C. in addition to a faintly pronounced $T_g$ at 200° C. These observations agreed well with data reported in the literature[10,21,22,23]. The data indicate that the atactic poly(DCPD)s and H-poly(DCPD)s as well as the cis, syndiotactic poly(DCPD) are amorphous polymers; in contrast, the hydrogenated syndiotactic H-poly(DCPD) and both the unsaturated cis, isotactic and the hydrogenated isotactic polymer are crystalline materials featuring high melting points.

Stereochemical control of ROMP of highly reactive monomers such as endo-dicyclopentadiene was notoriously difficult prior to the present invention. As exemplified by the non-limiting examples described herein, the present invention, among other things, provides well defined metal complexes and methods that allow to tame such reactive monomers; stereochemically controlled, smooth and rapid ROMP at mild temperature provided by the present invention affords poly(DCPD) and hydrogenated poly(DCPD) with unprecedented and surprising high syndiotacticity.

Experimental

General:

ROMP reactions were conducted in a $N_2$ mediated glove box. Endo-dicyclopentadiene was purchased from Sigma-Aldrich and was distilled prior to use. p-Toluenesulfonyl hydrazide (p-Tos-$NHNH_2$) was purchased from Sigma-Aldrich and was used without further purification.

NMR spectra were recorded on a Bruker Avance III 400 spectrometer in $CDCl_3$ at 25° C. or in $C_2D_2Cl_4$ at elevated temperatures and data were listed in parts per million (ppm) downfield from tetramethylsilane (TMS) as an internal standard.

Differential scanning calorimetry (DSC) measurements have been performed on a Perkin Elmer Pyris 1 power compensated differential scanning calorimeter.

ROMP Reactions:

All polymerizations were performed at room temperature unless otherwise specified. To a stirred dichloromethane solution containing 2 wt. % DCPD (20 mg DCPD/1 g $CH_2Cl_2$), a solution of the respective catalyst was added in one portion (0.5-2.0 mol % catalyst in 0.2 mL $CH_2Cl_2$). By adding benzaldehyde, the reaction was terminated after a specific period of time (Table 1). The poly(DCPD)s were precipitated from methanol and dried in vacuo.

cis, syndiotactic poly(DCDP):

$^{13}C$ NMR (100.61 MHz, $CDCl_3$): δ=132.4, 132.1, 131.5, 131.2, 130.8, 55.1/54.9 (d), 45.0/44.9 (d), 42.4/42.2 (d), 41.7/41.5 (d), 39.1, 34.7 ppm.

cis, isotactic poly(DCDP):

$^{13}C$ NMR (100.61 MHz, $CDCl_3$): δ=132.7, 132.4, 131.6, 131.5, 130.7, 55.7/55.6 (d), 45.4/45.3 (d), 42.4/42.2 (d), 41.7/41.5 (d), 38.8, 34.8 ppm.

Hydrogenation of poly(DCPD):

Hydrogenation reactions were performed at 130° C. using a pressure tube. To a chloroform solution containing 2 wt % poly(DCPD), four equivalents of p-Tos-$NHNH_2$ per DCPD-unit were added. Under vigorously stirring, the reaction was conducted for 6 h. The reaction mixture was allowed to cool to room temperature and was then poured into excess methanol. After washing repeatedly with methanol, the H-poly(DCPD) samples were dried in vacuo.

syndiotactic H-poly(DCDP):

$^{13}C$ NMR (100.61 MHz, $C_2D_2Cl_4$): δ=45.6, 42.9, 36.5, 30.2, 28.2, 27.6 ppm.

isotactic H-poly(DCDP):

$^{13}C$ NMR (100.61 MHz, $C_2D_2Cl_4$): δ=45.5, 42.6, 36.3, 30.1, 28.1, 27.5 ppm.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The invention claimed is:

1. A method for preparing a poly(dicyclopentadiene) polymer, wherein the polymer is greater than 80% syndiotactic, comprising a step of:

a) providing a compound of formula I:

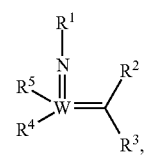

wherein:

R¹ is —C(R¹ᵃ)₃;

each R¹ᵃ is independently an optionally substituted group selected from C₁₋₁₀ aliphatic, C₁₋₁₀ heteroalkyl having 1-3 heteroatoms independently selected from nitrogen, oxygen or sulfur, phenyl, a 3-7 membered saturated or partially unsaturated carbocyclic ring, an 8-10 membered bicyclic or polycyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; or:

two R¹ᵃ groups are optionally taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur; or:

three R¹ᵃ groups are optionally taken together with the carbon atom to which they are attached to form an optionally substituted 4-10 membered, bicyclic or polycyclic, saturated or partially unsaturated ring having 0-4 heteroatoms independently selected from nitrogen, oxygen or sulfur;

each of R² and R³ is independently —R, —OR, —SR, —N(R)₂, —OC(O)R, —S(O)R, —SO₂R, —SO₂N(R)₂, —C(O)N(R)₂, —NRC(O)R, or —NRSO₂R; or:

R² and R³ are optionally taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur;

each R is independently hydrogen or an optionally substituted group selected from C₁₋₁₀ aliphatic, C₁₋₁₀ heteroalkyl having 1-3 heteroatoms independently selected from nitrogen, oxygen or sulfur, phenyl, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; or:

two R groups are optionally taken together with the intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen or sulfur;

R⁴ is optionally substituted 5-14 membered heteroaryl having 1-4 heteroatoms independently selected from nitrogen, oxygen or sulfur, wherein at least one heteroatom is nitrogen;

R⁵ is —OArᵃ; and

Arᵃ is optionally substituted

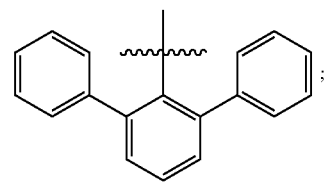 [SMILES: *c1c(-c2ccccc2)cccc1-c1ccccc1]

or a compound of formula II:

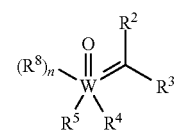

II wherein:

each of R² and R³ is independently —R, —OR, —SR, —N(R)₂, —OC(O)R, —S(O)R, —SO₂R, —SO₂N(R)₂, —C(O)N(R)₂, —NRC(O)R, or —NRSO₂R; or:

R² and R³ are optionally taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur;

each R is independently hydrogen or an optionally substituted group selected from C₁₋₁₀ aliphatic, C₁₋₁₀ heteroalkyl having 1-3 heteroatoms independently selected from nitrogen, oxygen or sulfur, phenyl, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; or:

two R groups are optionally taken together with the intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen or sulfur;

R⁴ is optionally substituted 5-14 membered heteroaryl having 1-4 heteroatoms independently selected from nitrogen, oxygen or sulfur, wherein at least one heteroatom is nitrogen;

R⁵ is —OArᵃ;

Arᵃ is optionally substituted

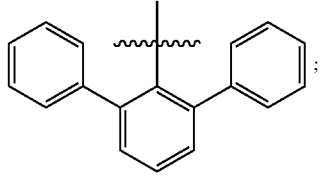 [SMILES: *c1c(-c2ccccc2)cccc1-c1ccccc1]

;

n is 0-2; and each R⁸ is independently a phosphorus-containing ligand, wherein the phosphorus-containing ligand is bonded to W through a phosphorus atom;

or a compound of formula III:

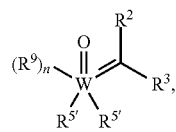

III wherein:

each of R² and R³ is independently —R, —OR, —SR, —N(R)₂, —OC(O)R, —S(O)R, —SO₂R, —SO₂N(R)₂, —C(O)N(R)₂, —NRC(O)R, or —NRSO₂R; or:

R² and R³ are optionally taken together with the carbon atom to which they are attached to form an optionally substituted 3-10 membered, monocyclic, bicyclic or polycyclic, saturated or partially unsaturated ring having 0-4 heteroatoms independently selected from nitrogen, oxygen or sulfur;

each R is independently hydrogen or an optionally substituted group selected from C₁₋₁₀ aliphatic, C₁₋₁₀ heteroalkyl having 1-3 heteroatoms independently selected from nitrogen, oxygen or sulfur, phenyl, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; or:

two R groups are optionally taken together with the intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen or sulfur;

each R⁵' is independently —OArᵇ;

Arᵇ is

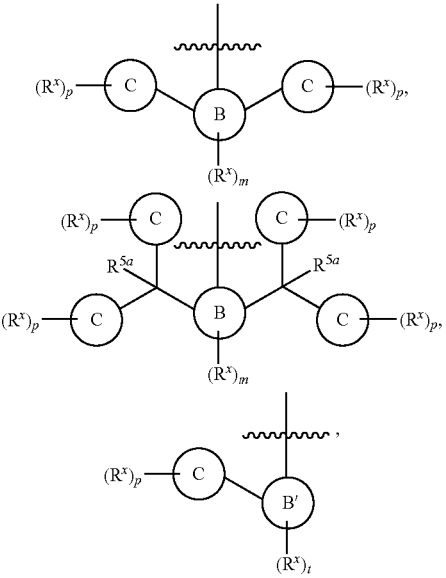

or an optionally substituted group selected from phenyl, a 10-14 membered bicyclic or polycyclic aryl ring, a 5-6 membered monocyclic heteroaryl ring having 1-4 heteroatoms independently selected from nitrogen, oxygen or sulfur, or an 8-14 membered bicyclic or polycyclic heteroaryl ring having 1-5 heteroatoms independently selected from nitrogen, oxygen or sulfur;

Ring B is an optionally substituted group selected from phenyl or a 5-6 membered monocyclic heteroaryl ring having 1-4 heteroatoms independently selected from nitrogen, oxygen or sulfur;

Ring B' is an optionally substituted group selected from phenyl, a 10-14 membered bicyclic or tricyclic aryl ring, a 5-6 membered monocyclic heteroaryl ring having 1-4 heteroatoms independently selected from nitrogen, oxygen or sulfur, or an 8-14 membered bicyclic or tricyclic heteroaryl ring having 1-5 heteroatoms independently selected from nitrogen, oxygen or sulfur;

each Ring C is independently an optionally substituted group selected from phenyl, a 3-7 membered saturated or partially unsaturated carbocyclic ring, an 6-14 membered bicyclic or tricyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-14 membered bicyclic or tricyclic heteroaryl ring having 1-5 heteroatoms independently selected from nitrogen, oxygen or sulfur;

each Rˣ is independently R, halogen, —CN, —C(O)R, —C(O)OR, —C(O)N(R)₂, —C(O)N(R)(OR), —OR, —OC(O)R, —OC(O)N(R)₂, —OSi(R)₃, —SR, —S(O)R, —S(O)₂R, —S(O)₂OR, —S(O)₂N(R)₂, —NO₂, —N(R)₂, —NROR, —NRC(O)R, —N(R)C(O)OR, —N(R)C(O)N(R)₂, —N(R)S(O)₂R, —N(R)S(O)₂N(R)₂, —P(R)₂, —P(OR)₂, —P(O)(R)₂, —P(O)(OR)₂, —P(O)[N(R)₂]₂, or —Si(R)₃;

each R⁵ᵃ is independently R;

each of p and t is independently 0-7;
m is 0-3;
n is 0-2; and
each $R^9$ is independently a neutral ligand.

2. The method of claim 1, wherein double bonds in the polymer backbone is greater than 90% cis.

3. The method of claim 1, wherein double bonds in the polymer backbone is greater than 95% cis.

4. The method of claim 1, wherein the polymer is a hydrogenated poly(dicyclopentadiene) polymer.

5. The method of claim 1, wherein the polymer is greater than 90% syndiotactic.

6. The method of claim 1, wherein the polymer is greater than 95% syndiotactic.

7. The method of claim 1, wherein $M_n$ of the polymer is greater than about 5,000.

8. The method of claim 1, wherein each $R^{1a}$ is optionally substituted $C_{1-6}$ aliphatic or phenyl.

9. The method of claim 1, wherein $R^1$ is

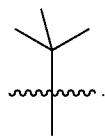 [SMILES: *C(C)(C)C]

10. The method of claim 1, wherein the compound is a compound of formula II.

11. The method of claim 10, wherein the compound of formula II has the structure of formula II-a:

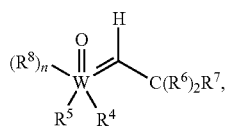

II-a wherein:
$R^4$ is optionally substituted 5-14 membered heteroaryl having 1-4 heteroatoms independently selected from nitrogen, oxygen or sulfur, wherein at least one heteroatom is nitrogen;
$R^5$ is —$OAr^a$;
$Ar^a$ is optionally substituted

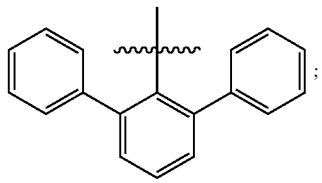 [SMILES: *c1c(-c2ccccc2)cccc1-c1ccccc1]

each $R^6$ is independently —R, —OR, —SR, —N(R)$_2$, —OC(O)R, —S(O)R, —SO$_2$R, —SO$_2$N(R)$_2$, —C(O)N(R)$_2$, —NRC(O)R, or —NRSO$_2$R;

each R is independently hydrogen or an optionally substituted group selected from $C_{1-10}$ aliphatic, $C_{1-10}$ heteroalkyl having 1-3 heteroatoms independently selected from nitrogen, oxygen or sulfur, phenyl, a 3-7 membered saturated or partially unsaturated carbocyclic ring, a 6-10 membered bicyclic saturated, partially unsaturated or aryl ring, a 5-6 membered monocyclic heteroaryl ring having 1-4 heteroatoms independently selected from nitrogen, oxygen or sulfur, a 3-7 membered saturated or partially unsaturated heterocyclic ring having 1-3 heteroatoms independently selected from nitrogen, oxygen or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur; or:

two R groups are optionally taken together with the intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen or sulfur;

$R^7$ is optionally substituted phenyl;
n is 0-2; and
each $R^8$ is independently a phosphorus-containing ligand, wherein the phosphorus-containing ligand is bonded to W through a phosphorus atom.

12. The method of claim 1, wherein $R^4$ is optionally substituted

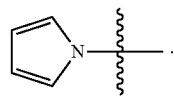

13. The method of claim 1, wherein the compound is a compound of formula III.

14. The method of claim 13, wherein the compound is coordinated to a Lewis acid having the structure of B(R)$_3$.

15. The method of claim 1, further comprising a step of:
b) providing a Lewis acid.

16. The method of claim 15, comprising providing a compound of formula III, and the Lewis acid is B(R)$_3$.

* * * * *